United States Patent
Guo et al.

(10) Patent No.: US 11,174,254 B2
(45) Date of Patent: Nov. 16, 2021

(54) ANILINE-SUBSTITUTED 1,2-DIHYDROPYRROL[3,4-C] PYRIDIN/PYRIMIDIN-3-ONE DERIVATIVE AND USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Shuchun Guo, Shanghai (CN); Fusheng Zhou, Shanghai (CN); Xiang Chen, Shanghai (CN); Jinzhu Zhao, Shanghai (CN); Dong Huang, Shanghai (CN); Jing Xie, Shanghai (CN); Changjiang Qiao, Shanghai (CN); Wan He, Shanghai (CN); Kai Zhang, Shanghai (CN); Xi Chen, Shanghai (CN); Jiong Lan, Shanghai (CN)

(73) Assignees: YANGTZE RIVER PHARMACEUTICAL GROUP CO., LTD., Jiangsu (CN); SHANGHAI HAIYAN PHARMACEUTICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 16/486,110

(22) PCT Filed: Aug. 3, 2018

(86) PCT No.: PCT/CN2018/098479
§ 371 (c)(1),
(2) Date: Aug. 14, 2019

(87) PCT Pub. No.: WO2019/062328
PCT Pub. Date: Apr. 4, 2019

(65) Prior Publication Data
US 2020/0048248 A1 Feb. 13, 2020

(30) Foreign Application Priority Data
Sep. 28, 2017 (CN) .......................... 201710897909.5

(51) Int. Cl.
| | |
|---|---|
| C07D 471/04 | (2006.01) |
| A61P 35/00 | (2006.01) |
| C07D 487/04 | (2006.01) |
| A61P 35/04 | (2006.01) |
| C07D 519/00 | (2006.01) |

(52) U.S. Cl.
CPC ............ *C07D 471/04* (2013.01); *A61P 35/00* (2018.01); *A61P 35/04* (2018.01); *C07D 487/04* (2013.01); *C07D 519/00* (2013.01)

(58) Field of Classification Search
CPC .. C07D 471/04; C07D 519/00; C07D 487/04; A61K 31/437; A61K 31/519
See application file for complete search history.

(56) References Cited

U.S. PATENT DOCUMENTS

| | | |
|---|---|---|
| 8,440,689 B2 | 5/2013 | Arikawa et al. |
| 2011/0152273 A1* | 6/2011 | Arikawa ................. A61P 27/02 |
| | | 514/249 |
| 2016/0264548 A1 | 9/2016 | Qiu et al. |

FOREIGN PATENT DOCUMENTS

| | | |
|---|---|---|
| CA | 3012882 | 8/2017 |
| CN | 102753548 A | 10/2012 |
| CN | 105939998 | 9/2016 |
| CN | 107021963 | 8/2017 |
| WO | 2012/177714 | 12/2012 |

(Continued)

OTHER PUBLICATIONS

Lam et al. "Discovery of TAK-659 an orally available investigational inhibitor of Spleen Tyrosine Kinase (SYK)" Bioorg. Med. Chem. Lett. 2016, 26, 5947-5950. (Year: 2016).*

(Continued)

*Primary Examiner* — Amanda L. Aguirre
(74) *Attorney, Agent, or Firm* — Adsero IP

(57) ABSTRACT

The present invention relates to a 1,2-dihydropyrrol[3,4-c] pyridin/pyrimidin-3-one derivative substituted by N-(3-aminophenyl)acrylamide and a preparation method and pharmaceutical use thereof. In particular, the present invention relates to a compound of formula (II) or a pharmaceutically acceptable salt, stereoisomer, solvate, or prodrug thereof and a preparation method and application of the same. The definition of each substituent in the formula is described in detail in the specification and claims.

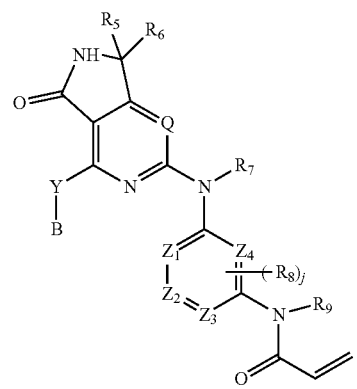

12 Claims, No Drawings

(56) References Cited

FOREIGN PATENT DOCUMENTS

| WO | 2015/048662    | 4/2015 |
|----|----------------|--------|
| WO | 2015/061247    | 4/2015 |
| WO | 2015/131080    | 9/2015 |
| WO | 2017075394 A1  | 5/2017 |
| WO | 2017/128917 W  | 8/2017 |

OTHER PUBLICATIONS

English translation of International Search Report for PCT/CN2018/098479, dated Sep. 19, 2018, 2 pages.
European extended search report, dated May 18, 2020, 8 pages.
International Search Report for PCT/CN2018/098481, dated Sep. 13, 2018, 2 pages.
Office Action for Australia Application 2018342342, dated Jun. 4, 2020, 3 pages.

\* cited by examiner

ANILINE-SUBSTITUTED 1,2-DIHYDROPYRROL[3,4-C] PYRIDIN/PYRIMIDIN-3-ONE DERIVATIVE AND USE THEREOF

CROSS-REFERENCE TO RELATED APPLICATION

This application claims priority to and is a 35 U.S.C. § 371 national phase application of PCT/CN2018/098479 (WO 2019/062328), filed on Aug. 3, 2018 entitled "ANILINE-SUBSTITUTED 1,2-DIHYDROPYRROL[3,4-C] PYRIDIN/PYRIMIDIN-3-ONE DERIVATIVE AND USE THEREOF", which application claims priority to and the benefit of Chinese Application CN 201710897909.5 filed Sep. 28, 2017.

TECHNICAL FIELD

The present disclosure belongs to the field of medical technology. In particular, the present disclosure relates to an aniline-substituted 1,2-dihydropyrrolo[3,4-c]pyridin/pyrimidin-3-one derivative, preparation method thereof, use thereof as a BTK inhibitor, and a pharmaceutical composition prepared therefrom.

BACKGROUND

BTK kinase, a non-receptor tyrosine kinase in the TEC kinase family and a key regulator of the BCR signaling pathway, plays an important role in B cell maturation, proliferation and survival.

BTK is overexpressed in a variety of B-cell lymphomas and is the only clinically proven and effective target for drug development in the TEC kinase family. Inhibition of BTK can inhibit proliferation of a range of B cell lymphomas.

Activation of B cell antigen receptor (BCR) signaling pathway plays an important role in inducing and maintaining B cell malignancies and autoimmune diseases. Bruton's tyrosine kinase (Btk) plays a key role in the hematopoietic cell BCR signaling pathway and is a very good target for new lymphoma therapy. BTK inhibitors act on the BCR pathway, inhibit Btk autophosphorylation, phosphorylation of Btk's physiological substrate PLCγ and phosphorylation of the downstream kinase ERK.

BTK inhibitors act on chronic lymphocytic leukemia (CLL) cells, induce cytotoxicity, and inhibit the proliferation of CLL cells. BTK inhibitors inhibit the proliferation of primary B cells activated by BCR and the secretion of TNFα, IL-1β and IL-6 in primary monocytes. BTK inhibitors act on collagen-induced arthritis models and significantly reduce clinical arthritis symptoms such as foot swelling and joint inflammation by inhibiting B cell activity.

Currently, only one BTK inhibitor, ibrutinib, has been approved for marketing, so it is necessary to develop more active, safer and more effective BTK inhibitors.

SUMMARY OF THE DISCLOSURE

It is an object of the present disclosure to provide a novel class of compounds which are useful as BTK inhibitors.

In the first aspect of the present disclosure, a compound of formula (I), or a pharmaceutically acceptable salt, stereoisomer, solvate or prodrug thereof is provided:

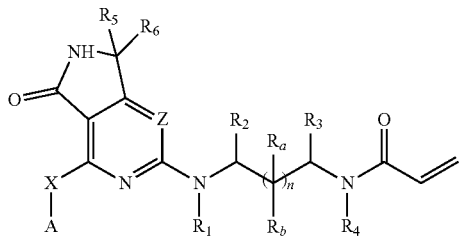

wherein X is selected from the group consisting of a bond, $NR_{a1}$, S, SO, $SO_2$ and O; wherein $R_{a1}$ is selected from the group consisting of hydrogen, hydroxy and $C_{1-8}$ alkyl (preferably $C_{1-6}$ alkyl, more preferably $C_{1-3}$ alkyl);

A is selected from the group consisting of $C_{6-10}$ aryl (preferably phenyl), a 4- to 7-membered saturated or unsaturated monoheterocyclic ring, a 5- to 6-membered monocyclic heteroaryl ring, and an 8- to 10-membered bicyclic heteroaryl ring;

Z is N or $CR_{b1}$; wherein $R_{b1}$ is selected from the group consisting of hydrogen, halogen (preferably fluorine, chlorine, bromine), cyano, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) and $C_{3-8}$ cycloalkoxy (preferably $C_{3-6}$ cycloalkoxy);

$R_5$ and $R_6$ are each independently selected from the group consisting of hydrogen, halogen (preferably fluorine, chlorine, bromine), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) and $C_{3-8}$ cycloalkoxy (preferably $C_{3-6}$ cycloalkoxy);

n is 0 or 1; wherein (i) when n is 0, $R_1$ and $R_3$ are each independently selected from the group consisting of hydrogen, halogen, hydroxy, alkoxy, and $C_{1-8}$ alkyl (preferably $C_{1-6}$ alkyl, more preferably $C_{1-3}$ alkyl); $R_2$ and $R_4$ are bonded together to form a 4- to 7-membered saturated or unsaturated monoheterocyclic ring;

(ii) when n is 0, $R_2$ and $R_4$ are each independently selected from the group consisting of hydrogen, halogen, hydroxy, alkoxy, and $C_{1-8}$ alkyl (preferably $C_{1-6}$ alkyl, more preferably $C_{1-3}$ alkyl); $R_1$ and $R_3$ are bonded together to form a 4- to 7-membered saturated or unsaturated monoheterocyclic ring;

(iii) when n is 0, $R_2$ is selected from the group consisting of hydrogen, halogen, and $C_{1-8}$ alkyl (preferably $C_{1-6}$ alkyl, more preferably $C_{1-3}$ alkyl); $R_3$ is bonded with $R_1$ and $R_4$ to form a bridged heterocycle; or $R_3$ is selected from the group consisting of hydrogen, halogen, and $C_{1-8}$ alkyl (preferably $C_{1-6}$ alkyl, more preferably $C_{1-3}$ alkyl); $R_2$ is bonded with $R_1$ and $R_4$ to form a bridged heterocycle;

(iv) when n is 1, $R_2$ and $R_3$ are each independently selected from the group consisting of hydrogen, halogen, hydroxy, alkoxy, and $C_{1-8}$ alkyl (preferably $C_{1-6}$ alkyl, more preferably $C_{1-3}$ alkyl); $R_a$ and $R_1$ are bonded and $R_b$ and $R_4$ are bonded which together form a spiro heterocycle;

(v) when n is 1, $R_2$, $R_3$ and $R_b$ are each independently selected from the group consisting of hydrogen, halogen, hydroxy, alkoxy, and $C_{1-8}$ alkyl (preferably $C_{1-6}$ alkyl, more preferably $C_{1-3}$ alkyl); $R_a$ is bonded with $R_1$ and $R_4$ respectively together to form a bridged heterocycle;

(vi) when n is 1, $R_1$, $R_3$, $R_a$ and $R_b$ are each independently selected from the group consisting of hydrogen, halogen, hydroxy, alkoxy, and $C_{1-8}$ alkyl (preferably $C_{1-6}$ alkyl, more preferably $C_{1-3}$ alkyl); $R_2$ and $R_4$ are bonded together to form a 5- to 7-membered saturated or unsaturated monoheterocyclic ring;

the alkyl, cycloalkyl, alkoxy, aryl, saturated or unsaturated monoheterocyclic ring, monocyclic heteroaryl ring, bicyclic heteroaryl ring, spiro heterocyclic ring, bridged heterocyclic ring are unsubstituted or substituted with 1, 2 or 3 substituents selected from the group consisting of hydroxymethyl, hydroxyethyl, hydroxy, carboxyl, halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), $NR_{a0}R_{b0}$, —C(O)OC$_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), —SO$_2$C$_{1-8}$ alkyl (preferably —SO$_2$C$_{1-6}$ alkyl, more preferably —SO$_2$C$_{1-3}$ alkyl), $C_{6-10}$ aryl (preferably phenyl), 5- to 6-membered monocyclic heteroaryl and —Y-L; wherein Y is (CH$_2$)$_q$ or C(O), L is a 4- to 6-membered saturated monoheterocyclic ring or a 5- to 6-membered monocyclic heteroaryl ring, p and q are each independently 1, 2 or 3, and $R_{a0}$ and $R_{b0}$ are each independently selected from the group consisting of hydrogen, acetyl, $C_{1-8}$ alkyl (preferably $C_{1-6}$ alkyl, more preferably $C_{1-3}$ alkyl), and $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

In another preferred embodiment, the 4- to 6-membered saturated monoheterocyclic ring in the substituents is unsubstituted or substituted with 1, 2 or 3 groups selected from the group consisting of halogen, hydroxy, $C_{1-6}$ alkyl, O=, $NR_{a0}R_{b0}$, hydroxymethyl, hydroxyethyl, carboxyl, —C(O)OC$_{1-6}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

In another preferred embodiment, the 4- to 7-membered or 5- to 7-membered saturated or unsaturated monoheterocyclic ring is selected from the group consisting of azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide and tetrahydropyran.

In another preferred embodiment, the 5- to 6-membered monocyclic heteroaryl ring is selected from the group consisting of a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, and a pyrazine ring.

In another preferred embodiment, the bridged heterocyclic ring is a bicyclic bridged heterocyclic ring containing 4-, 5- or 6-membered rings.

In another preferred embodiment, the spiro heterocyclic ring is a bicyclic spiro heterocyclic ring containing 4-, 5- or 6-membered rings.

In another preferred embodiment, when n is 0, $R_2$ and $R_4$ are bonded together to form a 4- to 7-membered saturated monoheterocyclic ring containing only nitrogen.

In another preferred embodiment, when n is 0, $R_1$ and $R_3$ are bonded together to form a 4- to 7-membered saturated monoheterocyclic ring containing only nitrogen.

In another preferred embodiment, when n is 0, $R_3$ is bonded with $R_1$ and $R_4$ to form a bicyclic bridged heterocyclic ring containing only nitrogen, or $R_2$ is bonded with $R_1$ and $R_4$ to form a bicyclic bridged heterocyclic ring containing only nitrogen.

In another preferred embodiment, when n is 1, $R_a$ and $R_1$ are bonded and $R_b$ and $R_4$ are bonded together to form a bicyclic spiro heterocycle containing only nitrogen.

In another preferred embodiment, when n is 1, $R_a$ is bonded with $R_1$ and $R_4$ respectively together to form a bicyclic bridged heterocycle containing only nitrogen.

In another preferred embodiment, when n is 1, $R_2$ and $R_4$ are bonded together to form a 5- to 7-membered saturated monoheterocyclic ring containing only nitrogen.

In another preferred embodiment, $R_5$ and $R_6$ are hydrogen.

In another preferred embodiment, Z is N or $CR_{b1}$; wherein $R_{b1}$ is hydrogen or halogen (preferably fluorine, chlorine, bromine).

In another preferred embodiment, Z is $CR_{b1}$; wherein $R_{b1}$ is halogen (preferably fluorine, chlorine, bromine).

In another preferred embodiment, X is a bond or NH.

In another preferred embodiment,

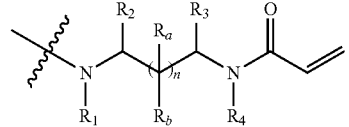

is a structure represented by formula (A), (B) or (C):

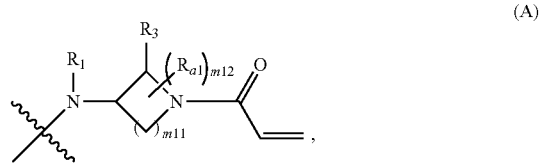

(A)

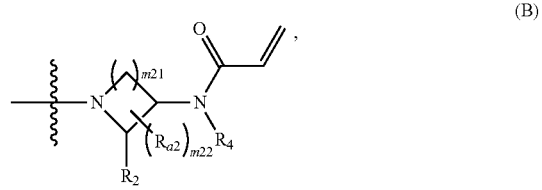

(B)

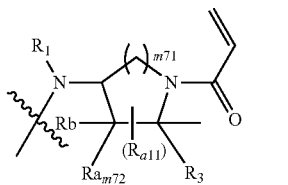
(C)

wherein, m11 and m21 are each independently 1, 2, 3 or 4; m71 is 1, 2 or 3;

m12 and m22 are each independently 0, 1, 2, 3 or 4; m72 is 0, 1, 2 or 3;

$R_{a1}$, $R_{a2}$, and $R_{a11}$ are each independently selected from the group consisting of halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferred a $C_{1-6}$ alkoxy-substituted $C_{1-6}$ alkyl, more preferably a $C_{1-3}$ alkoxy-substituted $C_{1-3}$ alkyl), and $C_{3-8}$ cycloalkyl (preferably $C_{3-6}$ cycloalkyl);

$R_1$, $R_2$, $R_3$, $R_4$, $R_a$, and $R_b$ are as defined in claim 1.

In another preferred embodiment,

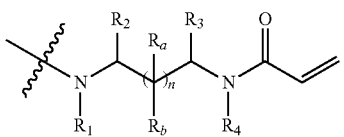

is a structure represented by formula (D), (E) or (F):

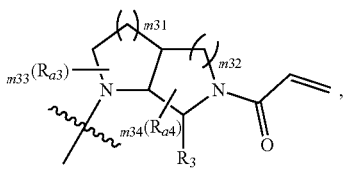
(D)

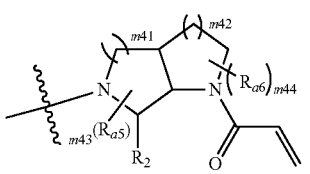
(E)

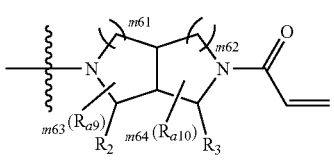
(F)

wherein, m31, m32, m41, m42, m61 and m62 are each independently 0, 1, 2, or 3;

m33, m34, m43, m44, m63 and m64 are each independently 0, 1, 2, or 3;

$R_{a3}$, $R_{a4}$, $R_{a5}$, $R_{a6}$, $R_{a9}$ and $R_{a10}$ are each independently selected from the group consisting of halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferred a $C_{1-6}$ alkoxy-substituted $C_{1-6}$ alkyl, more preferably a $C_{1-3}$ alkoxy-substituted $C_{1-3}$ alkyl), and $C_{3-8}$ cycloalkyl (preferably $C_{3-6}$ cycloalkyl);

$R_2$, $R_3$ are as defined in claim 1.

In another preferred embodiment,

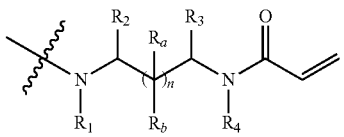

is a structure represented by formula (G):

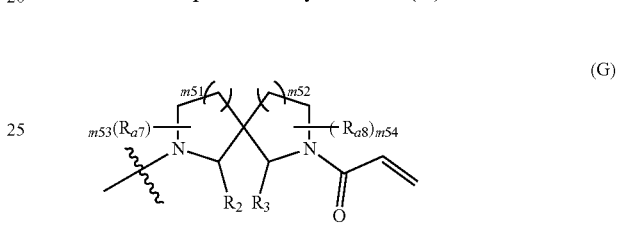
(G)

wherein, m51 and m52 are each independently 0, 1, 2, or 3;

m53 and m54 are each independently 0, 1, 2, 3 or 4;

$R_{a7}$ and $R_{a8}$ are each independently selected from the group consisting of halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferred a $C_{1-6}$ alkoxy-substituted $C_{1-6}$ alkyl, more preferably a $C_{1-3}$ alkoxy-substituted $C_{1-3}$ alkyl), and $C_{3-8}$ cycloalkyl (preferably $C_{3-6}$ cycloalkyl);

$R_2$, $R_3$ are as defined in claim 1.

In another preferred embodiment, m11 is 1, 2, 3 or 4; $R_3$ is selected from the group consisting of hydrogen, halogen and $C_{1-8}$ alkyl (preferably $C_{1-6}$ alkyl, more preferably $C_{1-3}$ alkyl); m12 is 0.

In another preferred embodiment, m11 is 1, 2, 3 or 4; $R_3$ is hydrogen; m12 is 1, 2, 3 or 4; $R_{a1}$ is halogen or $C_{1-8}$ alkyl (preferably $C_{1-6}$ alkyl, more preferably $C_{1-3}$ alkyl).

In another preferred embodiment, m21 is 1, 2, 3 or 4; $R_2$ is hydrogen; $R_4$ is halogen or $C_{1-8}$ alkyl (preferably $C_{1-6}$ alkyl, more preferably $C_{1-3}$ alkyl); m22 is 0, 1, 2, 3 or 4; $R_{a2}$ is halogen or $C_{1-8}$ alkyl (preferably $C_{1-6}$ alkyl, more preferably $C_{1-3}$ alkyl).

In another preferred embodiment, m21 is 1, 2, 3 or 4; $R_2$ and $R_4$ are hydrogen; m22 is 0.

In another preferred embodiment, m71 is 1, 2, or 3; $R_a$ and $R_b$ are hydrogen; m72 is 0.

In another preferred embodiment, m31 and m32 are each independently 0, 1, 2, or 3; m33 and m34 are 0; $R_3$ is selected from the group consisting of hydrogen, halogen and $C_{1-8}$ alkyl (preferably $C_{1-6}$ alkyl, more preferably $C_{1-3}$ alkyl).

In another preferred embodiment, m31 and m32 are each independently 1, or 2; m33 and m34 are 0; $R_3$ is hydrogen.

In another preferred embodiment, m31 is 1; m32 is 1 or 2; m33 and m34 are 0; R₃ is hydrogen.

In another preferred embodiment, m41 and m42 are each independently 0, 1, 2, or 3; m43 and m44 are 0; R₂ is selected from the group consisting of hydrogen, halogen and C$_{1-8}$ alkyl (preferably C$_{1-6}$ alkyl, more preferably C$_{1-3}$ alkyl).

In another preferred embodiment, m41 and m42 are 1; m43 and m44 are 0; R₂ is hydrogen.

In another preferred embodiment, m61 and m62 are each independently 0, 1, 2, or 3; m63 and m64 are 0; R₂ and R₃ are each independently selected from the group consisting of hydrogen, halogen and C$_{1-8}$ alkyl (preferably C$_{1-6}$ alkyl, more preferably C$_{1-3}$ alkyl).

In another preferred embodiment, m61 and m62 are 1; m63 and m64 are 0; and R₂ and R₃ are hydrogen.

In another preferred embodiment, m51 and m52 are each independently 1 or 2; m53 and m54 are 0; and R₂ and R₃ are hydrogen.

In another preferred embodiment, X is a bond or NR$_{a1}$, wherein R$_{a1}$ is hydrogen or C$_{1-3}$ alkyl.

In another preferred embodiment, A is C$_{6-10}$ aryl (preferably phenyl), or a 5- to 6-membered monocyclic heteroaryl ring; A is optionally substituted by 1, 2 or 3 substituents selected from the group A1, and the optional substitution means that the hydrogen on the ring atoms (including carbon atoms and N atoms) is replaced by a substituent.

In another preferred embodiment, X is NH; A is C$_{6-10}$ aryl (preferably phenyl), or a 5- to 6-membered monocyclic heteroaryl ring; A is optionally substituted by 1, 2 or 3 substituents selected from the group A1, and the optional substitution means that the hydrogen on the ring atoms (including carbon atoms and N atoms) is replaced by a substituent.

In another preferred embodiment, X is a bond; A is a 5- to 6-membered monocyclic heteroaryl ring; A is optionally substituted by 1, 2 or 3 substituents selected from the group A1, and the optional substitution means that the hydrogen on the ring atoms (including carbon atoms and N atoms) is replaced by a substituent.

In another preferred embodiment, the 5- to 6-membered monocyclic heteroaryl ring is selected from the group consisting of a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, and a pyrazine ring.

In another preferred embodiment, the 5- to 6-membered monocyclic heteroaryl ring is selected from the group consisting of

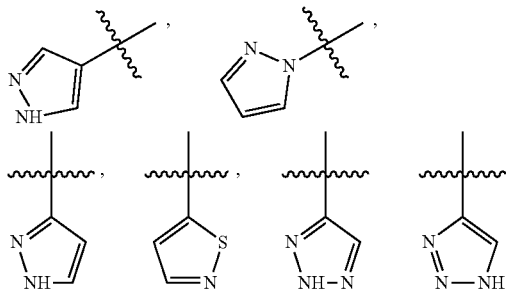

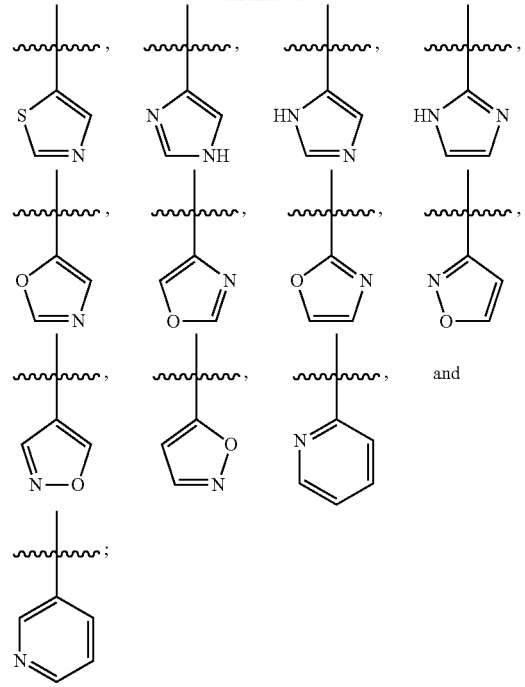

the 5- to 6-membered monocyclic heteroaryl ring is optionally substituted by 1, 2 or 3 substituents selected from the group A1, the optional substitution means that the hydrogen on the ring atoms (including carbon atoms and N atoms) is replaced by a substituent.

In another preferred embodiment, X is NH, and A is a structure selected from the group B1.

In another preferred embodiment, X is a bond, and A is a structure selected from the group B1 or B2.

In another preferred embodiment, X is NH; A is C$_{6-10}$ aryl (preferably phenyl), or a 5- to 6-membered monocyclic heteroaryl ring; A is optionally substituted by 1, 2 or 3 substituents selected from the group A1, and the optional substitution means that the hydrogen on the ring atoms (including carbon atoms and N atoms) is replaced by a substituent;

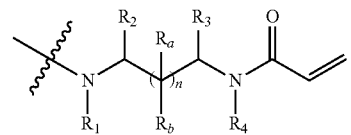

is a structure represented by formula (A); wherein the groups in formula (A) are defined as in claim 1;

R₁ is hydrogen or C$_{1-8}$ alkyl (preferably C$_{1-6}$ alkyl, more preferably C$_{1-3}$ alkyl).

In another preferred embodiment, X is NH; A is a structure selected from the group B1;

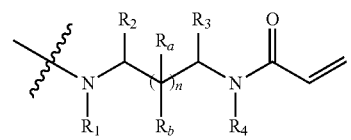

is a structure represented by formula (A); wherein the groups in formula (A) are defined as in claim 1;

$R_1$ is hydrogen or $C_{1-8}$ alkyl (preferably $C_{1-6}$ alkyl, more preferably $C_{1-3}$ alkyl).

In another preferred embodiment, X is a bond; A is a 5- to 6-membered monocyclic heteroaryl ring; A is optionally substituted by 1, 2 or 3 substituents selected from the group A1, and the optional substitution means that the hydrogen on the ring atoms (including carbon atoms and N atoms) is replaced by a substituent;

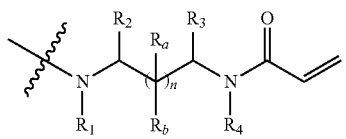

is a structure represented by formula (A); wherein the groups in formula (A) are defined as in claim 1;

$R_1$ is hydrogen or $C_{1-8}$ alkyl (preferably $C_{1-6}$ alkyl, more preferably $C_{1-3}$ alkyl).

In another preferred embodiment, X is a bond; A is a structure selected from the group B1 or B2:

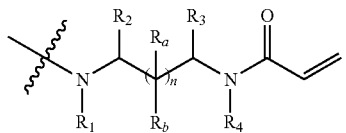

is a structure represented by formula (A); wherein the groups in formula (A) are defined as in claim 1;

$R_1$ is hydrogen or $C_{1-8}$ alkyl, preferably $R_1$ is $C_{1-8}$ alkyl (preferably $C_{1-6}$ alkyl, more preferably $C_{1-3}$ alkyl).

In another preferred embodiment, m1 1 is 3.

In another preferred embodiment, the formula (D), (E), (F) or (G) is selected from the group consisting of:

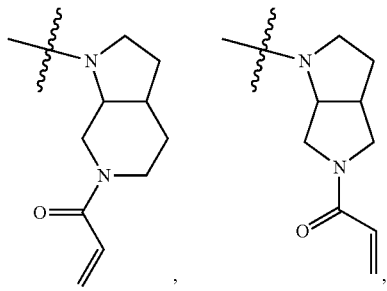

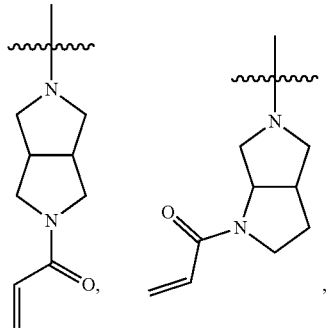

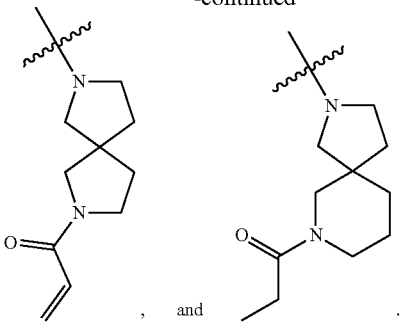

, and .

In another preferred embodiment, the formula (A) is a structure selected from the group C1.

In another preferred embodiment, the structure of group C1 is:

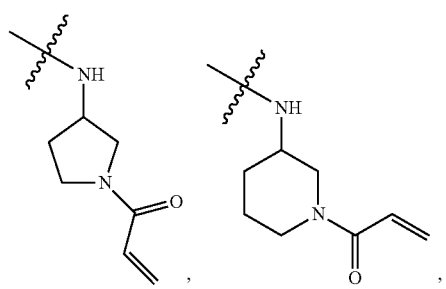

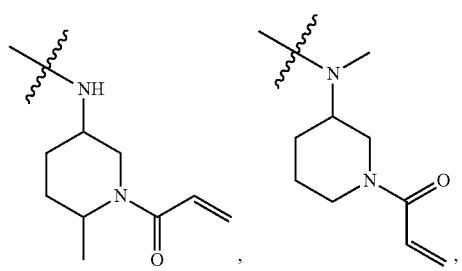

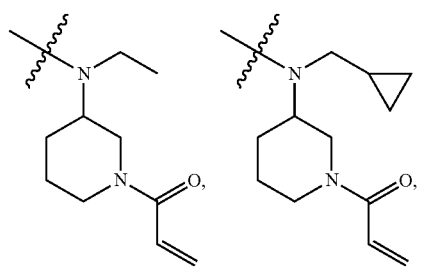

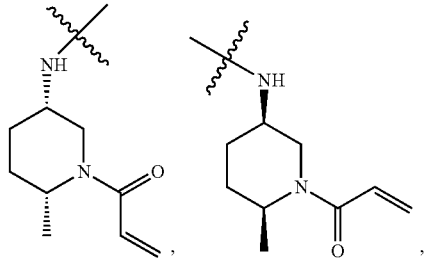

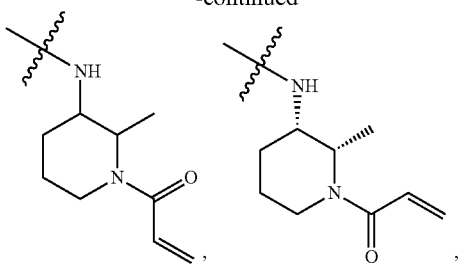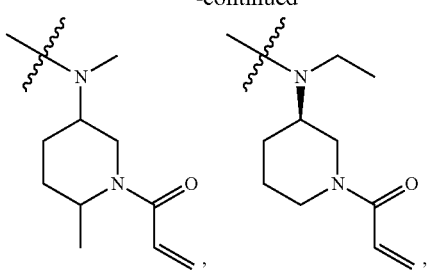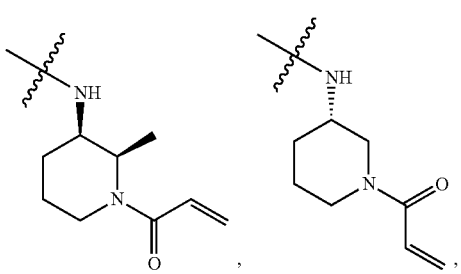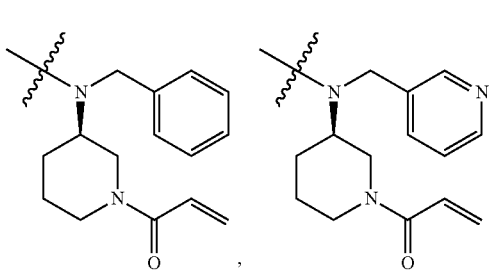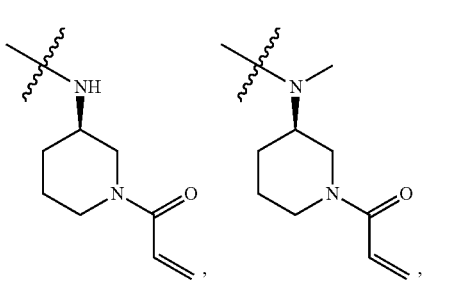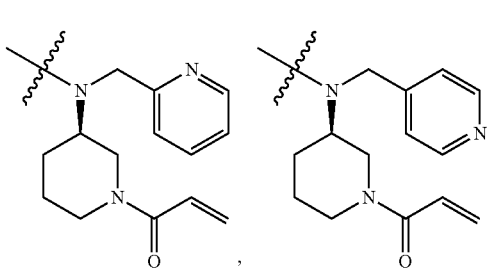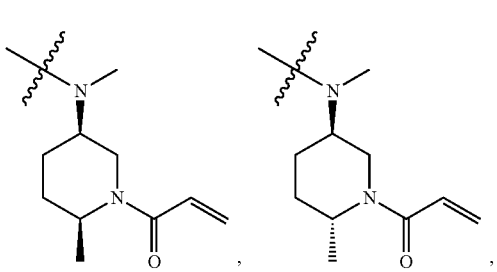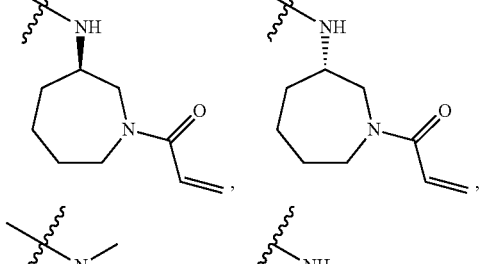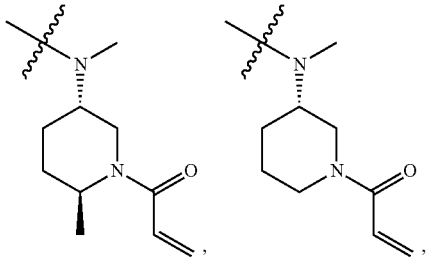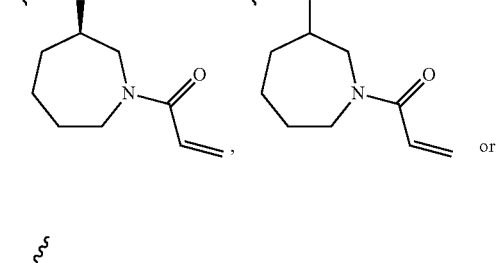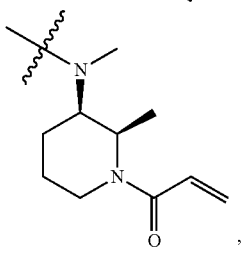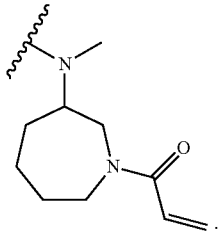

In another preferred embodiment, the formula (B) is selected from the group consisting of:

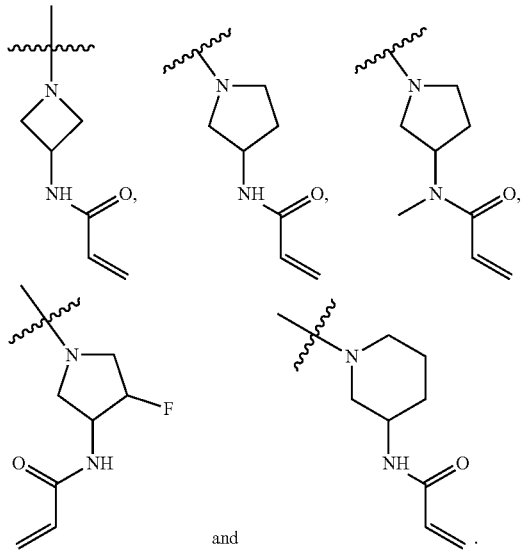

In another preferred embodiment, the formula (C) is selected from:

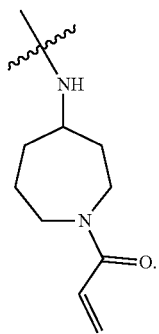 [SMILES: *NC1CCCN(C(=O)C=C)CC1]

In the second aspect of the present disclosure, a compound of formula (II), or a pharmaceutically acceptable salt, stereoisomer, solvate or prodrug thereof is provided:

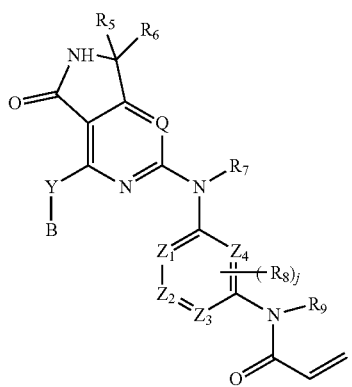

wherein Y is selected from the group consisting of a bond, $NR_{a1}$, S, SO, $SO_2$ and O; wherein $R_{a1}$ is selected from the group consisting of hydrogen, hydroxy and $C_{1-8}$ alkyl (preferably $C_{1-6}$ alkyl, more preferably $C_{1-3}$ alkyl);

B is selected from the group consisting of $C_{6-10}$ aryl (preferably phenyl), a 4- to 7-membered saturated or unsaturated monoheterocyclic ring, a 5- to 6-membered monocyclic heteroaryl ring, and an 8- to 10-membered bicyclic heteroaryl ring;

Q is N or $CR_{b1}$; wherein $R_{b1}$ is selected from the group consisting of hydrogen, halogen (preferably fluorine, chlorine, bromine), cyano, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) and $C_{3-8}$ cycloalkoxy (preferably $C_{3-6}$ cycloalkoxy);

three of $Z_1$, $Z_2$, $Z_3$ and $Z_4$ are CH, and one of $Z_1$, $Z_2$, $Z_3$ and $Z_4$ is N; or $Z_1$, $Z_2$, $Z_3$ and $Z_4$ are CH;

$R_5$ and $R_6$ are each independently selected from the group consisting of hydrogen, halogen (preferably fluorine, chlorine, bromine), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) and $C_{3-8}$ cycloalkoxy (preferably $C_{3-6}$ cycloalkoxy);

$R_7$ and $R_9$ are each independently selected from the group consisting of hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl) and $C_{3-8}$ cycloalkyl (preferably $C_{3-6}$ cycloalkyl);

$R_8$ is selected from the group consisting of hydrogen, halogen, cyano, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl) and $NR_{a0}R_{b0}$; wherein $R_{a0}$ and $R_{b0}$ are each independently selected from the group consisting of hydrogen, acetyl, $C_{1-8}$ alkyl (preferably $C_{1-6}$ alkyl, more preferably $C_{1-3}$ alkyl), and $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl);

j is 0, 1, 2, 3 or 4; and the alkyl, cycloalkyl, alkoxy, cycloalkoxy, aryl, saturated or unsaturated monoheterocyclic ring, monocyclic heteroaryl ring, bicyclic heteroaryl ring are unsubstituted or substituted with 1, 2 or 3 substituents selected from the group consisting of halogen, hydroxymethyl, hydroxyethyl, hydroxy, carboxyl, $—O(CH_2)_pOC_{1-8}$ alkyl, $—O(CH_2)_pOH$, $—(CH_2)_pOC_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), $NR_{a0}R_{b0}$, $—C(O)OC_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), $—SO_2C_{1-8}$ alkyl (preferably $—SO_2C_{1-6}$ alkyl, more preferably $—SO_2C_{1-3}$ alkyl), $C_{6-10}$ aryl (preferably phenyl), 5- to 6-membered monocyclic heteroaryl and —Y-L; wherein Y is $(CH_2)_q$ or C(O), L is a 4- to 6-membered saturated monoheterocyclic ring or a 5- to 6-membered monocyclic heteroaryl ring, q is 1, 2 or 3; and $R_{a0}$ and $R_{b0}$ are each independently selected from the group consisting of hydrogen, acetyl, $C_{1-8}$ alkyl (preferably $C_{1-6}$ alkyl, more preferably $C_{1-3}$ alkyl), and $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

In another preferred embodiment, Y is a bond or $NR_{a1}$; wherein $R_{a1}$ is hydrogen or $C_{1-3}$ alkyl.

In another preferred embodiment, B is phenyl or a pyrazole ring.

In another preferred embodiment, Y is a bond; B is a 5- to 6-membered monocyclic heteroaryl ring; and the 5- to 6-membered monocyclic heteroaryl ring is optionally substituted by 1, 2 or 3 substituents selected from the group A1.

In another preferred embodiment, Y is a bond; and B is a structure selected from the group B2.

In another preferred embodiment, Y is a bond; B is a pyrazole ring; and the pyrazole ring is optionally substituted by 1, 2 or 3 substituents selected from the group A1.

In another preferred embodiment, Y is $NR_{a1}$; wherein $R_{a1}$ is hydrogen or $C_{1-3}$ alkyl; B is phenyl or a 5- to 6-membered monocyclic heteroaryl ring; B is optionally substituted by 1, 2 or 3 substituents selected from the group A1, and the optional substitution means that the hydrogen on the ring atoms (including carbon atoms and N atoms) is replaced by a substituent.

In another preferred embodiment, Y is $NR_{a1}$; wherein $R_{a1}$ is hydrogen or $C_{1-3}$ alkyl; B is phenyl or a pyrazole ring; and the phenyl or pyrazole ring is optionally substituted by 1, 2 or 3 substituents selected from the group A1.

In another preferred embodiment, Y is $NR_{a1}$; wherein $R_{a1}$ is hydrogen or $C_{1-3}$ alkyl; and B is a structure selected from the group B1.

In another preferred embodiment, $R_7$ and $R_9$ are each independently selected from the group consisting of hydrogen, $C_{1-3}$ alkyl, halogenated $C_{1-3}$ alkyl and $C_{3-6}$ cycloalkyl.

In another preferred embodiment, the substituent of the group A1 is selected from the group consisting of halogen, —$O(CH_2)_pOC_{1-8}$ alkyl, —$O(CH_2)_pOH$, —$(CH_2)_pOC_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), hydroxymethyl, hydroxyethyl, hydroxy, carboxyl, $NR_{a0}R_{b0}$, —$C(O)OC_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), —$SO_2C_{1-8}$ alkyl (preferably —$SO_2C_{1-6}$ alkyl, more preferably —$SO_2C_{1-3}$ alkyl), $C_{6-10}$ aryl (preferably phenyl), 5- to 6-membered monocyclic heteroaryl and —Y-L; wherein Y is $(CH_2)_q$ or C(O), L is a 4- to 6-membered saturated monoheterocyclic ring, p and q are each independently 1, 2 or 3, and $R_{a0}$ and $R_{b0}$ are each independently selected from the group consisting of hydrogen, acetyl, $C_{1-8}$ alkyl (preferably $C_{1-6}$ alkyl, more preferably $C_{1-3}$ alkyl), and $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

In another preferred embodiment, the 4- to 6-membered saturated monoheterocycle in the substituents of the group A1 is selected from the group consisting of azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide and tetrahydropyran.

In another preferred embodiment, the 4- to 6-membered saturated monoheterocyclic ring in the substituents of the group A1 is unsubstituted or substituted with 1, 2 or 3 groups selected from the group consisting of halogen, hydroxy, $C_{1-3}$ alkyl, O=, $NR_{a0}R_{b0}$, hydroxymethyl, hydroxyethyl, hydroxypropyl, carboxyl, —$C(O)OC_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

In another preferred embodiment, the substituent of the group A1 is selected from the group consisting of fluorine, chlorine, bromine, hydroxymethyl, hydroxyethyl, hydroxy, carboxyl, —$O(CH_2)_pOC_{1-3}$ alkyl, —$O(CH_2)_pOH$, —$(CH_2)_pOC_{1-3}$ alkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, methyl, ethyl, n-propyl, isopropyl, cyclopropyl, monochloroethyl, dichloromethyl, 1,2-dichloroethyl, monobromoethyl, monofluoromethyl, difluoromethyl, trifluoromethyl, monofluoroethyl, difluoroethyl, trifluoroethyl, monochlorocyclopropyl, dichlorocyclopropyl, trichlorocyclopropyl, monofluorocyclopropyl, difluorocyclopropyl, trifluorocyclopropyl, $NR_{a0}R_{b0}$, —$C(O)OC_{1-3}$ alkyl, acetyl, methoxy, ethoxy, propoxy, isopropoxy, trifluoromethoxy, trifluoroethoxy, monofluoromethoxy, monofluoroethoxy, difluoromethoxy, difluoroethoxy, phenyl, pyridyl and —Y-L; wherein Y is $(CH_2)_q$ or C(O), L is selected from the group consisting of azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, and tetrahydropyran, p is 1, 2 or 3, q is 1, and $R_{a0}$, $R_{b0}$ are each independently selected from the group consisting of hydrogen, acetyl, methyl, ethyl, n-propyl, isopropyl, and methoxy-substituted $C_{1-3}$ alkyl.

In another preferred embodiment, the structure of group B1 is:

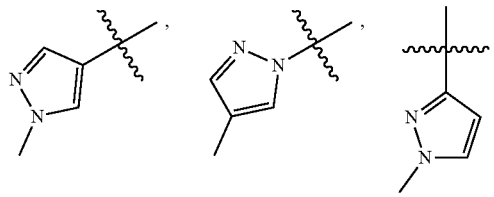

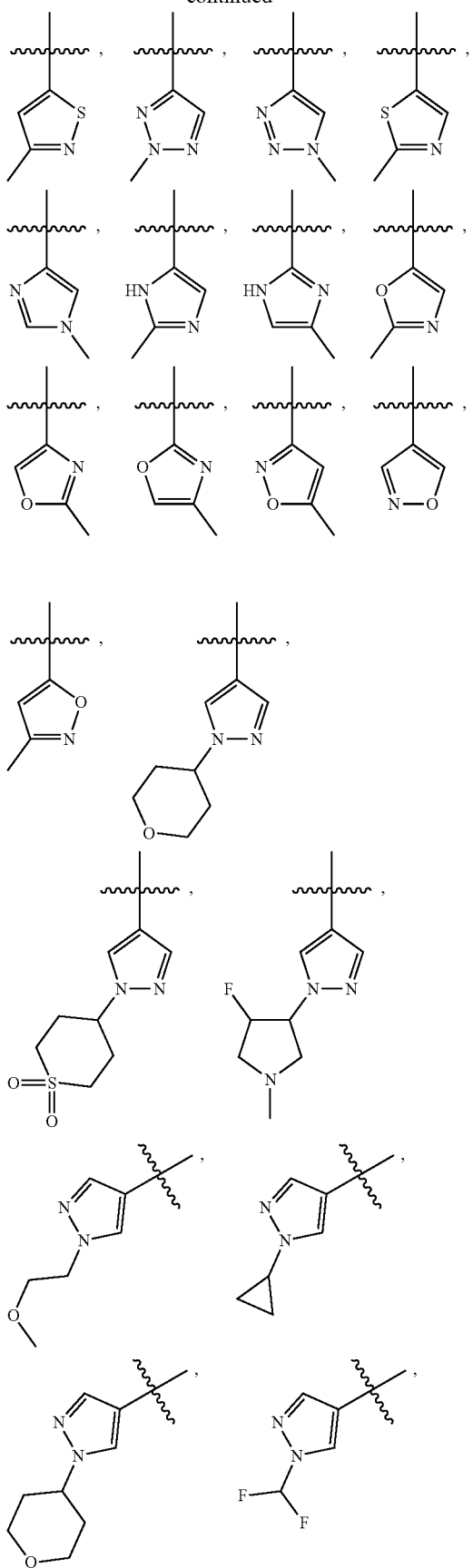
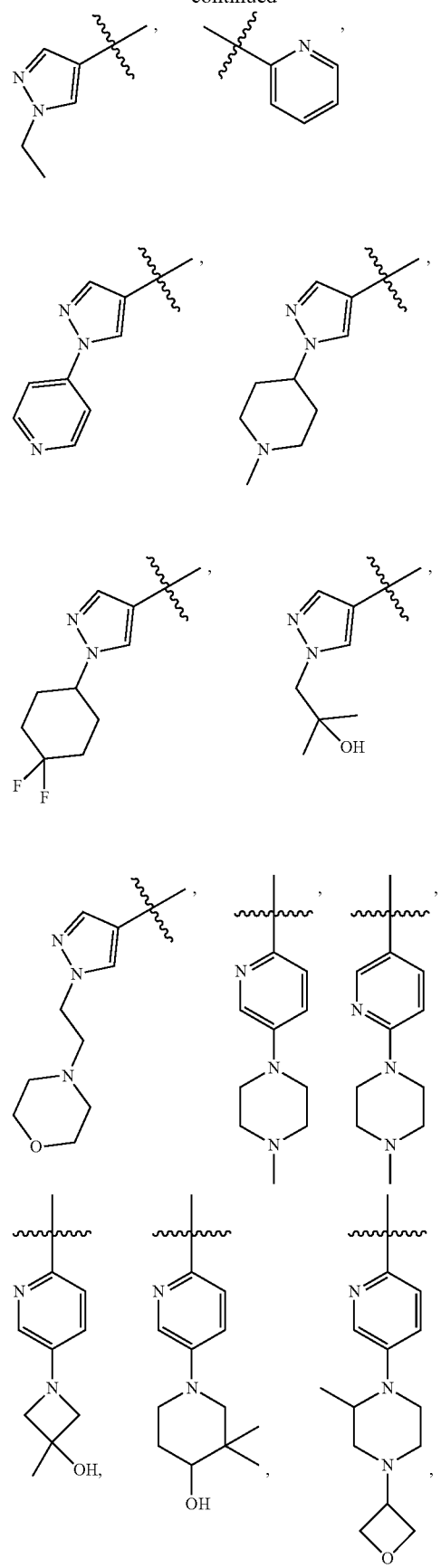

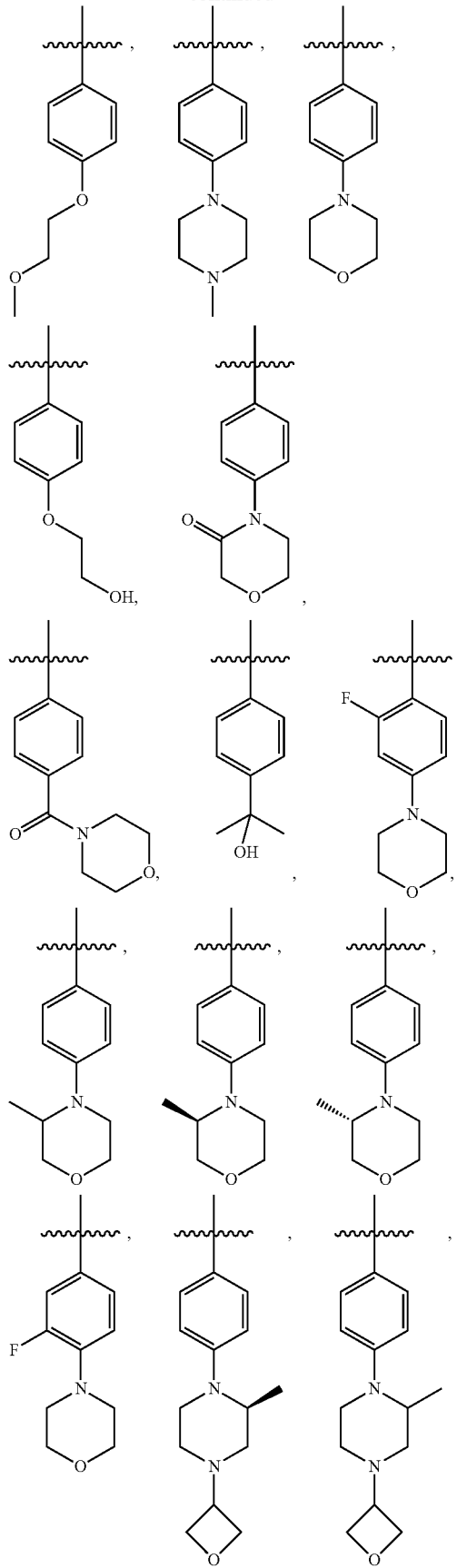
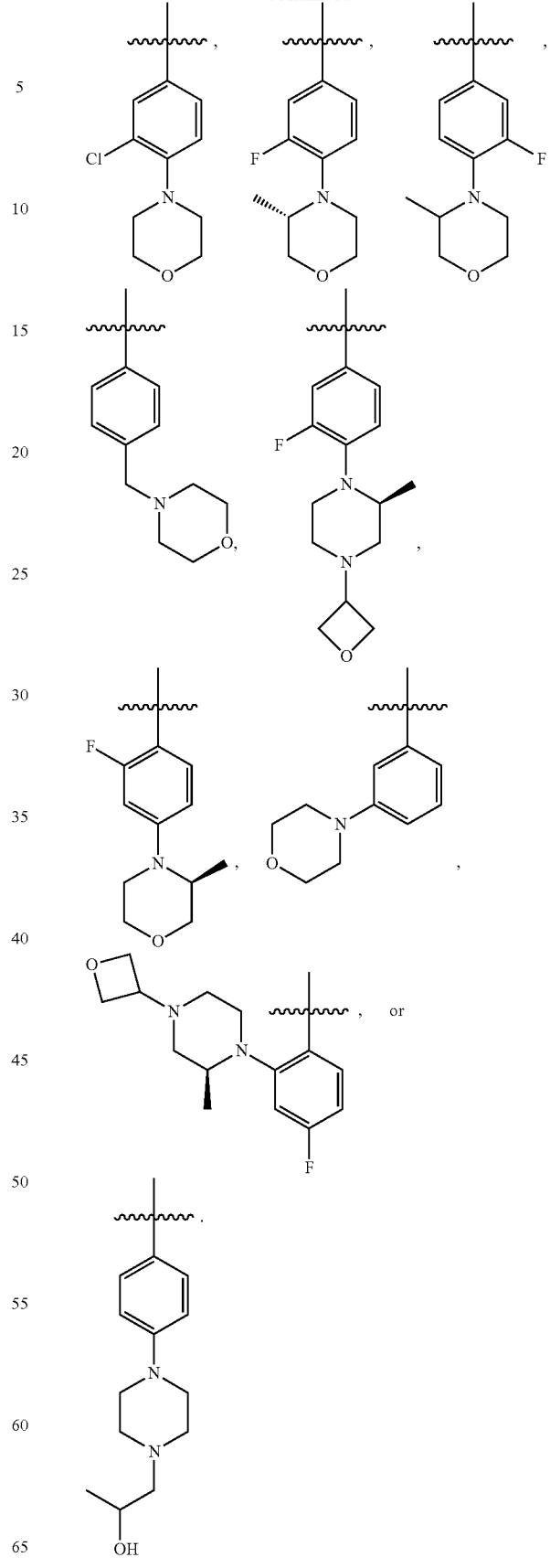

In another preferred embodiment, the structure of group B2 is:
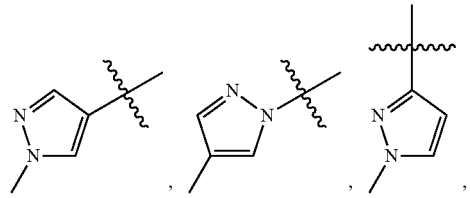
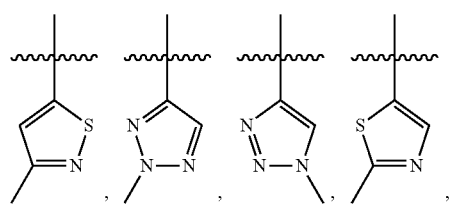
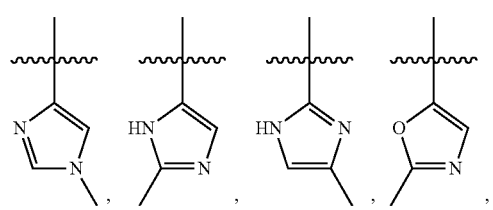
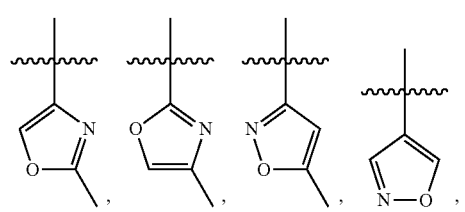
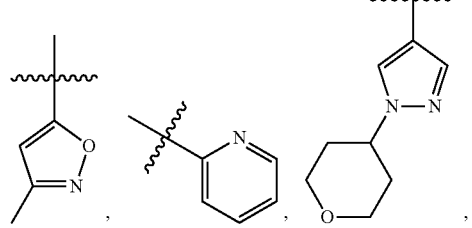
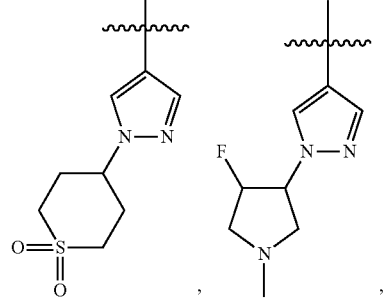
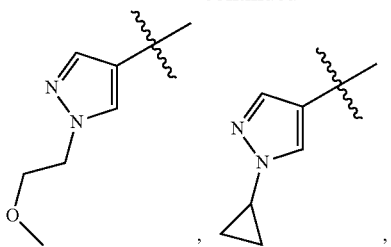
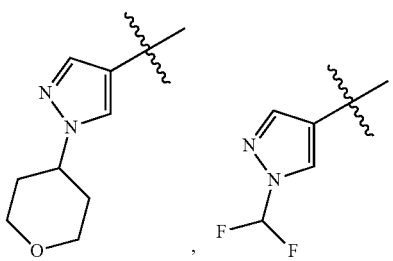
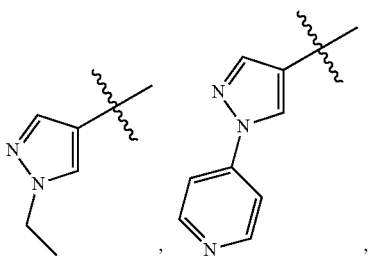
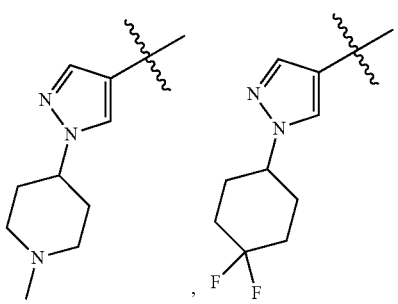
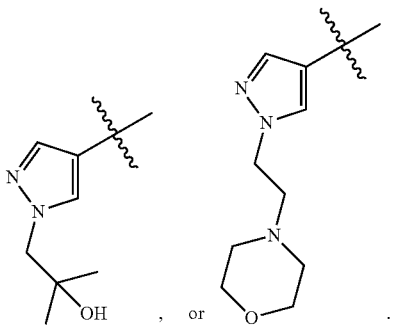
In another preferred embodiment, the compound of formula (I) is a structure selected from the group D1.

In another preferred embodiment, the structure of group D1 is:
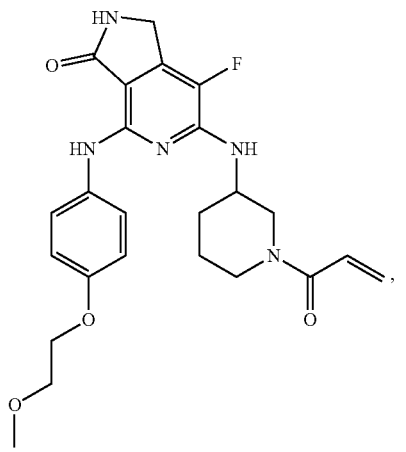
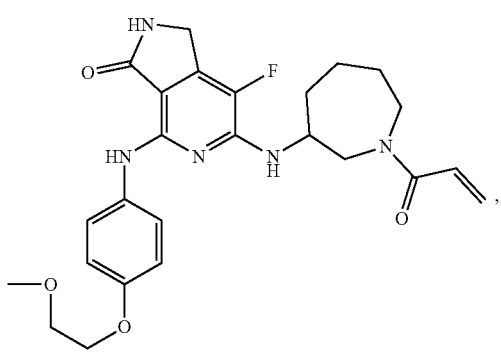
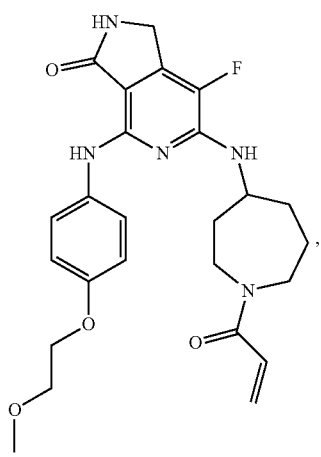
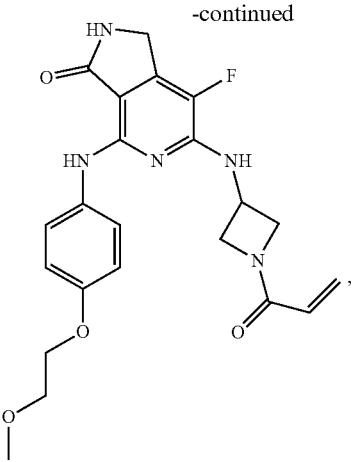
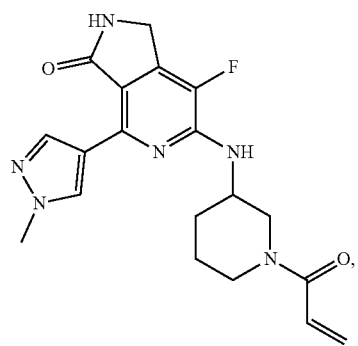
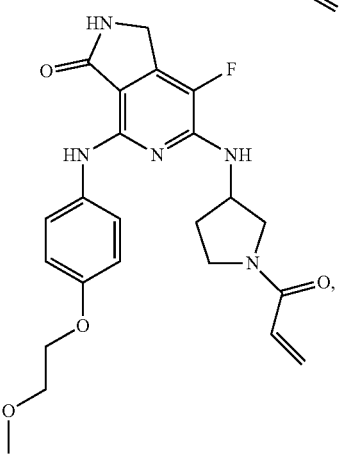
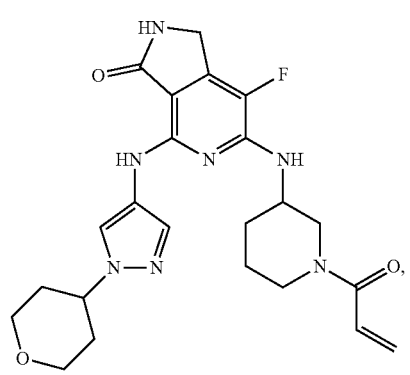

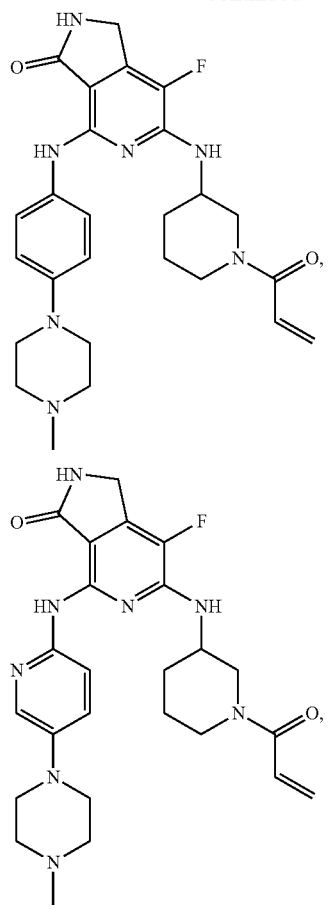
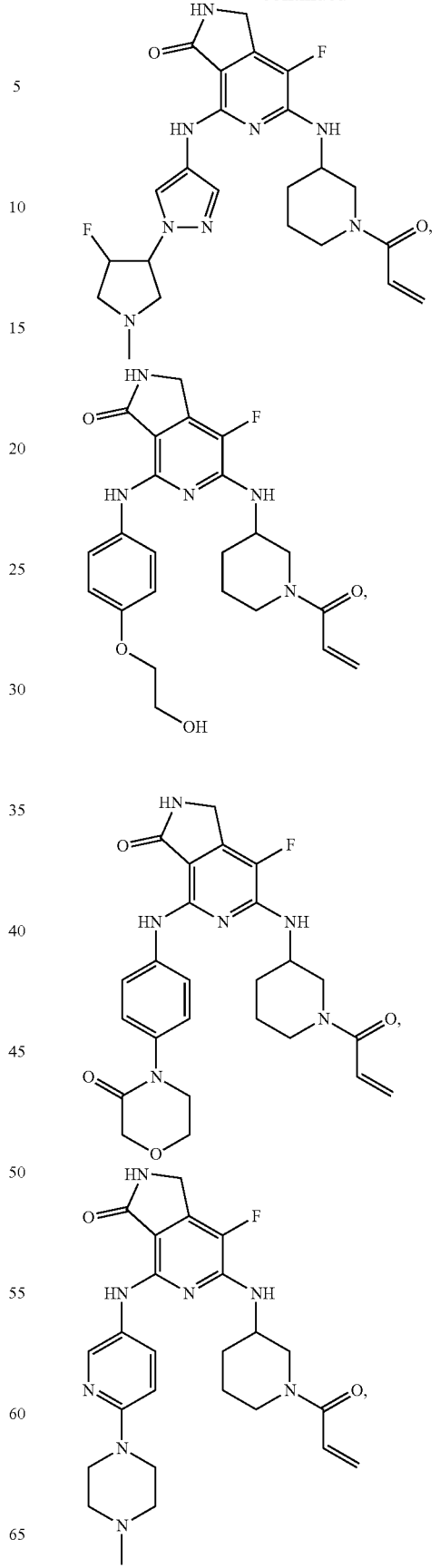

27
-continued
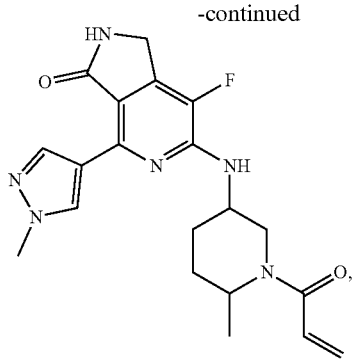
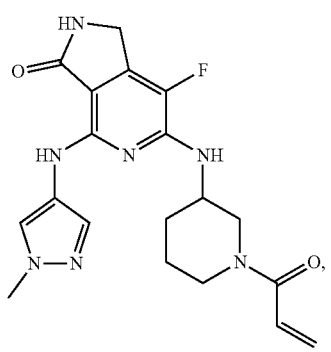
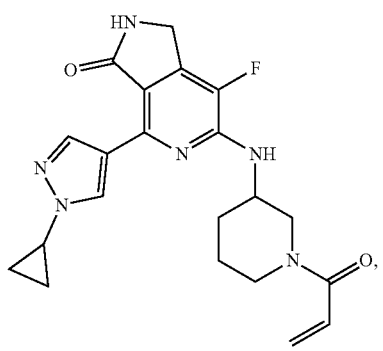
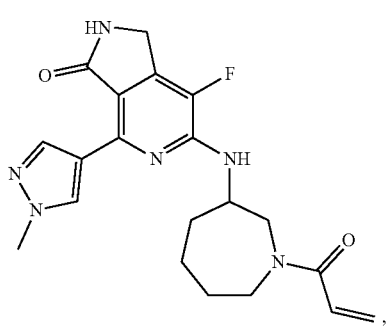
28
-continued
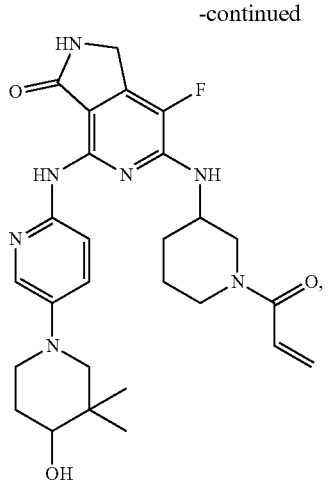
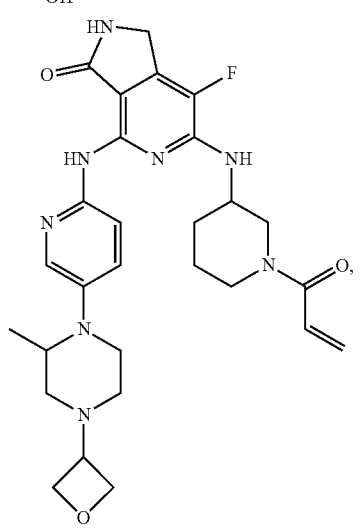
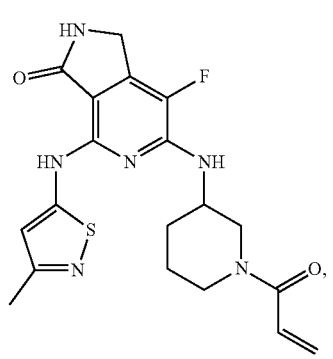
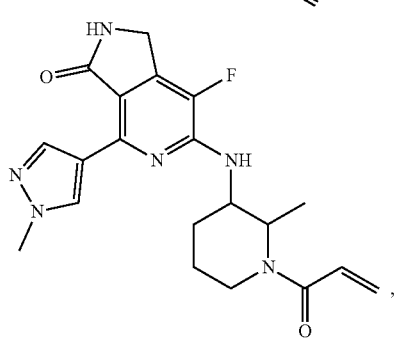

29
-continued
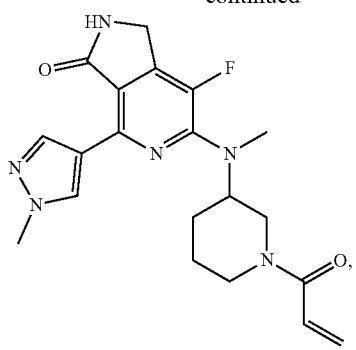
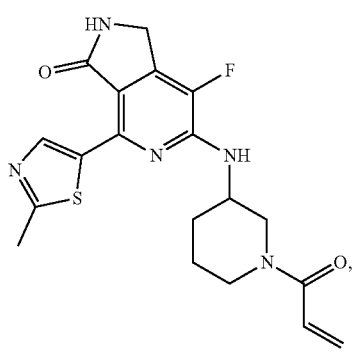
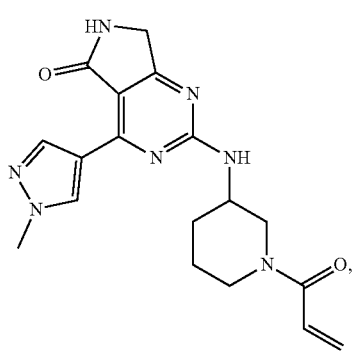
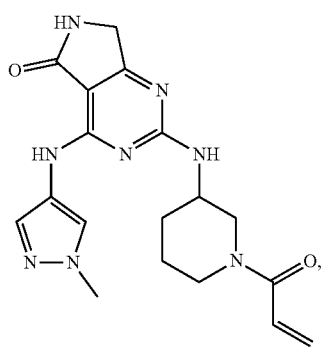
30
-continued
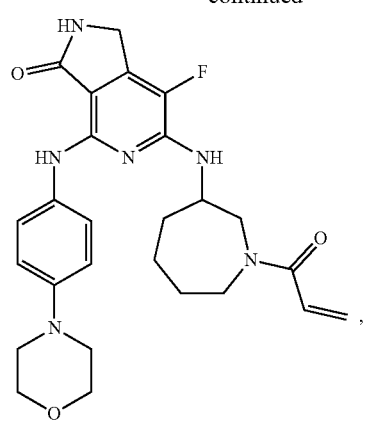
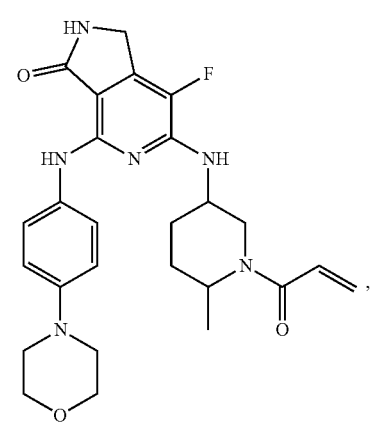
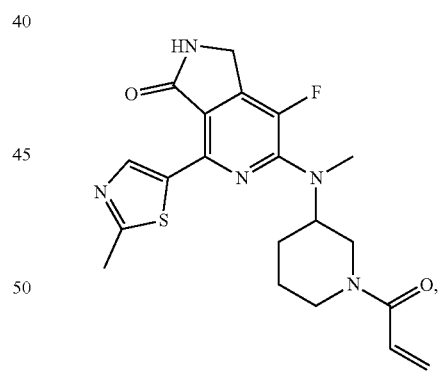
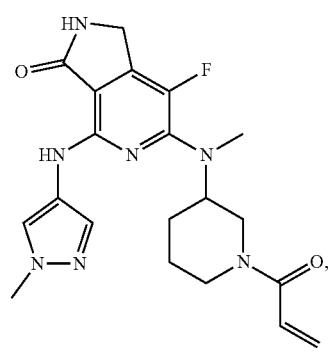

31
-continued
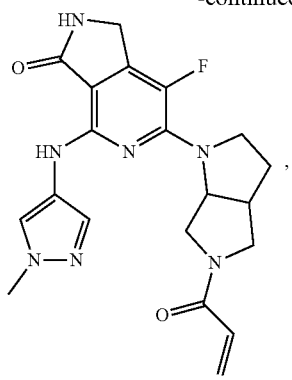
32
-continued
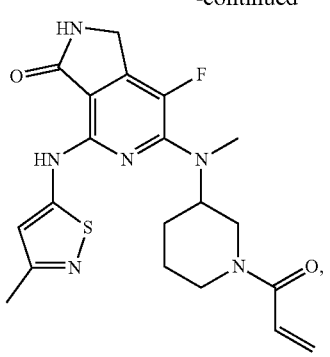
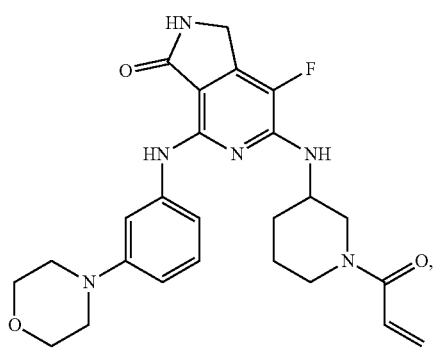
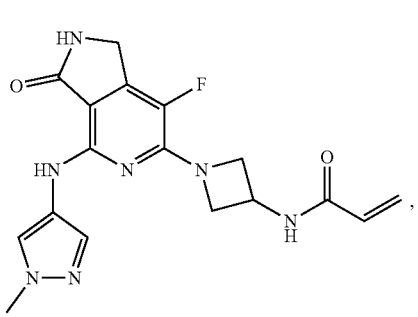
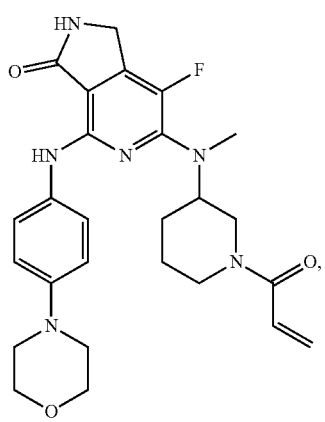
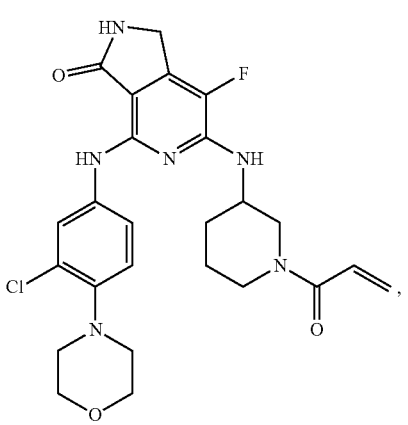
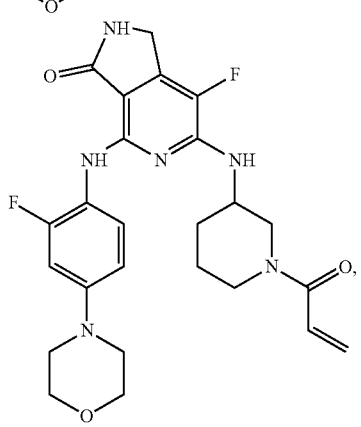
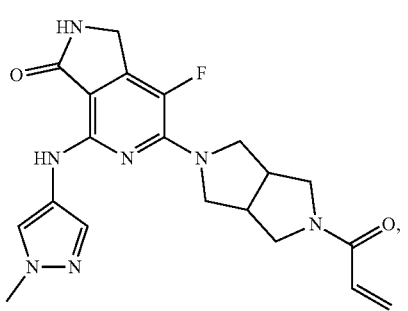

-continued
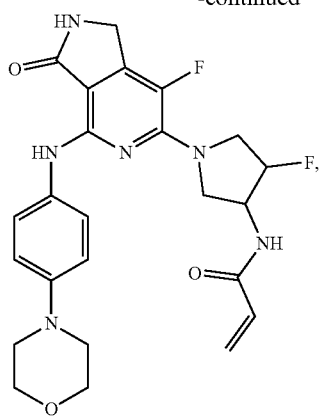
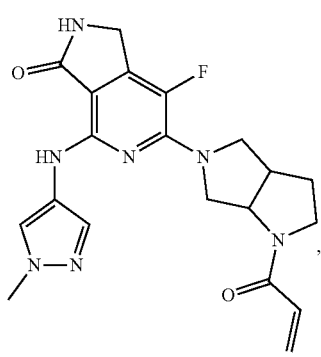
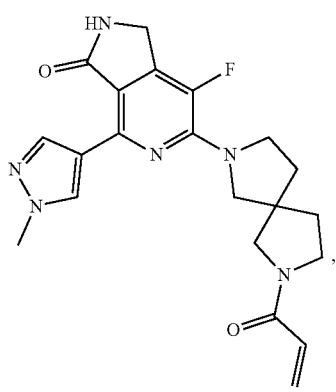
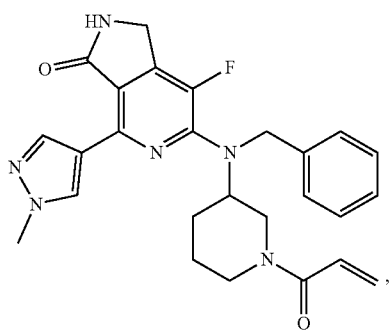
-continued
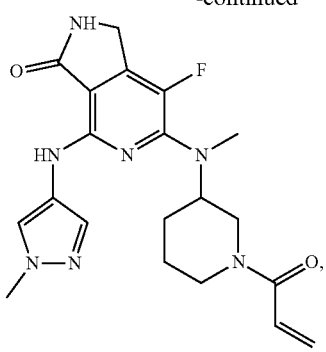
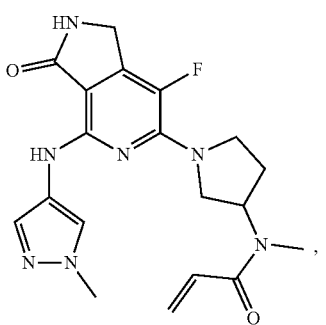
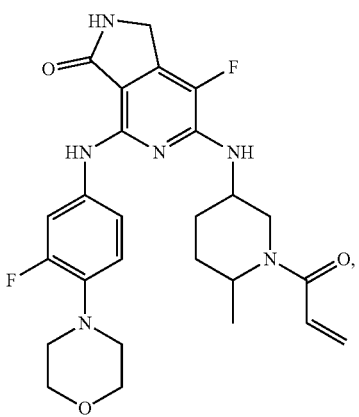
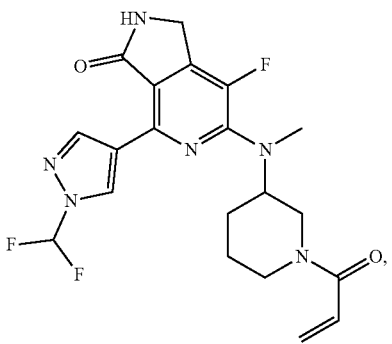

-continued
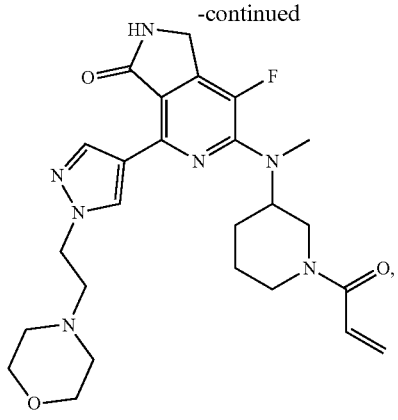
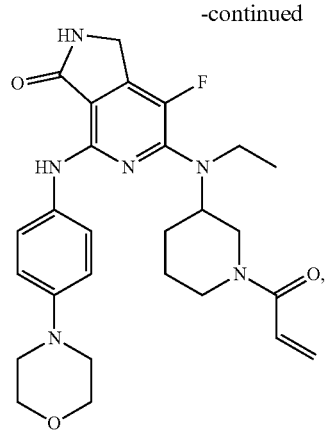
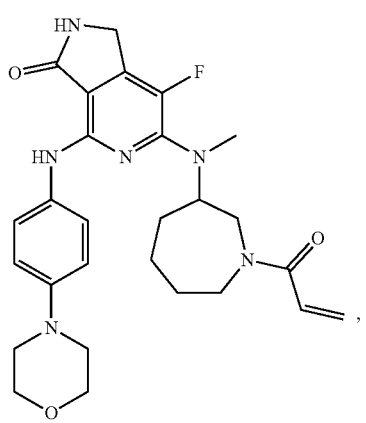
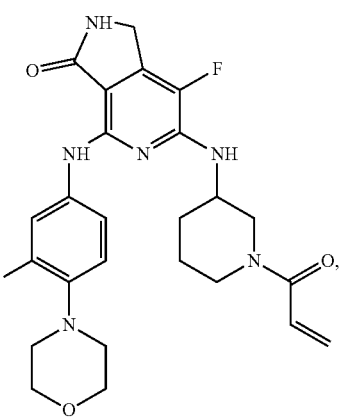
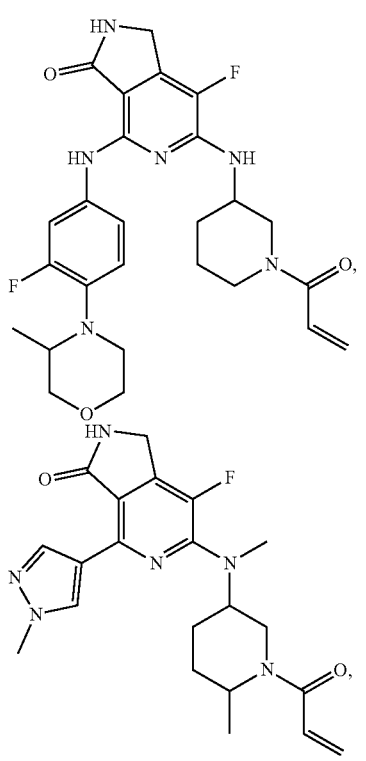
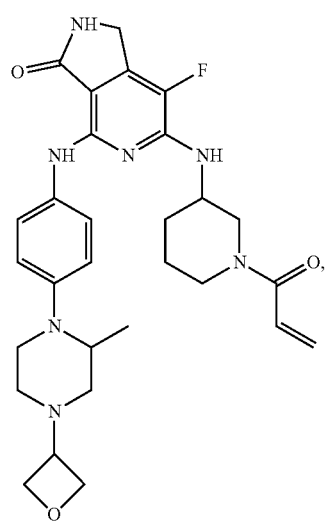

37
-continued

38
-continued

-continued
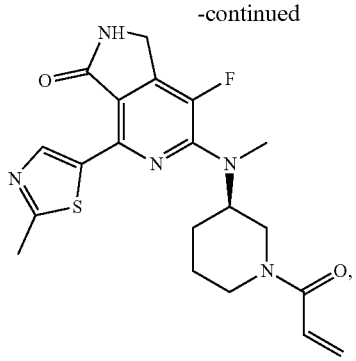
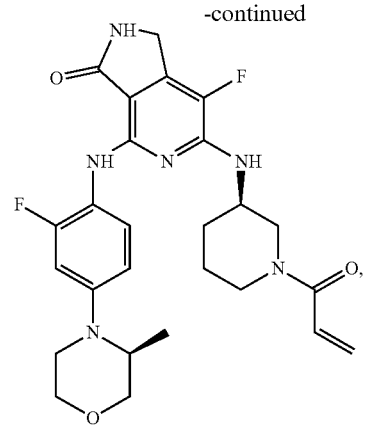
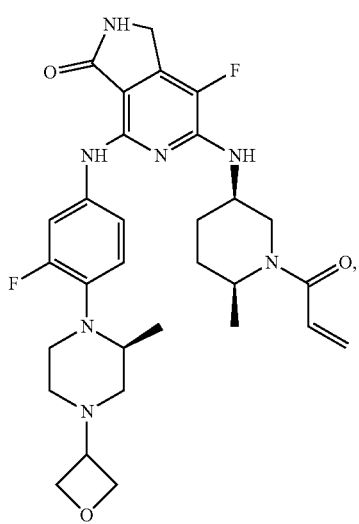
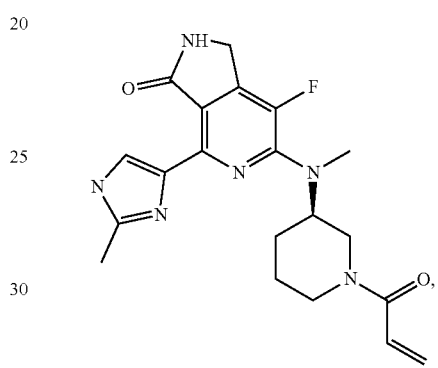
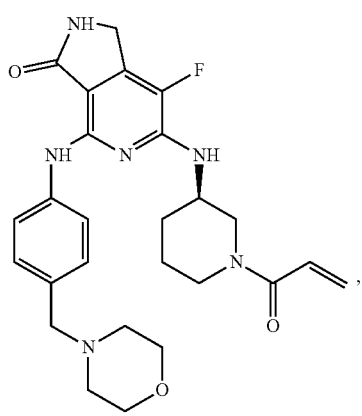
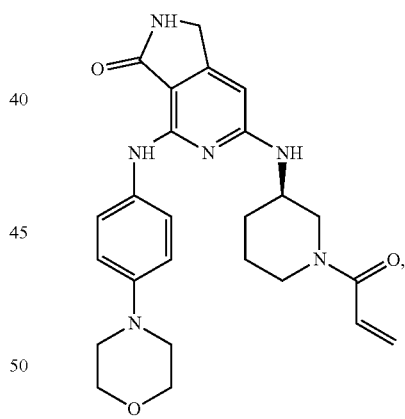
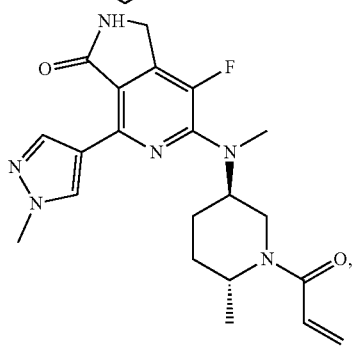
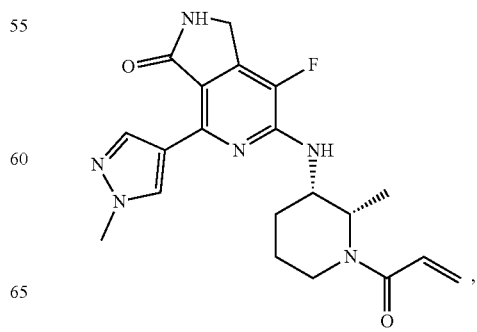

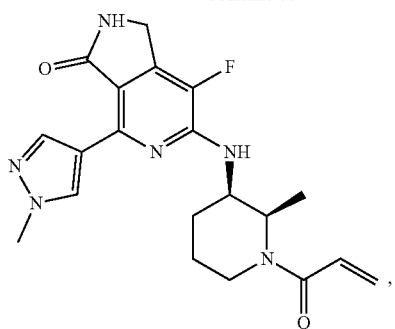
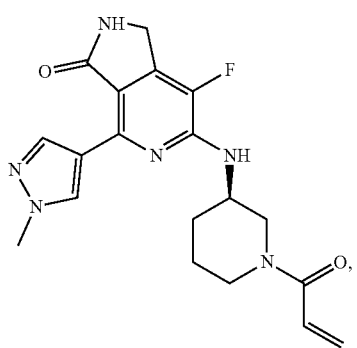
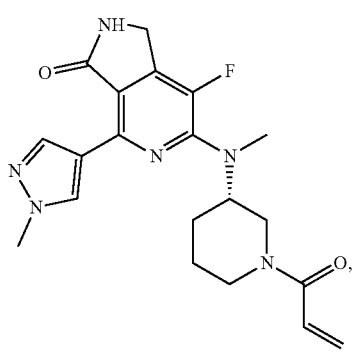
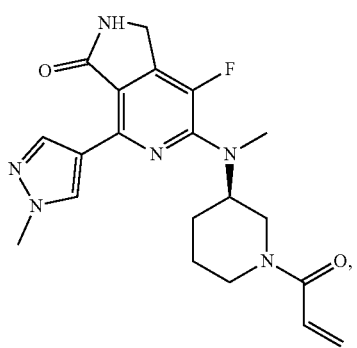
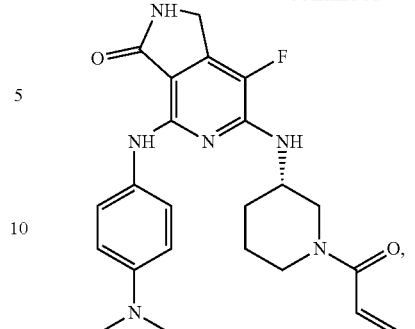
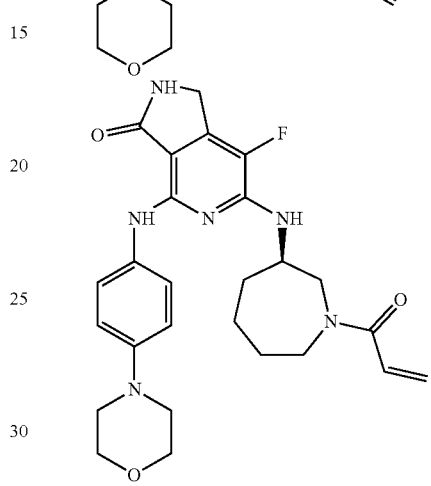
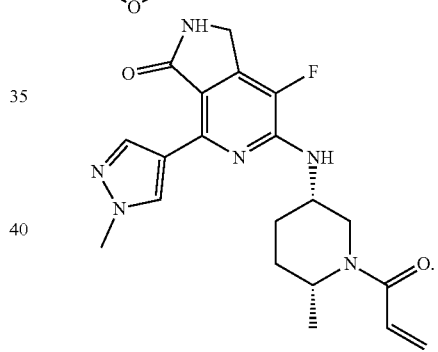
or
In another preferred embodiment, the compound of formula (II) is a structure selected from the group D2.
In another preferred embodiment, the structure of group D2 is:
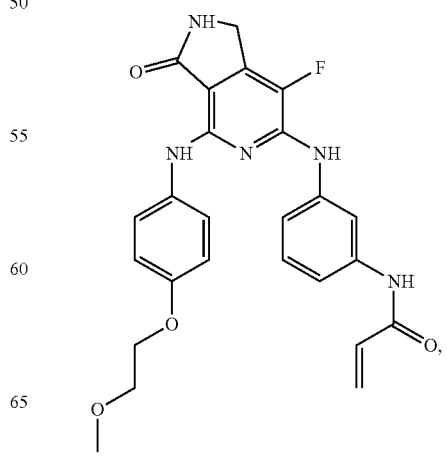

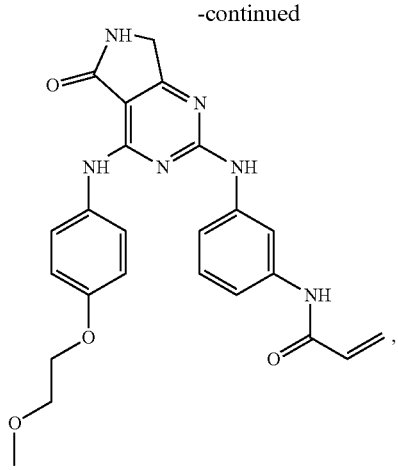
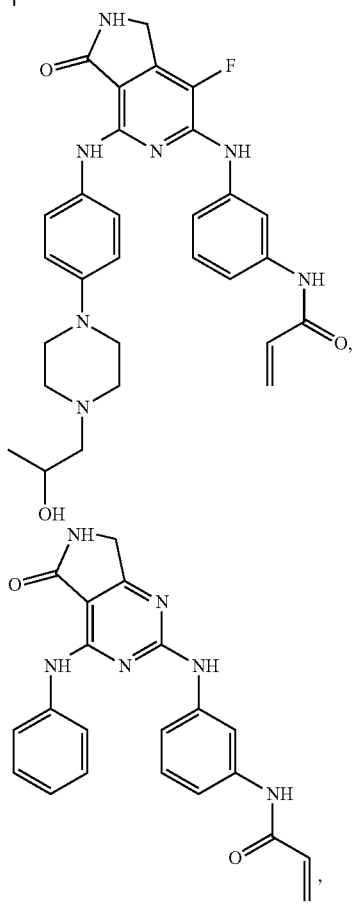
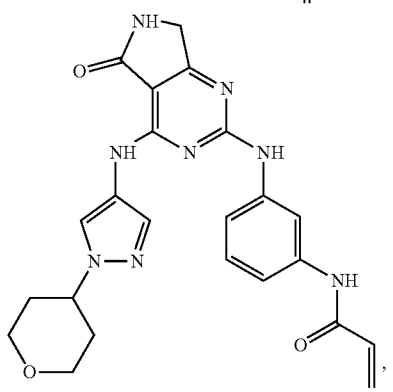
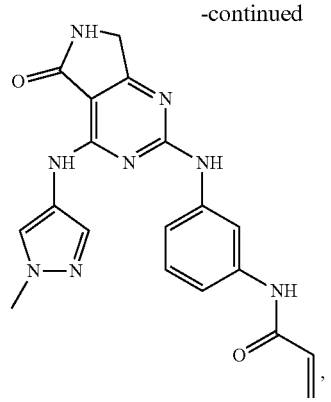
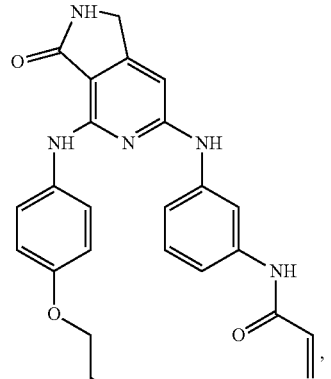
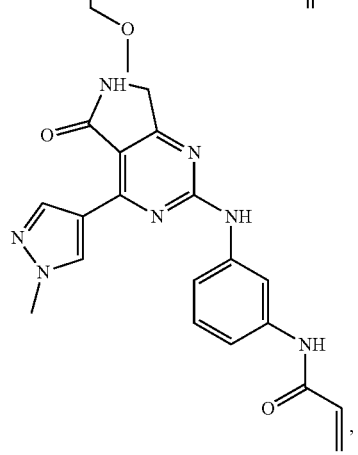
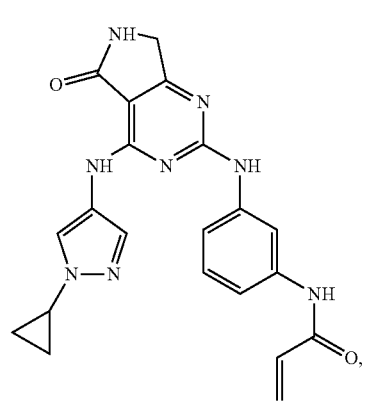

-continued

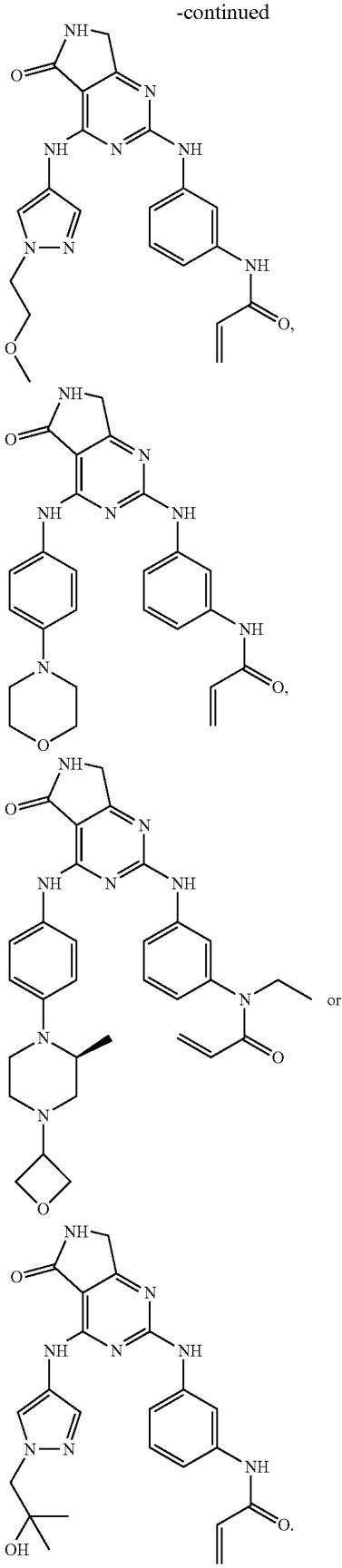

In the third aspect of the present disclosure, a pharmaceutical composition is provided, the pharmaceutical composition comprising the compound of the first or second aspect of the present disclosure, or a pharmaceutically acceptable salt, solvate, stereoisomer or prodrug thereof; and a pharmaceutically acceptable carrier or excipient.

In the fourth aspect of the present disclosure, a use of the compound of the first or second aspect of the present disclosure, or a pharmaceutically acceptable salt, solvate, stereoisomer or prodrug thereof or the pharmaceutical composition of the third aspect of the present disclosure, in the preparation of a drug as a kinase inhibitor is provided.

In another preferred embodiment, the drug is used as a BTK inhibitor.

In the fifth aspect of the present disclosure, a use of the compound of the first or second aspect of the present disclosure, or a pharmaceutically acceptable salt, solvate, stereoisomer or prodrug thereof or the pharmaceutical composition of the third aspect of the present disclosure, in the preparation of a drug used in the treatment of B cells-mediated diseases is provided.

In the sixth aspect of the present disclosure, a method for the treatment of B cells-mediated diseases is provided, the method comprising administering the compound of the first or second aspect of the present disclosure, or a pharmaceutically acceptable salt, solvate, stereoisomer or prodrug thereof or the pharmaceutical composition of the third aspect of the present disclosure in a therapeutically effective amount to a patient in need of.

In the seventh aspect of the present disclosure, a method for the treatment of B cells-mediated diseases is provided, the method comprising administering the compound of the first or second aspect of the present disclosure, or a pharmaceutically acceptable salt, solvate, stereoisomer or prodrug thereof in a therapeutically effective amount and another therapeutically effective agent to a patient in need of.

In another preferred embodiment, the B cell-mediated disease is selected from the group consisting of a neoplastic disease, a proliferative disease, an allergic disease, an autoimmune disease, and an inflammatory disease.

In another preferred embodiment, the B cell-mediated disease is selected from the group consisting of solid tumor, acute lymphocytic leukemia, chronic lymphocytic leukemia, acute myeloid leukemia, chronic myelogenous leukemia, rheumatoid arthritis, psoriatic arthritis, osteoarthritis, systemic lupus erythematosus, psoriasis, rheumatoid spine inflammation and gouty arthritis.

In another preferred embodiment, the B cell-mediated disease is solid tumor.

In another preferred embodiment, the solid tumor is at least one of lymphoma, soft tissue sarcoma, lymphocytic lymphoma, mantle cell lymphoma, melanoma and multiple myeloma.

It is to be understood that within the scope of the present disclosure, the various technical features of the present disclosure and the various technical features specifically described hereinafter (as in the embodiments) may be combined with each other to form a new or preferred technical solution. Due to space limitations, we will not repeat them herein.

DETAILED DESCRIPTION OF THE DISCLOSURE

The inventors have conducted extensive and in-depth research, and unexpectedly discovered that this kind of aniline-substituted 1,2-dihydropyrrolo[3,4-c]pyridin/pyrimidin-3-one derivatives, particularly N-(3-aminophenyl) acrylamide substituted 1,2-dihydropyrrolo [3,4-c] pyridine/pyrimidin-3-one derivatives have a high inhibitory activity against enzymes such as BTK WT and the like, pBTK Y223, TNFα and other cells. Therefore, this series of compounds are expected to be developed into a drug for treating tumors. On this basis, the inventors completed the present disclosure.

Definition of Terms

As used herein, "alkyl" refers to a straight and branched saturated aliphatic hydrocarbyl. $C_{1-8}$ alkyl is an alkyl containing 1 to 8 carbon atoms, preferably $C_{1-6}$ alkyl or $C_{1-3}$ alkyl defined similarly as $C_{1-8}$ alkyl. Non-limiting examples of alkyl include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof.

As used herein, "cycloalkyl" refers to a saturated or partially unsaturated monocyclic cyclic hydrocarbyl. "$C_{3-8}$ cycloalkyl" refers to a cyclic hydrocarbyl containing 3 to 8 carbon atoms, which is preferably $C_{3-6}$ cycloalkyl defined similarly as $C_{3-8}$ cycloalkyl. Non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclopentyl, and cyclohexenyl.

As used herein, "spiro heterocycle" refers to a polycyclic hydrocarbon which shares one atom (spiro atom) between the single rings, wherein one or two ring atoms are selected from heteroatoms such as nitrogen, oxygen, or $S(O)_n$ (wherein n is an integer from 0 to 2), the remaining ring atoms are carbon atoms. Spiro heterocycle may contain one or more double bonds, but none of the rings have a completely conjugated π-electron system. According to the number of rings, the spiro heterocycles are divided into bicyclic spiro heterocycles or polycyclic spiro heterocycles, preferably bicyclic spiro heterocycles, more preferably 4-membered/5-membered, 5-membered/5-membered, or 5-membered/6-membered bicyclic spiro heterocycle; for example:

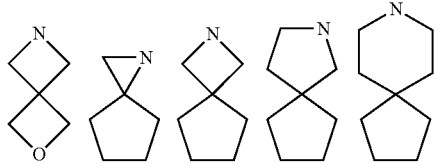

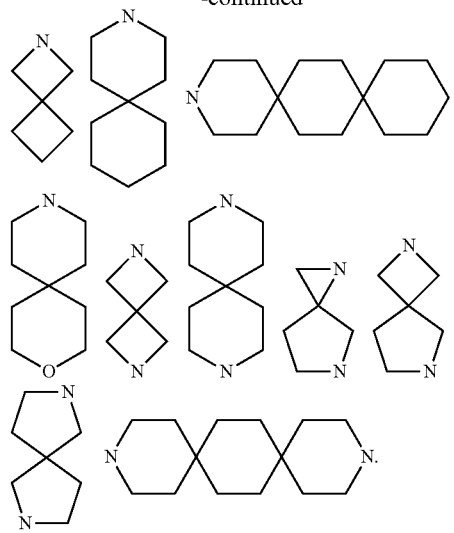

As used herein, "bridged heterocycle" refers to a polycyclic group which shares two or more atoms, wherein one or two ring atoms are selected from heteroatoms such as nitrogen, oxygen, or $S(O)_n$ (wherein n is an integer from 0 to 2), the remaining ring atoms are carbon atoms. Bridged heterocycle may contain one or more double bonds, but none of the rings have a completely conjugated π-electron system. Bicyclic bridged heterocycles or tricyclic bridged heterocycles is preferred, for example:

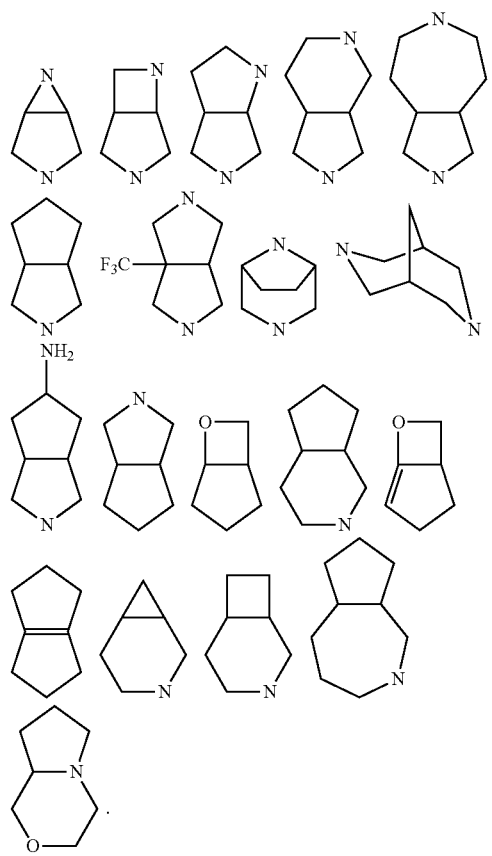

As used herein, "$C_{1-8}$ alkoxy" refers to —O—($C_{1-8}$ alkyl), in which the alkyl is defined as above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy and the like.

As used herein, "$C_{3-8}$ cycloalkoxy" refers to —O—($C_{3-8}$ cycloalkyl), in which the cycloalkyl is defined as above. $C_{3-6}$ cycloalkoxy is preferred. Non-limiting examples include cyclopropyloxy, cyclobutyloxy, cyclopentyloxy, cyclohexyloxy and the like.

As used herein, "$C_{6-10}$ aryl" refers to a full-carbon monocyclic ring or fused polycyclic rings having a conjugated i-electron system (i.e., rings that share a pair of adjacent carbon atoms), and is an aryl containing 6 to 10 carbon atoms; more preferably phenyl and naphthyl, and the most preferably phenyl.

As used herein, "a bond" refers to a covalent bond through which two groups are attached.

As used herein, "halogen" refers to fluorine, chlorine, bromine or iodine.

As used herein, "halogenated" means that one or more (e.g., 1, 2, 3, 4, or 5) hydrogens in a group are substituted by halogen(s).

For example, "halogenated $C_{1-8}$ alkyl" means that the alkyl is substituted by one or more (e.g., 1, 2, 3, 4, or 5) halogens, in which the alkyl is defined as above. Halogenated $C_{1-6}$ alkyl is preferred, and halogenated $C_{1-3}$ alkyl is more preferred. Examples of halogenated $C_{1-8}$ alkyl include, but not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

For example, "halogenated $C_{1-8}$ alkoxy" means that the alkoxy is substituted by one or more (e.g., 1, 2, 3, 4, or 5) halogens, in which the alkoxy is defined as above. Halogenated $C_{1-6}$ alkoxy is preferred, and halogenated $C_{1-3}$ alkoxy is more preferred. Examples of halogenated $C_{1-8}$ alkoxy include (but not limited to) trifluoromethoxy, trifluoroethoxy, monofluoromethoxy, monofluoroethoxy, difluoromethoxy, difluoroethoxy and the like.

For another example, "halogenated $C_{3-8}$ cycloalkyl" means that the cycloalkyl is substituted by one or more (e.g., 1, 2, 3, 4, or 5) halogens, in which the cycloalkyl is defined as above. Halogenated $C_{3-6}$ cycloalkyl is preferred. Examples of halogenated $C_{3-8}$ cycloalkyl include (but not limited to) trifluorocyclopropyl, monofluorocyclopropyl, monofluorocyclohexyl, difluorocyclopropyl, difluorocyclohexyl and the like.

As used herein, "deuterated $C_{1-8}$ alkyl" means that the alkyl is substituted by one or more (e.g., 1, 2, 3, 4, or 5) deuterium atoms, in which the alkyl group is defined as above. Deuterated $C_{1-6}$ alkyl is preferred, and deuterated $C_{1-3}$ alkyl is more preferred. Examples of deuterated $C_{1-8}$ alkyl include (but not limited to) mono-deuterated methyl, mono-deuterated ethyl, di-deuterated methyl, di-deuterated ethyl, tri-deuterated methyl, tri-deuterated ethyl and the like.

As used herein, "amino" refers to —$NH_2$, "cyano" refers to —CN, "nitro" refers to —$NO_2$, "benzyl" refers to —$CH_2$-phenyl, "oxo" refers to =O, "carboxyl" refers to —C(O)OH, "acetyl" refers to —C(O)$CH_3$, "hydroxymethyl" refers to —$CH_2$OH, "hydroxyethyl" refers to —$CH_2CH_2$OH, "hydroxy" refers to —OH, "thiol" refers to —SH, and "cyclopropylidene" has a structure of

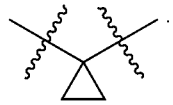

As used herein, "heteroaryl ring" and "heteroaryl" can be used interchangeably and refer to a group that has 5 to 10 ring atoms, preferably 5- or 6-membered monocyclic heteroaryl or 8- to 10-membered bicyclic heteroaryl, shares 6, 10 or π it electrons in the ring array and has 1 to 5 heteroatoms in addition to carbon atoms. "heteroatom" refers to nitrogen, oxygen or sulfur.

As used herein, "4- to 7-membered saturated monoheterocyclic ring" refers to a 4- to 7-membered monocyclic ring in which 1, 2 or 3 carbon atomsare replaced by a heteroatom selected from nitrogen, oxygen or $S(O)_t$ (wherein t is an integer of 0 to 2), no ring moiety —O—O—, —O—S— or —S—S— is included, and the remaining ring atoms are carbon; preferably 4- to 6-membered, more preferably 5- to 6-membered. Examples of 4- to 7-membered saturated monoheterocyclic ring include (but not limited to) propylene oxide, azetidine, oxetane, tetrahydrofuran, tetrahydrothiophene, tetrahydropyrrole, piperidine, pyrroline, oxazolidine, piperazine, dioxolane, dioxane, morpholine, thiomorpholine, thiomorpholine-1,1-dioxide, tetrahydropyran and the like.

As used herein, "5- to 6-membered monocyclic heteroaryl ring" means monoheteroaryl ring containing 5 to 6 ring atoms, for example, includeing (but not limited to) a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, a pyrazine ring and the like.

As used herein, "8- to 10-membered bicyclic heteroaryl ring" refers to a bicyclic heteroaryl ring containing 8 to 10 ring atoms, for example including (but not limited to) benzofuran, benzothiophene, indole, isoindole, quinoline, isoquinoline, indazole, benzothiazole, benzimidazole, quinazoline, quinoxaline, cinnoline and phthalazine.

As used herein, "substituted" means one or more hydrogen atoms in a group, preferably 1 to 5 hydrogen atoms, are each independently substituted by the corresponding number of substituents, more preferably, 1 to 3 hydrogen atoms are each independently substituted by the corresponding number of substituents. It is obvious that substituents are only in their possible chemical positions, and those skilled in the art can, without any undue effort, determine (by experiment or theory) that it is possible or impossible. For example, an amino or hydroxyl with free hydrogen may be unstable when combined with a carbon atom having an unsaturated (such as olefinic) bond.

As used herein, any above-mentioned group may be substituted or unsubstituted. When the above-mentioned group is substituted, the substituent is preferably 1 to 5 (more preferably 1 to 3) of the following groups which is independently selected from the group consisting of halogen, —O($CH_2$)$_p$O$C_{1-8}$ alkyl, —O($CH_2$)$_p$OH, —($CH_2$)$_p$O$C_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), hydroxymethyl, hydroxyethyl, hydroxy, carboxy, $NR_{a0}R_{b0}$, —C(O)O$C_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), —SO$_2$$C_{1-8}$ alkyl (preferably —SO$_2$$C_{1-6}$ alkyl, more preferably —SO$_2$$C_{1-3}$ alkyl), $C_{6-10}$ aryl (preferably phenyl), 5- to 6-membered monocyclic heteroaryl and —Y-L; wherein Y is (CH$_2$)$_q$ or C(O), L is a 4- to 6-membered saturated monoheterocyclic ring or 5- or 6-membered monocyclic heteroaryl ring, p and q are each independently 1, 2 or 3, and $R_{a0}$ and $R_{b0}$ are each independently selected from the group consisting of hydrogen, acetyl, $C_{1-8}$ alkyl (preferably $C_{1-6}$ alkyl, more preferably $C_{1-3}$ alkyl), and $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

The above-mentioned various substituents themselves of the present disclosure can also be substituted by the groups described herein.

When 4- to 6-membered saturated monoheterocyclic rings described herein are substituted, the positions of the substituents may be at their possible chemical positions, and representative substitutions of the exemplary monoheterocyclic rings are shown below:

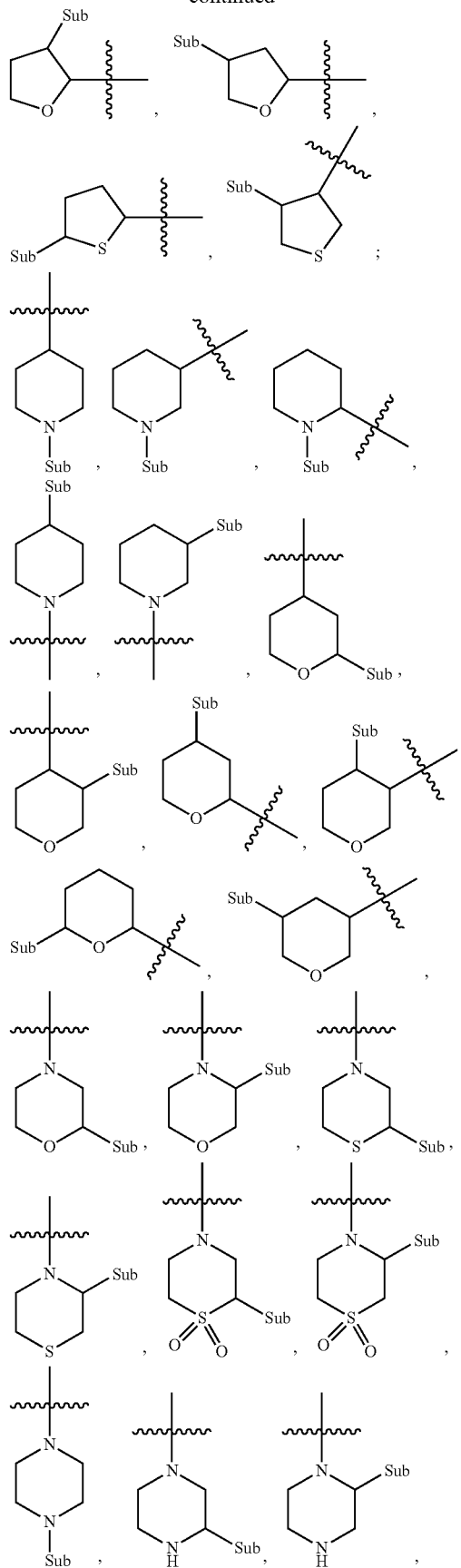

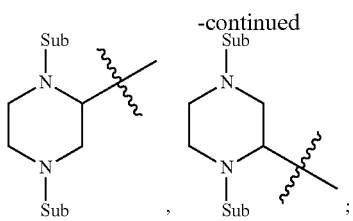

wherein "Sub" represents the various types of substituents described herein; "⁓" represents connections with other atoms.

When the 4- to 6-membered saturated monoheterocyclic rings described herein are substituents, the 4- to 6-membered saturated monoheterocyclic rings may be unsubstituted or substituted with 1, 2 or 3 substituents selected from the group consisting of halogen, hydroxy, $C_{1-3}$ alkyl, O=, $NR_{a0}R_{b0}$, hydroxymethyl, hydroxyethyl, carboxyl, —C(O)$OC_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

The "pharmaceutically acceptable salt" includes pharmaceutically acceptable acid addition salts and pharmaceutically acceptable base addition salts.

"Pharmaceutically acceptable acid addition salt" means a salt formed with an inorganic or organic acid which retains the bioavailability of the free base without any other side effects.

"Pharmaceutically acceptable base addition salts", includes, but not limited to salts of inorganic bases such as sodium, potassium, calcium and magnesium salts, and the like, and salts of organic bases such as ammonium salts, triethylamine salts, lysine salts, arginine salts and the like.

As mentioned herein, "solvate" refers to a complex of the compound of the present disclosure with a solvent. The compound of the present disclosure either reacts in a solvent or precipitates or crystallizes from the solvent. For example, a complex formed with water is referred to as a "hydrate". Solvates of the compound of formula (I) are within the scope of the present disclosure.

The compounds of formula (I) of the present disclosure may contain one or more chiral centers and exist in different optically active forms. When the compound contains one chiral center, the compound contains enantiomers. The present disclosure includes the two isomers and mixtures of the two isomers, such as racemic mixtures. Enantiomers can be resolved by methods known in the art, such as crystallization, chiral chromatography and the like. When the compound of formula (I) contains more than one chiral center, diastereomers may be present. The present disclosure includes resolved optically pure specific isomers as well as mixtures of diastereomers. Diastereomers can be resolved by methods known in the art, such as crystallization and preparative chromatography.

The present disclosure includes prodrugs of the above compounds. Prodrugs include those in which known amino protecting groups or carboxy protecting groups are hydrolyzed under physiological conditions or released via an enzymatic reaction to give the parent compound. Specific prodrug preparation methods can be referred to (Saulnier, M. G.; Frennesson, D. B.; Deshpande, M. S.; Hansel, S. B. and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M J Med. Chem. 2000, 43, 475.).

In general, the compound of the present disclosure, or a pharmaceutically acceptable salt thereof, or a solvate thereof, or a stereoisomer, or prodrug thereof, can be administered in a suitable dosage form with one or more pharmaceutically acceptable carriers. These dosage forms are suitable for oral, rectal, topical, intraoral, and other parenteral administration (e.g., subcutaneous administration, intramuscular administration, intravenous administration, etc.). For example, dosage forms suitable for oral administration include capsules, tablets, granules, syrups and the like. The compound of the present disclosure contained in these preparations may be a solid powder or granule, a solution or suspension in an aqueous or non-aqueous liquid, a water-in-oil or oil-in-water emulsion or the like. The above dosage forms can be prepared from the active compound with one or more carriers or excipients via conventional pharmaceutical methods. The above carriers need to be compatible with the active compound or other excipients. For solid formulations, commonly used non-toxic carriers include, but not limited to, mannitol, lactose, starch, magnesium stearate, cellulose, glucose, sucrose, and the like. Carriers for liquid preparations include water, physiological saline, aqueous dextrose, ethylene glycol, polyethylene glycol, and the like. The active compound can form a solution or suspension with the above carriers.

The compositions of the present disclosure are formulated, quantified, and administered in a manner consistent with medical practice. The "therapeutically effective amount" of a given compound will be determined by the factors such as the particular condition to be treated, the individual being treated, the cause of the condition, the target of the drug, the mode of administration and the like.

As used herein, "therapeutically effective amount" refers to an amount of the compound of the present disclosure that will elicit the biological or medical response of a subject, for example, reduction or inhibition of an enzyme or a protein activity, or amelioration of a symptom, alleviation of a condition, slow or delay disease progression, or prevention of a disease, etc.

As used herein, "pharmaceutically acceptable carrier" refers to non-toxic, inert, solid, semi-solid substance or a liquid filler, a diluent, an encapsulating material or an auxiliary formulation or any type of excipient that is compatible with the patient, preferably a mammal, more preferably a human, and that is suitable for delivering active agent to a target without terminating the activity of the agent.

As used herein, "patient" refers to an animal, preferably a mammal, and more preferably a human. The term "mammal" refers to a warm-blooded vertebrate mammal, including, for example, a cat, a dog, a rabbit, a bear, a fox, a wolf, a monkey, a deer, a rat, a pig and a human.

As used herein, "treating" refers to alleviating, delaying, attenuating, preventing, or maintaining an existing disease or disorder (eg, cancer). The treating also includes curing one or more symptoms of the disease or disorder, preventing development of one or more symptoms of the disease or disorder or reducing one or more symptoms of the disease or disorder to some extent.

Preparation Method

The present disclosure provides preparation methods of compounds of formula (I), and the compounds of the present disclosure can be prepared by a variety of synthetic operations. Exemplary preparation methods of these compounds may include (but not limited to) the processes described below.

Preferably, the compounds of formula (I) can be prepared through the following schemes and exemplary methods described in embodiment, as well as the related publications available for those skilled in the art.

During the specific operation, the procedures of method can be extended or combined as desired in practice.

step 1: Compound 1a is subjected to a nucleophilic substitution reaction with a corresponding amine (primary or secondary amine) under basic conditions.

step 2: Chloride on the pyridine ring is subjected to a Buchwald coupling reaction with the corresponding amine catalyzed by palladium catalyst under basic conditions.

step 3: The amine is deprotected under acidic conditions.

step 4: The secondary amine on ring A is subjected to an amide condensation reaction with an acyl chloride under basic conditions.

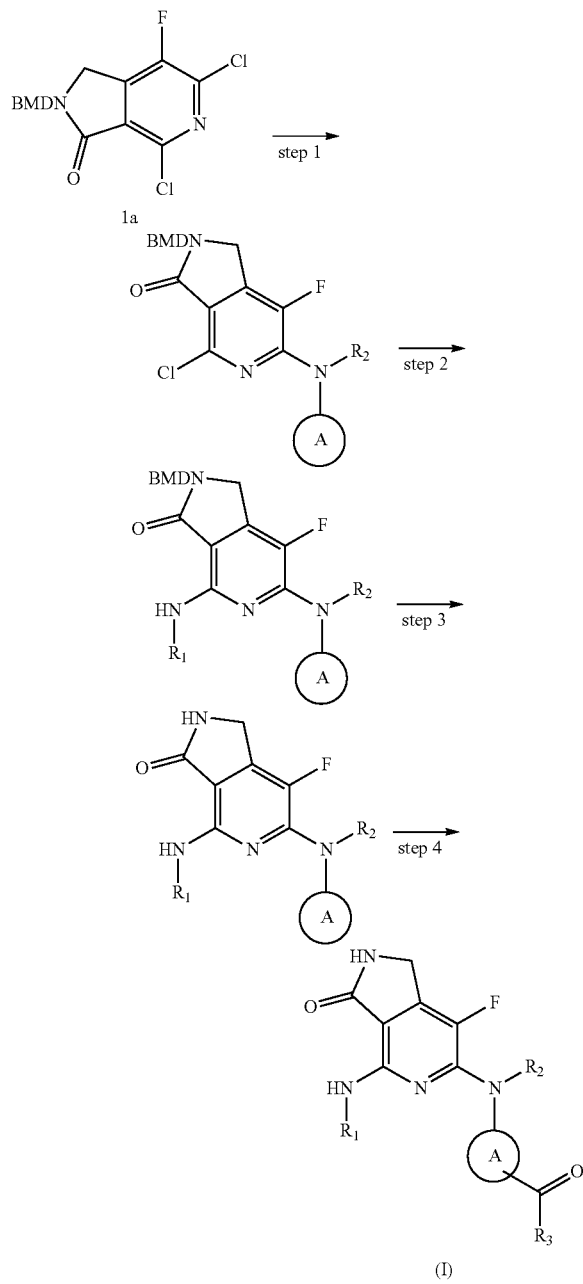

Scheme 1:

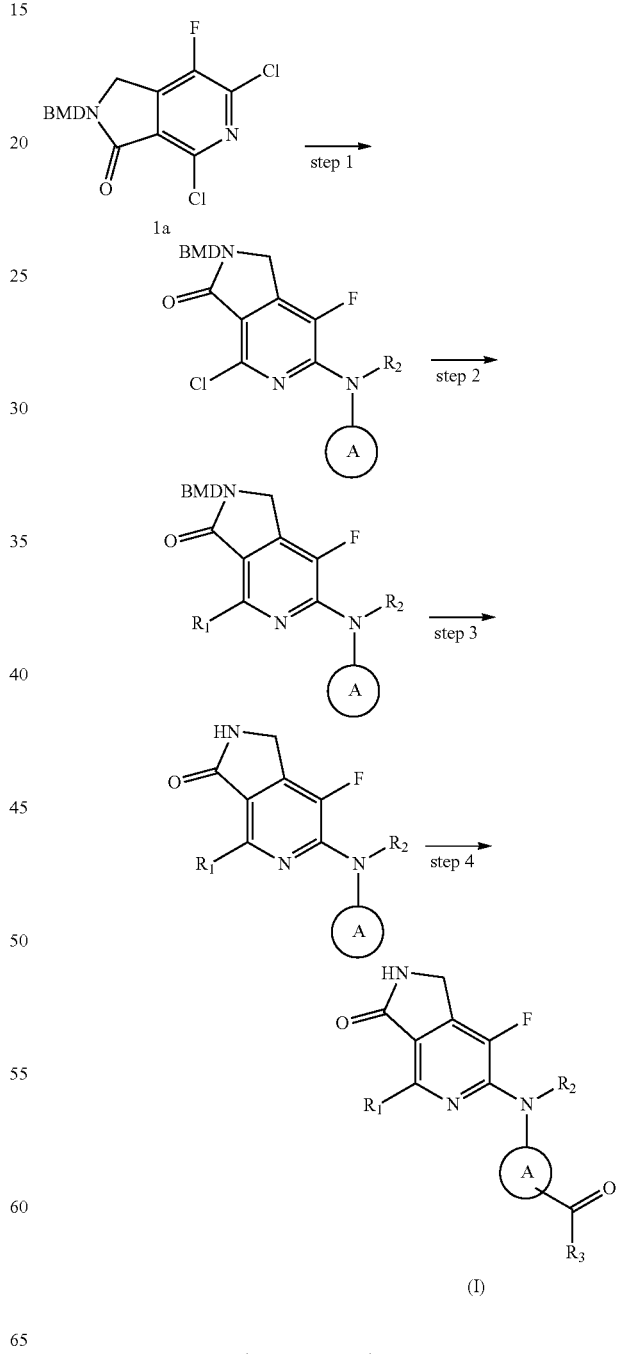

Scheme 2:

Step 1, step 3, and step 4 are the same as step 1, step 3, and step 4 of Scheme 1. In step 2, chloride on the pyridine ring is subjected to a Suzuki coupling reaction with the corresponding boric acid catalyzed by palladium catalyst under basic conditions.

The reactions in the above various steps are conventional reactions known to those skilled in the art. Unless otherwise stated, the reagents and starting materials used in the synthetic route are either commercially available or can be prepared according to the designed different compound structures by those skilled in the art referring to known methods.

The main advantages of the present disclosure over the prior art are:

provided are a series of novel aniline-substituted 1,2-dihydropyrrolo[3,4-c]pyridin/pyrimidin-3-one derivatives, particularly N-(3-aminophenyl) acrylamide-substituted 1,2-dihydropyrrolo[3,4-c]pyridin/pyrimidin-3-one derivatives, which have relatively high inhibitory activity against BTK WT enzyme and against pBTK Y223 cell and the other cells but weak inhibitory activity against EGFR WT. The aniline-substituted 1,2-dihydropyrrolo[3,4-c]pyridin/pyrimidin-3-one derivatives have obvious selective inhibition and can be used as a drug for treating tumors.

The present disclosure will be further illustrated below with reference to the specific examples. It should be understood that these examples are only to illustrate the disclosure but not to limit the disclosure of the disclosure. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present disclosure.

As used herein, DMB refers to 2,4-dimethoxybenzyl, THF refers to tetrahydrofuran, EA refers to ethyl acetate, PE refers to petroleum ether, Ac$_2$O refers to acetic anhydride, NBS refers to N-bromosuccinimide, DCM refers to dichloromethane, AIBN refers to azobisisobutyronitrile, Pd(dppf)Cl$_2$ refers to [1,1'-bis(diphenylphosphino)ferrocene]palladium dichloride, THF refers to tetrahydrofuran, TBSCl refers to tert-butyldimethylchlorosilane, NCS refers to N-chlorosuccinimide, DHP refers to dihydropyran, LiAlH$_4$ refers to lithium aluminum hydride, PMB refers to p-methoxybenzyl, LiHMDS refers to lithium bistrimethylsilylamide, Pd$_2$(dba)$_3$ refers to tris(dibenzylideneacetone)dipalladium, RuPhos refers to 2-dicyclohexylphos-2',6'-diisopropoxy-1,1'-biphenyl, DMAP refers to 4-dimethylaminopyridine, THP is tetrahydropyran, n-BuLi refers to n-butyllithium, TMsOTf refers to trimethylsilyl triflate, TEBAC refers to triethylbenzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIEA refers to N,N-diisopropylethylamine, and BINAP refers to (2R,3 S)-2,2'-bis(diphenylphosphino)-1,1'-binaphthyl.

As used herein, room temperature refers to about 20-25° C.

Preparation of Intermediate 1a

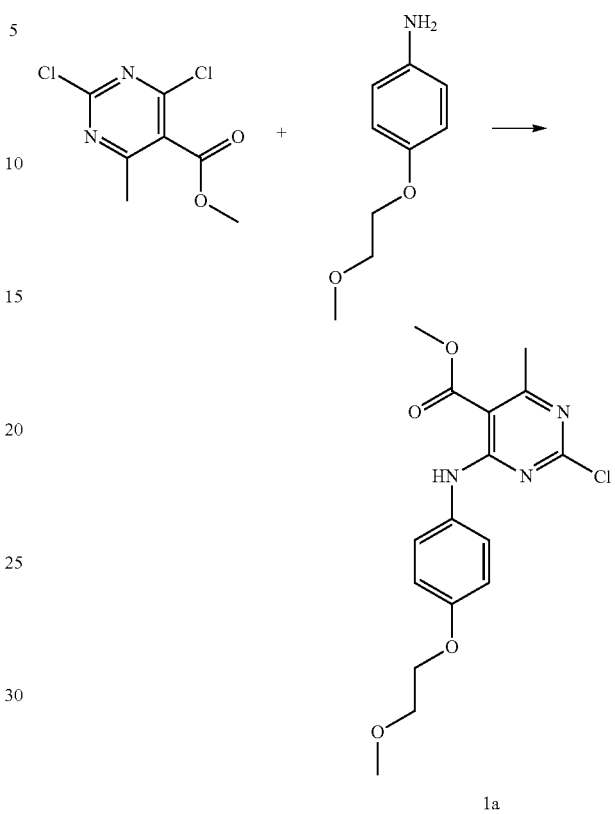

1a

Methyl 2,4-dichloro-6-methylpyrimidine-5-carboxylate (5.0 g, 29.9 mmol) was added to acetonitrile (50 ml), and 4-(2-methoxyethoxy)aniline (6.5 g, 29.9 mmol) and DIEA (7.7 g, 59.8 mmol) were added with stirring at room temperature. The reaction was refluxed at 85° C. for 3 hours. When the starting materials were fully reacted, the solution was diluted with ethyl acetate. The organic phase was washed with saturated brine and purifies by column to give intermediate 1a (6.0 g, 60%) as a yellow solid. ESI-MS m/e 352 [M+1]$^+$.

Preparation of Intermediate 2a

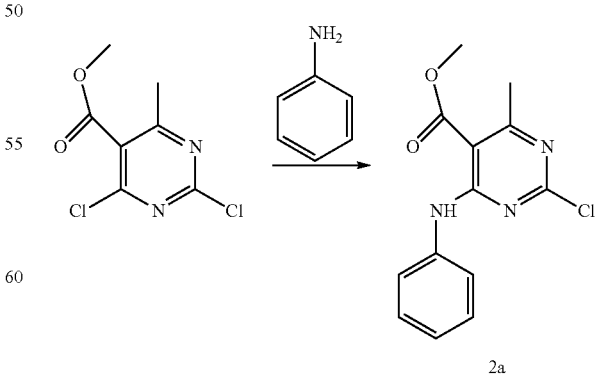

2a

To a 100 ml flask were added methyl 2,4-dichloro-6-methylpyrimidine-5-carboxylate (646 mg, 2.923 mmol), aniline (280 mg, 3.007 mmol), 15 ml of acetonitrile and DIPEA (570 mg, 4.410 mmol). The reaction mixture was stirred at 40° C. for 10 h, acetonitrile was evaporated under reduced pressure and then 20 ml of EtOAc was added. The mixture was washed with 20 ml of water and 20 ml of brine. The organic phase was dired and concentrated to give 850 mg of intermediate 2a as a yellow solid. MS m/z (ESI): 278.1[M+H]+.

Preparation of Intermediate 3a

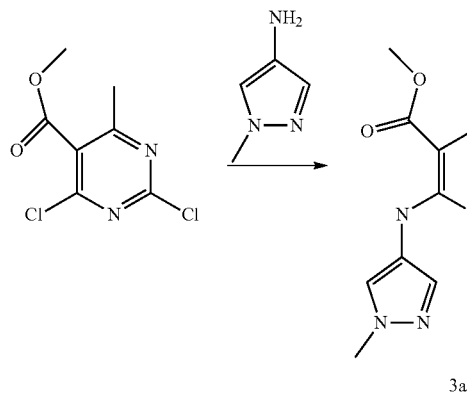

3a

To a 100 ml flask were added methyl 2,4-dichloro-6-methylpyrimidine-5-carboxylate (617 mg, 2.791 mmol), 1-methyl-1H-pyrazol-4-amine (373 mg, 2.792 mmol), 15 ml of acetonitrile and DIPEA (1.08 g, 8.357 mmol). The reaction mixture was stirred at 40° C. for 1 h, acetonitrile was evaporated under reduced pressure and then 30 ml of EtOAc was added. The mixture was washed with 60 ml of water and 30 ml of brine. The organic phase was dired and concentrated to give 830 mg of intermediate 3a as a grey solid. MS m/z (ESI): 282.2[M+H]+.

Preparation of Intermediate 4a

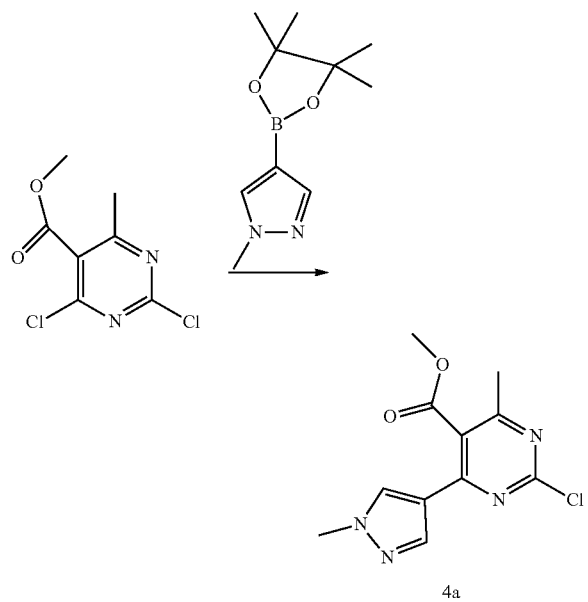

4a

To a 100 ml nitrogen-filled flask were added methyl 2,4-dichloro-6-methylpyrimidine-5-carboxylate (1 g, 4.524 mmol), 1-methyl-4-(4,4,5,5-tetramethyl-1,3,2-dioxaborolan-2-yl)-1H-pyrazole (941 mg, 4.523 mmol), K$_2$CO$_3$ (1.25 g, 9.044 mmol), 16 ml of 1,4-dioxane, 2 ml of water and Pd(dppf)Cl$_2$ (165 mg, 9.044 mmol). The reaction mixture was stirred at 60° C. overnight, then washed with water and extracted with EtOAc. The organic phase was dried, concentrated, purified by combiflash (n-hexane containing 0-40% ethyl acetate) to give 960 mg of yellow oil. MS m/z (ESI): 267.1[M+H]+.

Preparation of Intermediate 5a

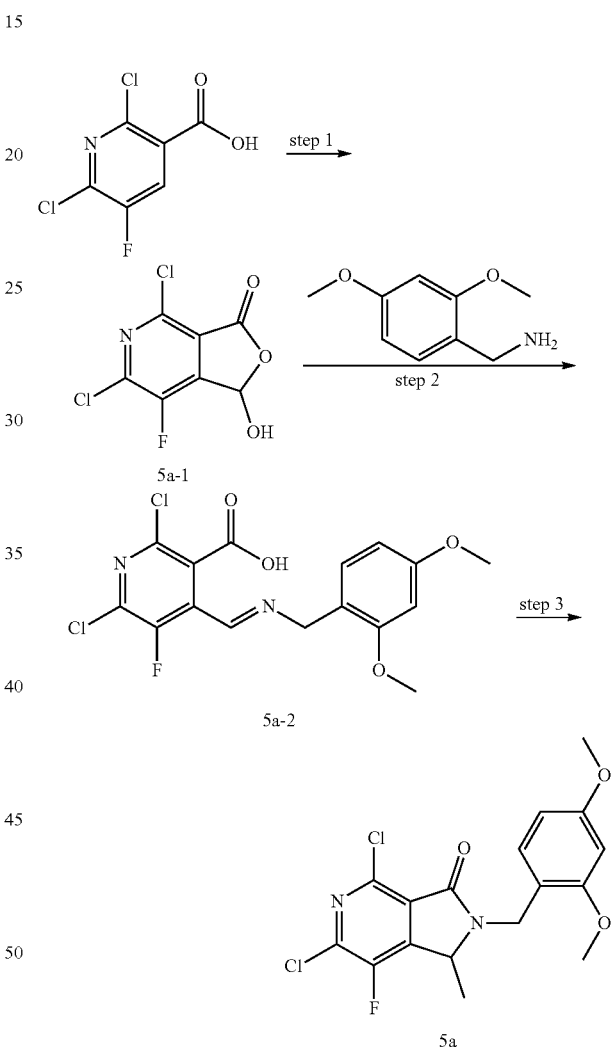

5a

Step 1: diisopropylamine (5.3 g, 52.36 mmol) was dissolved in 50 ml of tetrahydrofuran, which was cooled down to minus 78° C., and then n-butyllithium (2.5 M in hexanes, 21 ml, 52.36 mmol) was added dropwise. After the completion of the dropwise addition, the mixture was stirred at minus 78° C. for half an hour, and a solution of 2,6-dichloro-5-fluoronicotinic acid in tetrahydrofuran (20 ml) was added dropwise. After the addition, the mixture was stirred for another two hours, and then DMF (8.7 g, 119 mmol) was added dropwise. The reaction was continued for 1 hour and then quenched with 2N diluted hydrochloric acid (pH<1) while keeping the temperature of quenching below 0° C. The reaction mixture was extracted with ethyl acetate (2×50 ml). The organic phase was combined and neutralized to a pH of >8 with a saturated aqueous solution of sodium bicarbonate. The aqueous phase was separated, acidified to a pH of <1 with 2N diluted hydrochloric acid and then extracted with ethyl acetate (2×50 ml). The organic phases were combined, washed with water (50 ml) and saturated brine (50 ml) successively, dried over anhydrous sodium sulfate and then filtered. The filtrate was concentrated, beaten with a mixed solvent of petroleum ether and ethyl acetate (8:1, 135 ml), filtered, and dried under reduced pressure to give 5a-1 (3.08 g, 54.4%) as a white solid. $^1$H NMR (400 MHz, DMSO-d6) 8.81 (s, 1H), 6.82 (s, 1H).

Step 2: compound 5a-1 (2.5 g, 10.5 mmol) was dissolved in 15 mL of methanol and then 2,4-dimethoxybenzylamine (1.84 g, 11.03 mmol) was added. The reaction was stirred at room temperature for 1 hour, solid precipitate was formed, and filtered. The filter cake was washed with petroleum ether and dried to give 5a-2 (3.14 g, 77.3%) as a white solid. $^1$H NMR (400 MHz, cdcl$_3$) δ 7.10 (d, J=8.3 Hz, 1H), 6.39 (dd, J=8.3, 2.4 Hz, 1H), 6.35 (s, 1H), 6.27 (d, J=2.4 Hz, 1H), 3.88 (brs, 2H), 3.77 (s, 3H), 3.73 (s, 3H).

Step 3: a solution of lithium methide in ethyl ether (1.6 M, 41.86 mmol) was added dropwise to a suspension of compound 5a-2 (3.24 g, 8.37 mmol) in tetrahydrofuran (35 ml) at minus 78° C. After the dropwise addition was completed, the reaction was stirred for two hours. The reaction mixture was acidified to pH~6 with 1N diluted hydrochloric acid, heated to 50° C. and reacted for 5 hours. After cooling to room temperature, the reaction solution was extracted with ethyl acetate (2×50 ml). The organic layers were combined, washed with saturated brine (50 ml), dried over anhydrous sodium sulfate, and filtered. The filtrate was concentrated under reduced pressure to give a crude product, which was purified by Combi-flash column chromatography [DCM:MeOH=100:0~95:5] to give compound 5a (0.76 g, 23.5%). M$^+$=385.0[M+1]$^+$; $^1$H NMR (400 MHz, cdcl$_3$) δ 7.26 (d, J=8.8 Hz, 1H), 6.46-6.39 (m, 2H), 5.05 (d, J=14.7 Hz, 1H), 4.51 (q, J=6.7 Hz, 1H), 4.33 (d, J=14.7 Hz, 1H), 3.83 (s, 3H), 3.77 (s, 3H), 1.57 (d, J=6.8 Hz, 3H).

Preparation of Intermediate 6a

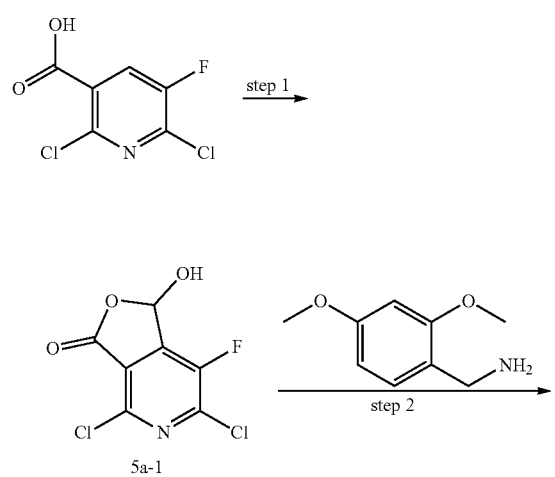

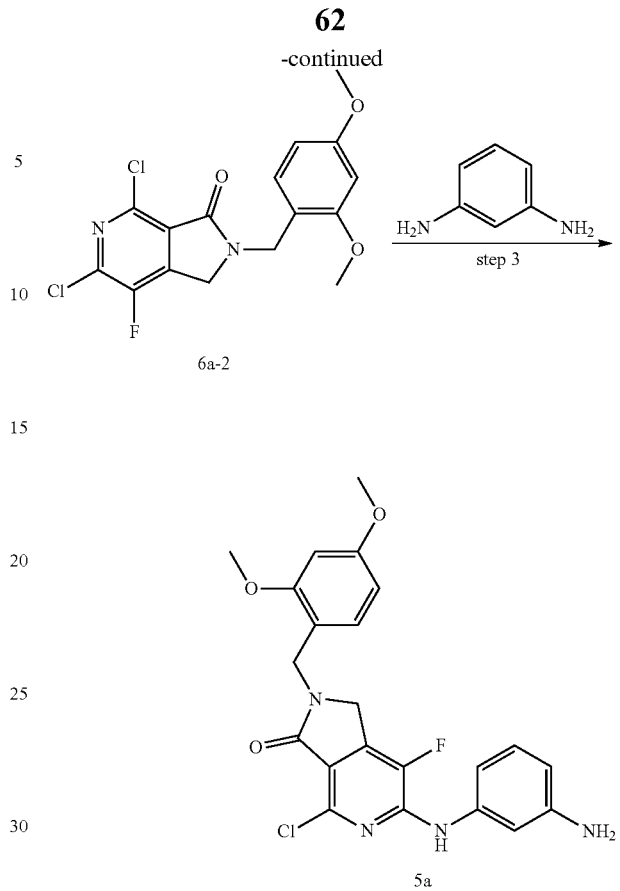

Step 1: to a solution of 2,6-dichloro-5-fluoronicotinic acid (2 g, 10 mmol) in 10 ml of tetrahydrofuran, 20 ml of 2M LDA was added. The reaction mixture was stirred at 0° C. for 1 h and then 10 ml of DMF was added. The reaction solution was stirred at 0° C. for 2 h, washed with brine, adjusted to a pH of 4-5 with Na$_2$CO$_3$, and then extracted with ethyl acetate. The organic phase was washed with saturated sodium bicarbonate solution, and the aqueous phase was adjusted to pH 6 and extracted with ethyl acetate. The organic phase was combined, dried over anhydrous sodium sulfate, and concentrated to give 2.3 g of crude compound 6a-1, which was not purified and used in the next step directly. M$^+$=238.0[M+1]$^+$.

Step 2: to a solution of compound 6a-1 (2.3 g, 10 mmol) in 1,4-dioxane, (2,4-dimethoxyphenyl)methanamine (3.4 g, 20 mmol) and 2 ml of acetic acid were added. The reaction mixture was stirred at room temperature for 1 h and then NaBH(OAc)$_3$ (10 g, 50 mmol) was added. The reaction solution was stirred at 50° C. for 12 h. The solvent was removed under reduced pressure. The residue was washed with brine, extracted with dichloromethane, dried over anhydrous sodium sulfate, and purified by combiflash to give 1.3 g of compound 6a-2. M$^+$=371.0[M+1]$^+$.

Step 3: after adding benzene-1,3-diamine (650 mg, 6 mmol) and DIPEA (1.2 g, 9 mmol) to a solution of compound 6a-2 (1.1 g, 3 mmol) in 10 ml of methylpyrrolidone, the reaction mixture was stirred at 180° C. for 50 min in a microwave reactor. The reaction mixture was washed with brine, extracted with dichloromethane, dried over anhydrous sodium sulfate, and then purified by combiflash to give 1.3 g of compound 6a. M$^+$=443.0[M+1]$^+$.

Preparation of Intermediate 7a

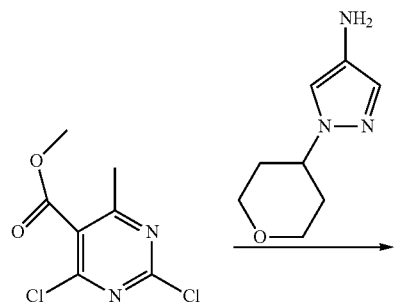

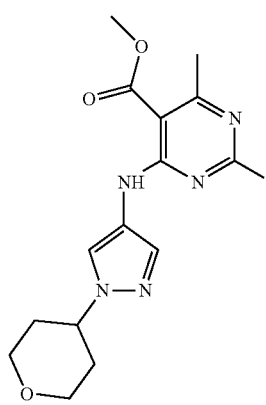

7a

To a 100 ml flask were added methyl 2,4-dichloro-6-methylpyrimidine-5-carboxylate (309 mg, 1.4 mmol), 1-(tetrahydro-2H-pyran-4-yl)-1H-pyrazole-4-amine (234 mg, 1.4 mmol), 10 ml of acetonitrile and DIPEA (0.54 g, 4.18 mmol). The reaction mixture was stirred at 40° C. for 1 h, acetonitrile was evaporated under reduced pressure and then 30 ml of EtOAc was added. The mixture was washed with 60 ml of water and 30 ml of brine. The organic phase was dired and concentrated to give 405 mg of intermediate 7a as a grey solid. MS m/z (ESI): 352.1[M+H]$^+$.

Preparation of Intermediate 8a

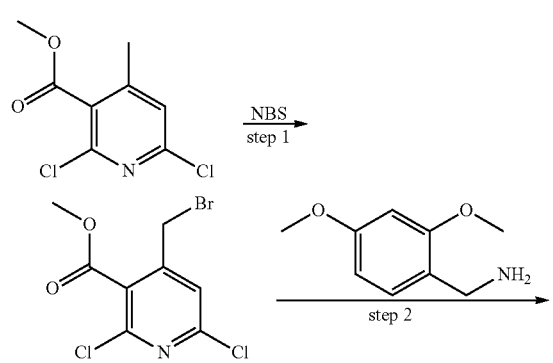

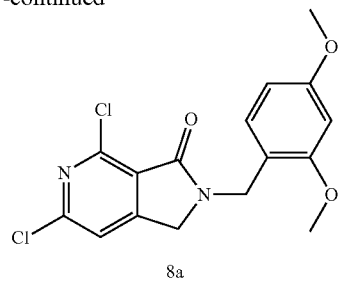

8a

Step 1: to a 250 ml flask were added methyl 2,6-dichloro-4-methylnicotinate (4.24 g, 19.268 mmol), N-bromosuccinimide (4.1 g, 23.036 mmol), azobisisobutyronitrile (160 mg, 0.974 mmol) and 50 ml of carbon tetrachloride. The reaction mixture was stirred at 85° C. overnight. The reaction mixture was concentrated to remove carbon tetrachloride, and 50 ml of ethyl acetate was added, which was then washed with 50 ml of brine and 50 ml of water successively. The organic phase was dried over anhydrous sodium sulfate, concentrated to give 6.4 g of methyl 4-(bromomethyl)-2,6-dichloronicotinate as an oil, MS m/z (ESI): 300.1[M+H]$^+$.

Step 2: to a 250 ml flask was added methyl 4-(bromomethyl)-2,6-dichloronicotinate (6.4 g, 21.408 mmol), (2,4-dimethoxyphenyl)methylamine (3.2 g, 19.14 mmol) and 150 ml of acetonitrile. The reaction mixture was stirred at room temperature for 3 h, and concentrated. The residue was purified by combiflash (hexane containing 0-10% ethyl acetate) to give 2.1 g of intermediate 8a as a yellow solid, yield 30.9%, MS m/z (ESI): 353[M+H]$^+$.

Preparation of Intermediate 9a

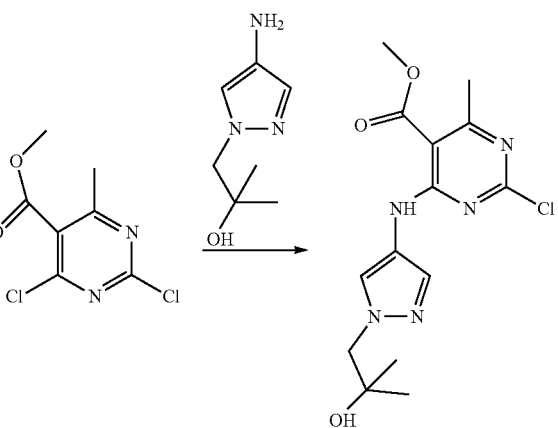

9a

A solution of methyl 2,4-dichloro-6-methylpyrimidine-5-carboxylate (500 mg, 2.3 mmol), 1-(4-amino-1H-pyrazol-1-yl)-2-methylpropan-2-ol (350 mg, 2.3 mmol) and DIPEA (890 mg, 6.9 mmol) in acetonitrile (10 mL) was heated to 40° C. and stirred for 2 h. Water and ethyl acetate were added to the reaction solution and extracted. The organic phase was combined, concentrated and then purified by combiflash to give 400 mg of compound 9a. MS m/z (ESI): 340[M+H]$^+$.

Preparation of Intermediate 10a-13a

Compounds 10a-13a were prepared by referring the method for compound 9a using 1-cyclopropyl-1H-pyrazol- 4-amine, 1-(2-methoxyethyl)-1H-pyrazole-4-amine, 4-morpholinoaniline and (S)-4-(2-methyl-4-(oxetan-3-yl)piperazin-1-yl)aniline as starting materials.
| No. | Structure | MSm/z(ESI) [M + H]+ |
|---|---|---|
| 10a | 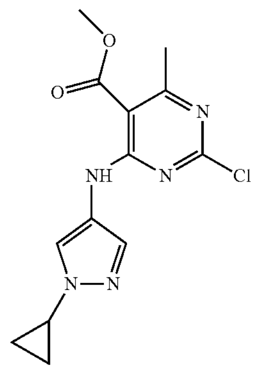 | 308 |
| 11a | 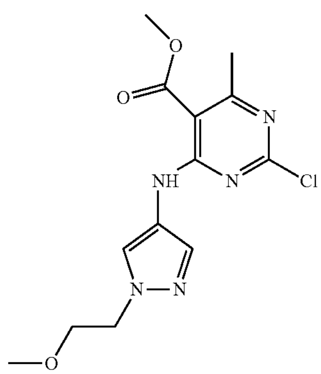 | 326 |
| 12a | 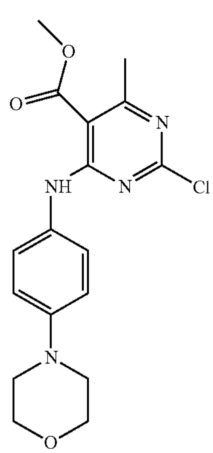 | 363 |
| 13a | | 432 |
Preparation of Intermediate 14a
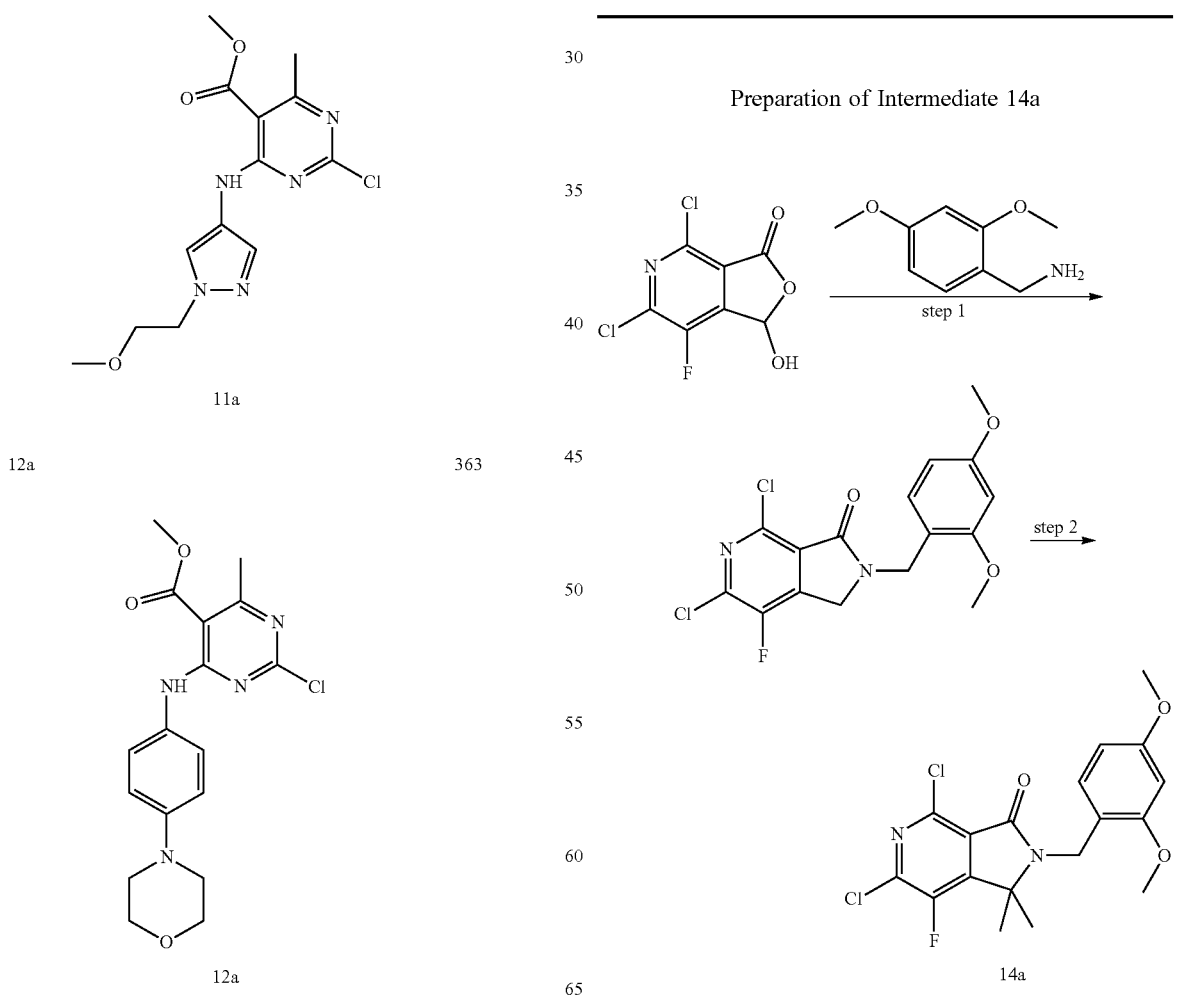

Step 1: 4,6-dichloro-7-fluoro-1-hydroxyfuran[3,4-c]pyridin-3(1H)-one (23.12 g, 97.14 mmol) and 2,4-dimethoxybenzylamine (17.03 g, 102 mmol) were dissolved in 400 ml of 1,4-dioxane. After stirring at room temperature for half an hour, sodium triacetoxyborohydride (41.19 g, 194.28 mmol) was added. The mixture was stirred for another half an hour and then heated to 50° C. After reacting at 50° C. for 8 hours the mixture was cooled to room temperature and then 400 mL of water was added. The mixture was stirred for 10 min, and solid precipitate was formed, and filtered, and the filter cake was washed with water and dried in vacuo to give 2-(2,4-dimethoxybenzyl)-4,6-dichloro-7-fluoro-1,2-dihydropyrrolo[3,4-c]pyridin-3-one (26.23 g, 72.8%) as a yellow solid. $M^+=371.0[M+1]^+$.

Step 2: to a suspension of 2-(2,4-dimethoxybenzyl)-4,6-dichloro-7-fluoro-1,2-dihydropyrrolo[3,4-c]pyridin-3-one (5.0 g, 13.48 mmol) in 50 mL of DMF was added portionwise sodium hydrogen (1.08 g, 26.96 mmol) in an ice bath. The mixture was stirred for 10 min and then methyl iodide (3.83 g, 26.96 mmol) was added. The reaction mixture was slowly warmed to room temperature and then reacted for another 2 hours. The reaction was quenched with water, and the mixture was extracted with ethyl acetate (2×100 mL). The organic phases were combined, washed with water (2×100 ml) and saturated saline (100 ml) successively, dried over anhydrous sodium sulfate, and filtered. The filtrate was concentrated to give a crude product which was purified by Combi-flash column chromatography [PE:EA=100:0~80:20] to give compound 14a (1.3 g, 17.3%). $M^+=399.1[M+1]^+$.

Example 1 Preparation of N-(3-((7-fluoro-4-((4-(2-methoxyethoxy)phenyl)amino)-1-methyl-3-oxo-2,3-dihydro-1H-pyrrolo[3,4-C]pyridin-6-yl)amino)phenyl)acrylamide (G-1)

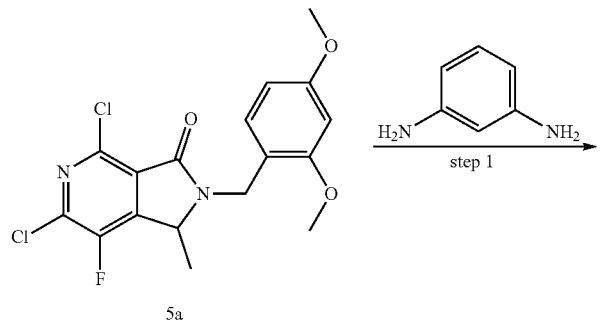

5a

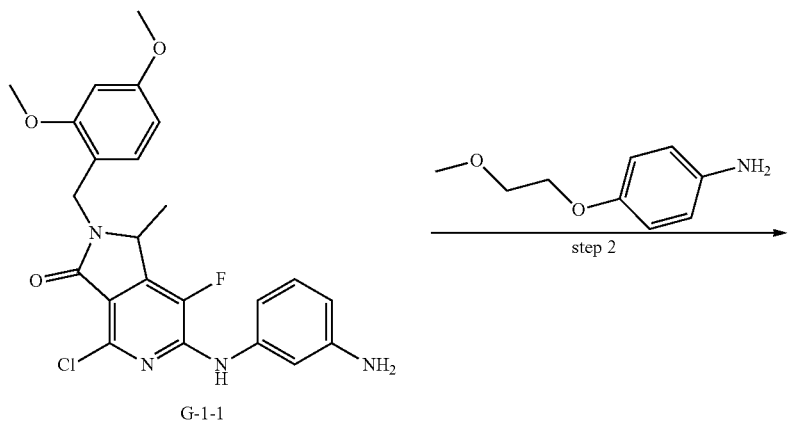

G-1-1

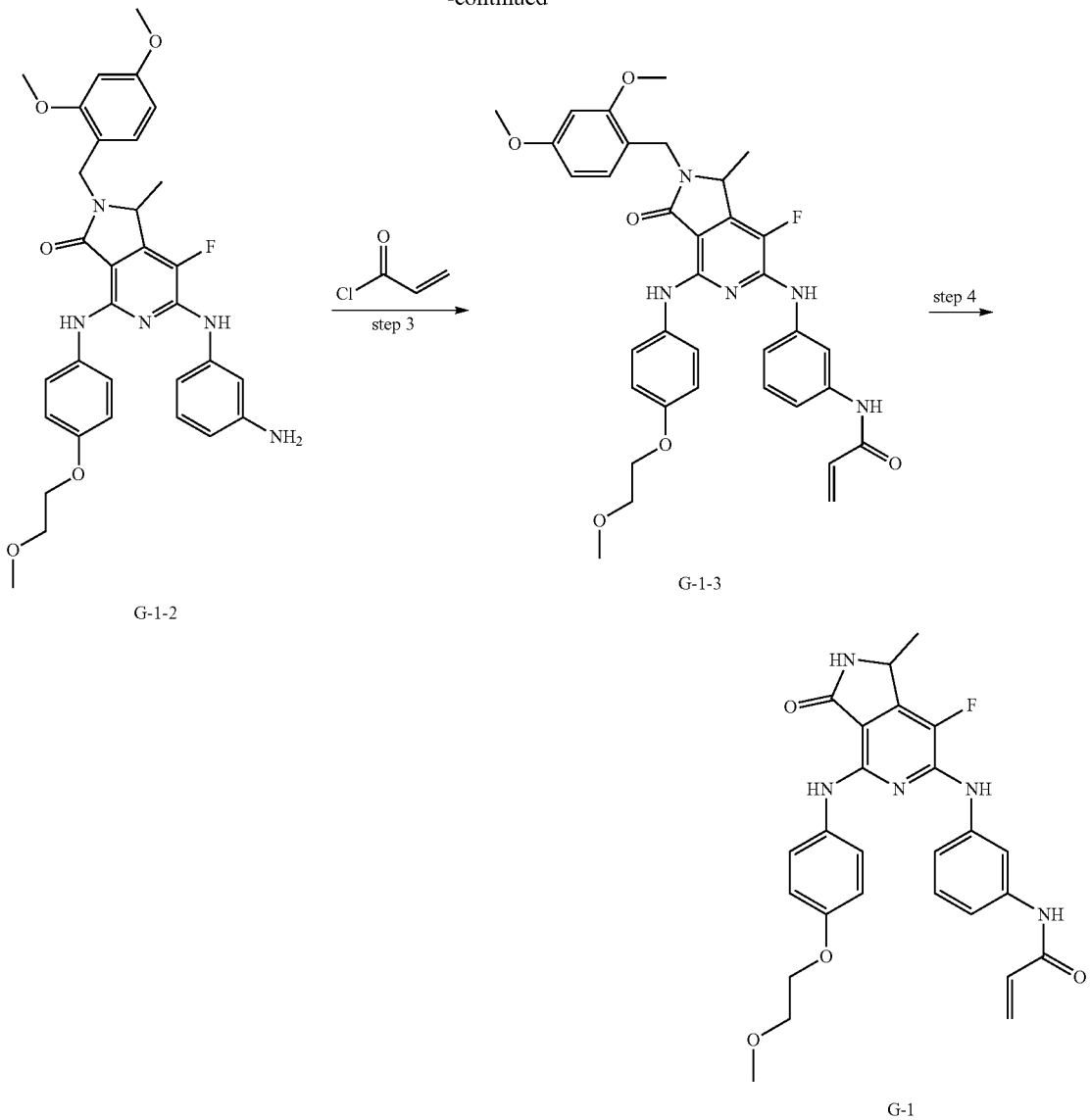

Step 1: compound 5a (500 mg, 1.35 mmol), m-diphenylamine (729 mg, 6.75 mmol), and N,N-diisopropylethylamine (871 mg, 6.75 mmol) were dissolved in 5 ml of NMP. The mixture was heated to 180° C. and reacted for half an hour in a microwave reactor and concentrated to give a crude product which was purified by Combi-flash column chromatography [PE:EA=100:0~30:70] to give compound G-1-1 (300 mg, 25%). M+=443.2[M+1]+.

Step 2: Pd$_2$(dba)$_3$ (52 mg, 0.057 mmol), Xantphos (66 mg, 0.114 mmol) and cesium carbonate (372 mg, 1.14 mmol) were added to a solution of compound G-1-1 (260 mg, 0.57 mmol) and 4-(2-methoxyethoxy)aniline (143 mg, 0.86 mmol) in 1,4-dioxane (6 ml). The mixture was heated to 160° C. and stirred for 20 min in a microwave reactor under the protection of argon. The reaction solution was cooled to room temperature, and then the solid was filtered out. The filter cake was washed with ethyl acetate, and the filtrate was concentrated to give a crude product which was purified by Combi-flash column chromatography [PE:EA=100:0~50:50] to give compound G-1-2 (210 mg, 52.6%). M+=588.2[M+1]+.

Step 3: acryloyl chloride (40 mg, 0.43 mmol) and N,N-diisopropylethylamine (93 mg, 0.72 mmol) were added to a solution of compound G-1-2 (210 mg, 0.36 mmol) in dichloromethane (5 ml). The mixture was stirred at room temperature for one hour. The reaction mixture was concentrated to give a crude product which was purified by Combi-flash column chromatography [PE:EA=100:0~50:50] to give compound G-1-3 (120 mg, 52.4%). M+=642.3[M+1]+.

Step 4: triethylsilane (38 mg, 0.328 mmol) was added to a solution of compound G-1-3 (105 mg, 0.164 mmol) in trifluoroacetic acid (3 ml). The mixture was reacted at room temperature for two hours. The reaction solution was concentrated, purified by preparation liquid phase to give compound G-1 (8 mg, 8.7%). M+=492.1[M+1]+; $^1$H NMR (400 MHz, DMSO) δ 10.13 (s, 1H), 9.14 (s, 1H), 8.64 (s, 1H), 8.43 (s, 1H), 7.88 (s, 1H), 7.48 (d, J=9.0 Hz, 2H), 7.37 (d, J=7.6 Hz, 1H), 7.32-7.21 (m, 2H), 6.72 (d, J=9.0 Hz, 2H), 6.45 (dd, J=17.0, 10.1 Hz, 1H), 6.24 (dd, J=16.9, 2.0 Hz, 1H), 5.74 (dd, J=10.1, 2.0 Hz, 1H), 4.81 (q, J=6.9 Hz, 1H), 4.02-3.95 (m, 2H), 3.66-3.59 (m, 2H), 3.30 (s, 3H), 1.44 (d, J=6.7 Hz, 3H).
Example 2 Preparation of N-(3-(4-(4-(2-methoxyethoxy)phenylamino)-5-oxo-6,7-dihydro-5H-pyrrolo[3,4-d]pyrimidin-2-ylamino)phenyl)acrylamide (G-2)
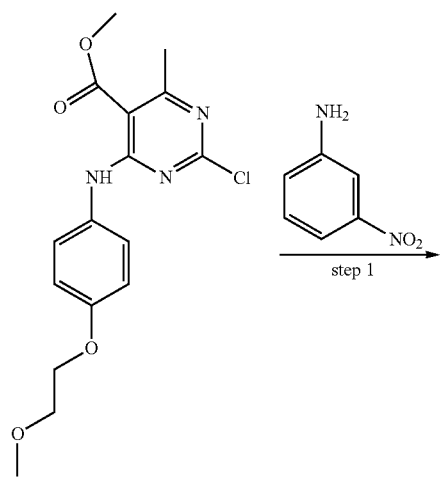
1a
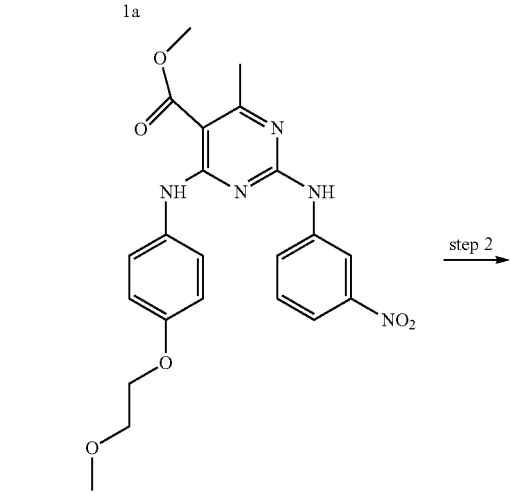
G-2-1
G-2-2
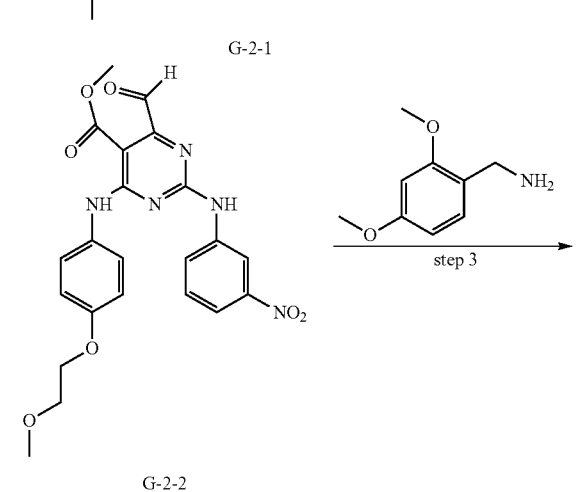
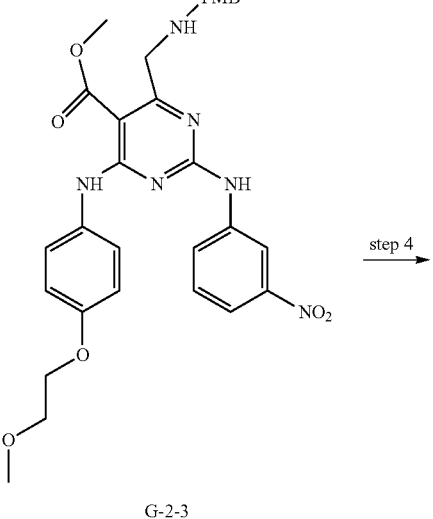
G-2-3
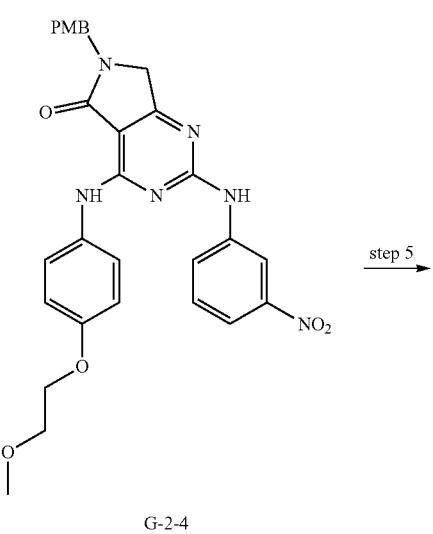
G-2-4
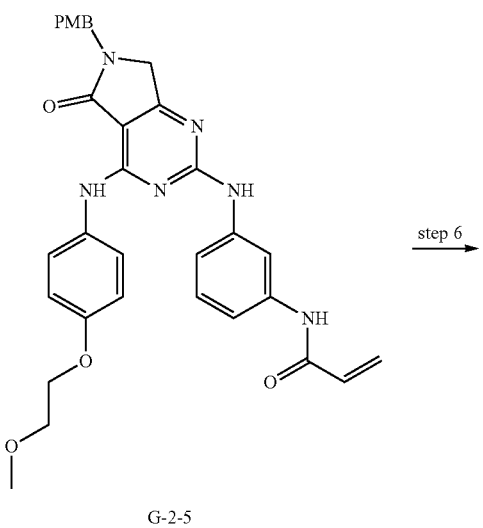
G-2-5

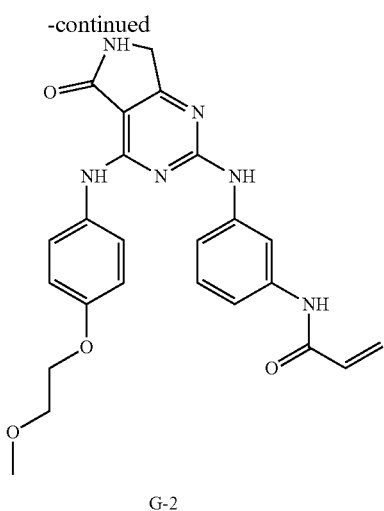

G-2

Step 1: to a 30 ml microwave reactor were added compound 1a (555 mg, 1.578 mmol), 3-nitroaniline (219 mg, 1.586 mmol), TsOH (296 mg, 1.719 mmol) and 12 ml of 1,4-dioxane. The reaction mixture was stirred at 110° C. for 30 min, and then 40 ml of ethyl acetate was added, which was washed with saturated sodium bicarbonate solution (30 ml×2) and brine (30 ml×1). The organic phase was dried, and concentrated to give 760 mg of G-2-1 as a yellow solid. MS m/z (ESI): 454.4[M+H]$^+$, with a yield of 98%.

Step 2: compound G-2-1 (600 mg, 1.323 mmol), SeO$_2$ (920 mg, 8.291 mmol) and 20 ml of 1,4-dioxane were added to a 50 ml reaction flask. The reaction mixture was stirred at 110° C. overnight. The reaction solution was filtered, concentrated, and purified by combiflash (n-hexane containing 20%-90% ethyl acetate) to give 570 mg of G-2-2 as a yellow solid, MS m/z (ESI): 468.2[M+H]$^+$.

Step 3: to a 25 ml flask were added compound G-2-2 (500 mg, 1.07 mmol), (2,4-dimethoxyphenyl)methylamine (200 mg, 1.196 mmol), 20 ml of dichloromethane and 1 ml of tetrahydrofuran. The reaction mixture was stirred at room temperature for 1.5 h and then NaBH(OAc)$_3$ (1.15 g, 5.426 mmol) was added. The mixture was stirred for 1 h at room temperature. The reaction solution was washed with a saturated sodium hydrogencarbonate solution, and extracted with dichloromethane. The organic phase was dried and concentrated. The residue was purified by combiflash (dichloromethane containing 0-10% methanol) to give 65 mg of G-2-3 as yellow oil. MS m/z (ESI): 619.4[M+H]$^+$.

Step 4: compound G-2-3 (65 mg, 0.105 mmol), K$_2$CO$_3$ (40 mg, 0.289 mmol) and 10 ml of acetonitrile were added to a 50 ml flask. After the reaction mixture was stirred at 80° C. for 3 hours, the reaction mixture was filtered. The filtrate was concentrated to give 60 mg of G-2-4 as yellow oil, which was directly used in the next step without purification. MS m/z (ESI): 587.4[M+H]$^+$.

Step 5: 5 ml of ethanol, 5 ml of tetrahydrofuran, 5 ml of a saturated ammonium chloride solution and a trace amount of iron powder were added to 60 mg of crude compound G-2-4. The reaction mixture was stirred at 70° C. for 3 hours, then washed with water, and extracted with ethyl acetate. The organic phase was concentrated and then 5 ml of tetrahydrofuran was added. 3 Drops of DIPEA and 1 drop of acryloyl chloride were added in an ice bath. After the raction mixture was stirred in an ice bath for 1 hour, the reaction mixture was washed with 0.5M hydrochloric acid and extracted with ethyl acetate. The organic phase was dried and concentrated to give 57 mg of G-2-5 as an oil. MS m/z (ESI): 611.3[M+H]$^+$.

Step 6: to a 10 ml microwave reactor tube were added compound G-2-5 (57 mg, 0.093 mmol) and 2 ml of tetrahydrofuran. The reaction mixture was stirred at 110° C. for 20 min, concentrated and purified by Prep-HPLC to give 1.03 mg of G-2 as a white solid. MS m/z (ESI): 461.4[M+H]$^+$. $^1$H NMR (500 MHz, DMSO-d$_6$) δ 9.74 (s, 1H), 8.60 (s, 1H), 8.20 (s, 1H), 7.87 (s, 1H), 7.66 (d, J=8.4 Hz, 2H), 7.47 (d, J=8.0 Hz, 1H), 7.34 (d, J=8.3 Hz, 1H), 7.22 (t, J=8.1 Hz, 1H), 6.87 (d, J=8.9 Hz, 2H), 6.47 (dd, J=17.0, 10.2 Hz, 1H), 6.25 (dd, J=17.0, 2.0 Hz, 1H), 5.75 (dd, J=10.0, 2.1 Hz, 1H), 4.25 (s, 2H), 4.09-4.03 (m, 2H), 3.68-3.62 (m, 2H), 3.31 (s, 3H).

Example 3 Preparation of N-(3-(7-fluoro-4-(4-(2-methoxyethoxy)phenylamino)-3-oxo-2,3-dihydro-1H-pyrrolo[3,4-c]pyridin-6-ylamino)phenyl)acrylamide (G-3)

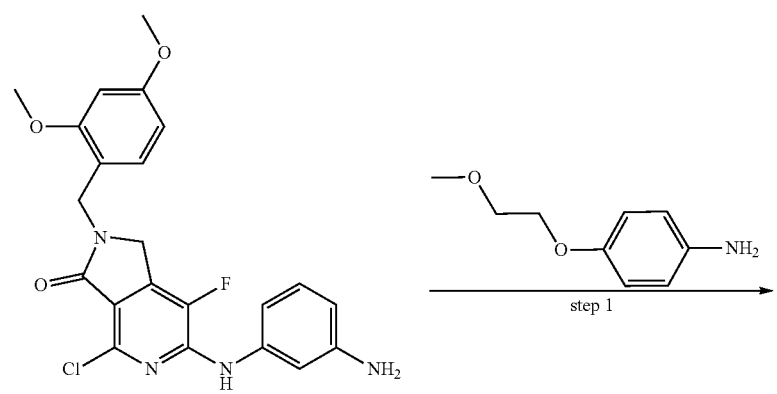

6a step 1

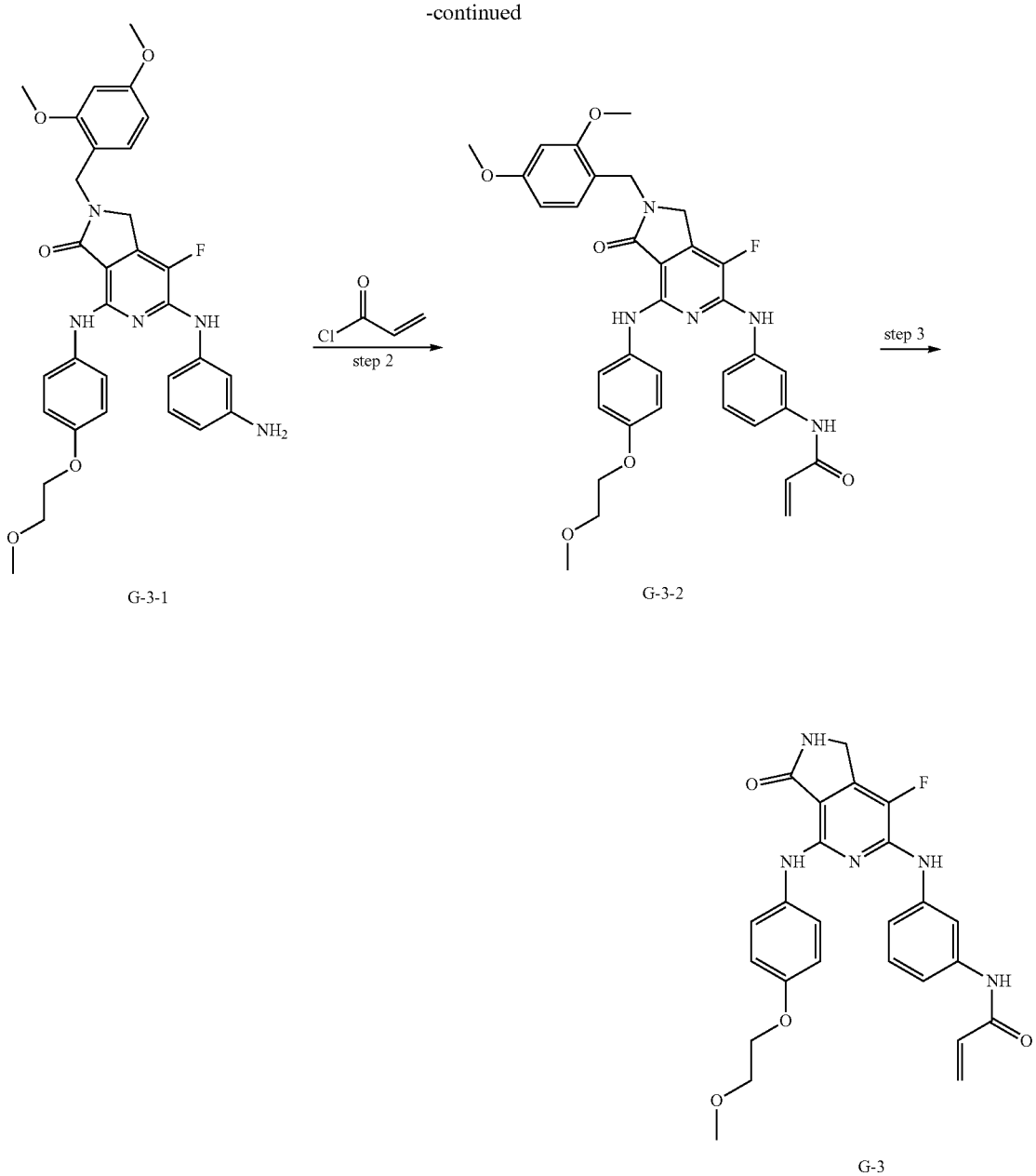

Step 1: Pd$_2$(dba)$_3$ (92 mg, 03.01 mmol), Xantphos (100 mg, 0.2 mmol) and cesium carbonate (1 g, 3 mmol) were added to a solution of compound 6a (442 mg, 1 mmol) and 4-(2-methoxyethoxy)aniline (170 mg, 1 mmol) in 1,4-dioxane (15 ml). The mixture was heated to 160° C. in a microwave reactor under the protection of argon and stirred for 20 min. The reaction solution was cooled to room temperature, and then the solid was filtered out. The filter cake was washed with ethyl acetate, and the filtrate was concentrated to give a crude product which was purified by Combi-flash column chromatography [PE:EA=100:0~50:50] to give compound G-3-1 (420 mg). M$^+$=574[M+1]$^+$.

Step 2: acryloyl chloride (65 mg, 0.7 mmol) and N,N-diisopropylethylamine (182 mg, 1.4 mmol) were added to a solution of compound G-3-1 (420 mg, 0.7 mmol) in dichloromethane (20 ml). The mixture was stirred at room temperature for one hour. The reaction solution was concentrated to give a crude product which was purified by Combi-flash column chromatography [PE:EA=100:0~50:50] to give compound G-3-2 (300 mg). M$^+$=628[M+1]$^+$.

Step 3: a solution of compound G-3-2 (270 mg, 0.45 mmol) in trifluoroacetic acid (3 ml) was charged with argon. The reaction mixture was reacted at 110° C. for 20 min under microwave conditions. The reaction solution was concentrated, and purified by preparation liquid phase to give compound G-3 (13 mg, 11.2%). M$^+$=478[M+1]$^+$. $^1$H NMR (400 MHz, DMSO-d6) δ 10.13 (s, 1H), 9.14 (s, 1H), 8.66 (s, 1H), 8.35 (s, 1H), 7.89 (s, 1H), 7.49 (d, J=9.0 Hz, 2H), 7.37 (d, J=7.5 Hz, 1H), 7.31-7.23 (m, 2H), 6.72 (d, J=9.0 Hz, 2H), 6.45 (dd, J=17.0, 10.1 Hz, 1H), 6.24 (dd, J=17.0, 1.9 Hz, 1H), 5.74 (dd, J=10.1, 1.9 Hz, 1H), 4.45 (s, 2H), 4.02-3.95 (m, 2H), 3.64-3.59 (m, 2H), 3.30 (s, 3H).

Example 4 Preparation of N-(3-(7-fluoro-4-(4-(4-(2-hydroxypropyl)piperazin-1-yl)phenylamino)-3-oxo-2,3-dihydro-1H-pyrrolo[3,4c]pyridin-6-ylamino)phenyl)acrylamide (G-4)
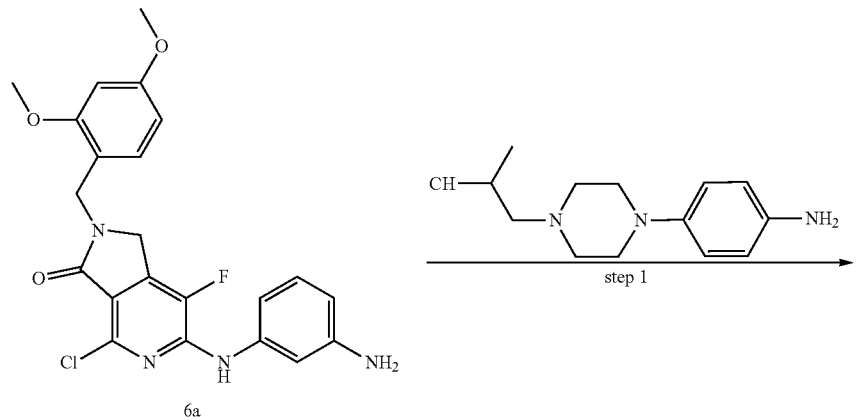
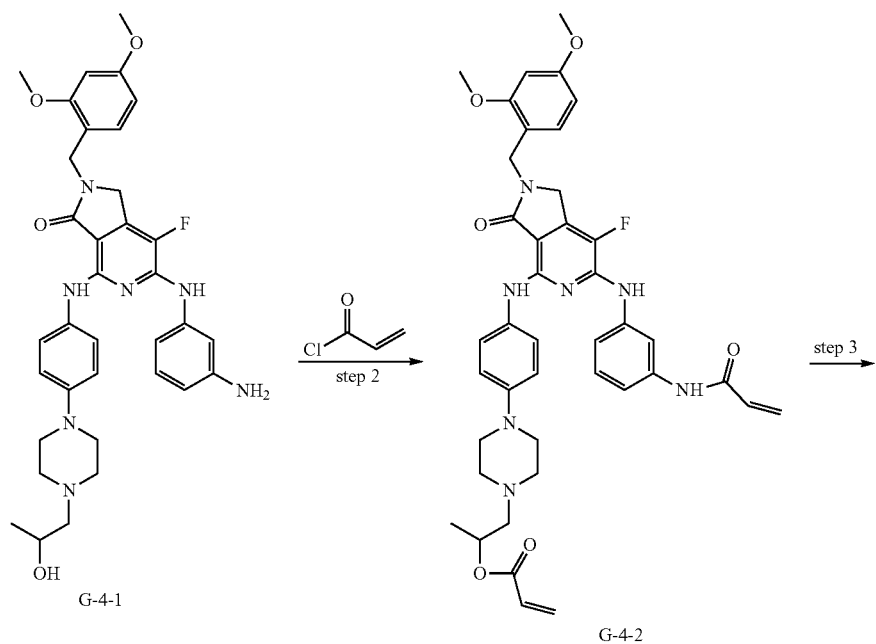

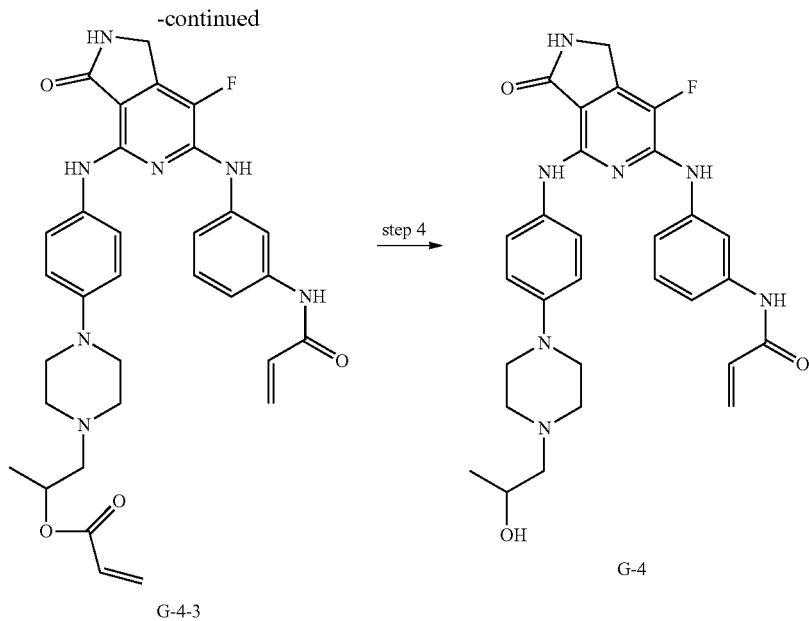

G-4-3

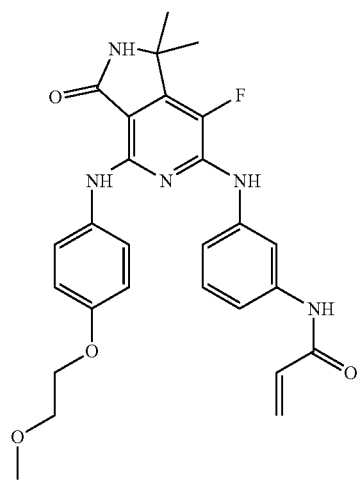

G-4

Step 1: Pd$_2$(dba)$_3$ (90 mg, 0.01 mmol), Xantphos (100 mg, 0.2 mmol) and cesium carbonate (1 g, 3 mmol) were added to a solution of compound 6a (440 mg, 1 mmol) and 1-(4-(4-aminophenyl)piperazin-1-yl)propan-2-ol (235 mg, 1 mmol) in 1,4-dioxane (15 ml). The mixture was heated to 160° C. in a microwave reactor under the protection of argon and stirred for 20 min. The reaction solution was cooled to room temperature, and then the solid was filtered out. The filter cake was washed with ethyl acetate. The filtrate was concentrated under reduced pressure to give a crude product which was purified by Combi-flash column chromatography [PE:EA=100:0~50:50] to give compound G-4-1 (160 mg). M$^+$=642[M+1]$^+$.

Step 2: acryloyl chloride (81 mg, 0.8 mmol) and N,N-diisopropylethylamine (200 mg, 1.5 mmol) were added to a solution of compound G-4-1 (160 mg, 0.3 mmol) in dichloromethane (15 ml). The mixture was stirred at room temperature for 5 hours. The reaction soulution was concentrated to give a crude product which was purified by Combi-flash column chromatography [PE:EA=100:0~50:50] to give compound G-4-2 (300 mg). M$^+$=750[M+1]$^+$.

Step 3: the solution of compound G-4-2 (180 mg, 0.2 mmol) in trifluoroacetic acid (5 ml) was charged with argon. The reaction mixture was reacted at 110° C. for 20 min under microwave conditions. The reaction solution was concentrated, and then purified by preparation liquid phase to give compound G-4-3 (130 mg). M$^+$=600[M+1]$^+$.

Step 4: to a mixed solution of compound G-4-3 (130 mg, 0.2 mmol) in THF (10 ml)/H$_2$O (1 ml) was added lithium hydroxide monohydrate (80 mg, 2 mmol). After the reaction mixture was stirred at room temperature for 5 h, the reaction mixture was washed with brine, extracted with ethyl acetate, and then purified by combiflash to give 20 mg of compound G-4. M$^+$=546.4[M+1]$^+$. $^1$H NMR (400 MHz, DMSO-d6) δ 10.16 (s, 1H), 9.13 (s, 1H), 8.63 (s, 1H), 8.34 (s, 1H), 7.86 (s, 1H), 7.45 (d, J=9.0 Hz, 2H), 7.29-7.21 (m, 2H), 6.72 (d, J=9.1 Hz, 2H), 6.45 (dd, J=16.9, 10.1 Hz, 1H), 6.24 (dd, J=16.9, 2.0 Hz, 1H), 5.77-5.72 (m, 1H), 4.45 (s, 2H), 4.34 (d, J=4.1 Hz, 1H), 3.80 (d, J=5.4 Hz, 2H), 2.97 (d, J=5.1 Hz, 4H), 2.25 (ddd, J=17.9, 15.4, 5.9 Hz, 4H), 1.06 (d, J=6.2 Hz, 3H).

Example 5 Preparation of N-(3-(7-fluoro-4-(4-(2-methoxyethoxy)phenylamino)-1,1-dimethyl-3-oxo-2,3-dihydro-1H-pyrrolo[3,4-c]pyridin-6-ylamino)phenyl)acrylamide (G-5)

G-5

The preparation method for compound G-5 was the same as that in example 1, except that compound 5a in step 1 was replaced by compound 14a. M+=506.3[M+1]$^+$; $^1$H NMR (400 MHz, DMSO-d6) δ 10.10 (s, 1H), 9.11 (s, 1H), 8.61 (s, 1H), 8.41 (s, 1H), 7.85 (s, 1H), 7.43 (d, J=9.0 Hz, 2H), 7.32 (d, J=7.7 Hz, 1H), 7.27-7.15 (m, 2H), 6.70 (t, J=8.7 Hz, 2H), 6.42 (dd, J=17.0, 10.1 Hz, 1H), 6.21 (dd, J=17.0, 2.0 Hz, 1H), 5.71 (dd, J=10.1, 2.0 Hz, 1H), 3.97-3.92 (m, 2H), 3.61-3.56 (m, 2H), 3.27 (s, 3H), 1.51 (s, 6H).

Example 6 Preparation of N-(3-(5-oxo-4-(phenylamino)-6,7-dihydro-5H-pyrrolo[3,4-d]pyrimidin-2-ylamino)phenyl)acrylamide (G-6)

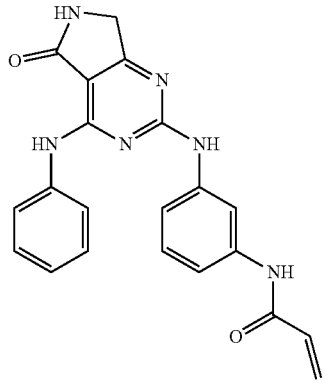

G-6

The preparation method for compound G-6 was the same as that in example 2, except that compound 1a in step 1 was replaced by compound 2a. MS m/z (ESI): 387.3 [M+H]$^+$. $^1$H NMR (400 MHz, DMSO-d$_6$) δ 10.09 (s, 1H), 9.79 (s, 1H), 8.70 (s, 1H), 8.25 (s, 1H), 7.87 (s, 1H), 7.76 (d, J=7.3 Hz, 2H), 7.44 (s, 1H), 7.37-7.11 (m, 4H), 7.03 (t, J=7.3 Hz, 1H), 6.43 (dd, J=17.0, 10.1 Hz, 1H), 6.22 (d, J=15.4 Hz, 1H), 5.72 (d, J=11.9 Hz, 1H), 4.24 (s, 2H).

Example 7 Preparation of N-(3-(5-oxo-4-(1-(tetrahydro-2H-pyran-4-yl)-1H-pyrazol-4-ylamino)-6,7-dihydro-5H-pyrrolo[3,4d]pyrimidin-2-ylamino)phenyl)acrylamide (G-7)

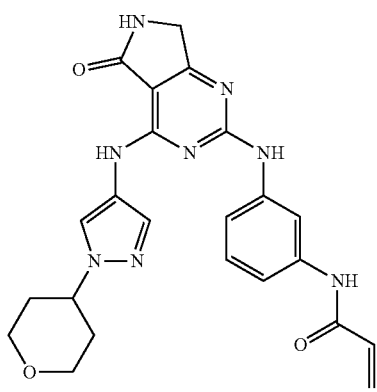

G-7

The preparation method for compound G-7 was the same as that in example 2, except that compound 1a in step 1 was replaced by compound 7a. MS m/z (ESI): 461.2[M+H]$^+$. $^1$H NMR (400 MHz, DMSO-d$_6$) δ 10.14 (s, 1H), 9.62 (s, 1H), 8.67 (s, 1H), 8.19 (s, 1H), 8.10 (s, 1H), 7.86 (s, 1H), 7.76 (s, 1H), 7.39 (s, 2H), 7.24 (t, J=8.2 Hz, 1H), 6.43 (dd, J=17.1, 10.1 Hz, 1H), 6.22 (d, J=17.0 Hz, 1H), 5.72 (d, J=11.8 Hz, 1H), 4.20 (s, 2H), 3.91 (d, J=11.3 Hz, 2H), 3.39 (s, 3H), 1.85 (s, 4H).

Example 8 Preparation of N-(3-(4-(1-methyl-1H-pyrazol-4-ylamino)-5-oxo-6,7-dihydro-5H-pyrrolo[3,4-d]pyrimidin-2-ylamino)phenyl)acrylamide (G-8)

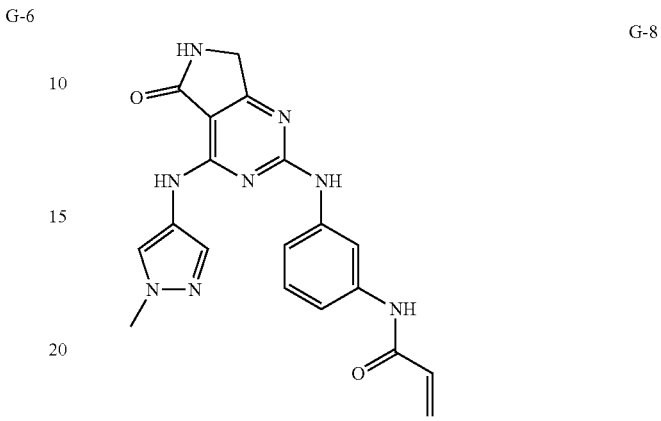

G-8

The preparation method for compound G-8 was the same as that in example 2, except that compound 1a in step 1 was replaced by compound 3a. MS m/z (ESI): 391.3[M+H]$^+$. $^1$H NMR (400 MHz, DMSO-d$_6$) δ 10.10 (s, 1H), 9.64 (s, 1H), 8.66 (s, 1H), 8.12 (d, J=28.4 Hz, 2H), 7.90 (s, 1H), 7.74 (s, 1H), 7.45 (s, 1H), 7.33 (s, 1H), 7.24 (t, J=8.1 Hz, 1H), 6.44 (dd, J=16.9, 10.1 Hz, 1H), 6.29-6.17 (m, 1H), 5.79-5.67 (m, 1H), 4.20 (s, 2H), 3.73 (s, 3H).

Example 9 Preparation of N-(3-(4-(1-(2-hydroxyl-2-methylpropyl)-1H-pyrazol-4-ylamino)-5-oxo-6,7-dihydro-5H-pyrrolo[3,4-d]pyrimidin-2-ylamino)phenyl)acrylamide (G-9)

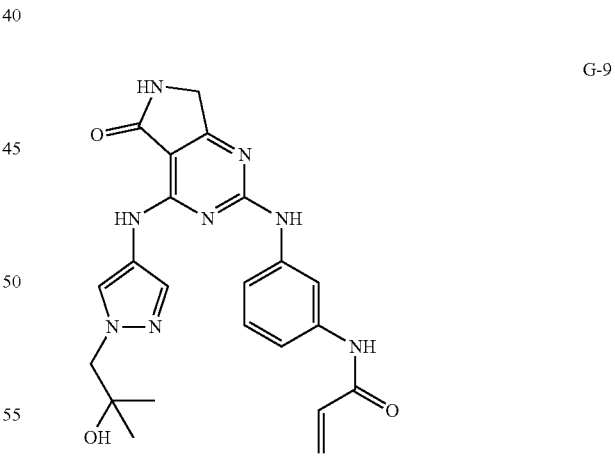

G-9

The preparation method for compound G-9 was the same as that in example 2, except that compound 1a in step 1 was replaced by compound 9a. MS m/z (ESI): 449.2[M+H]$^+$. $^1$H NMR (400 MHz, DMSO-d6): δ 10.10 (s, 1H), 9.65 (s, 1H), 8.69 (s, 1H), 8.10 (s, 2H), 7.89 (s, 2H), 7.51 (d, J=8.0 Hz, 1H), 7.37 (d, J=8.0 Hz, 1H), 7.26 (dd, J$_1$=J$_2$=8.0 Hz, 1H), 6.47 (dd, J$_1$=9.6 Hz, J$_2$=17.2 Hz, 1H), 6.25 (dd, J$_1$=1.6 Hz, J$_2$=17.2 Hz, 1H), 5.75 (dd, J$_1$=1.6 Hz, J$_2$=9.6 Hz, 1H), 4.64 (s, 1H), 4.23 (s, 2H), 3.92 (s, 2H), 1.04 (s, 6H).

Example 10 Preparation of N-(3-(4-(4-(2-methoxyethoxy)phenylamino)-3-oxo-2,3-dihydro-1H-pyrrolo[3,4-c]pyridin-6-ylamino)phenyl)acrylamide (G-10)
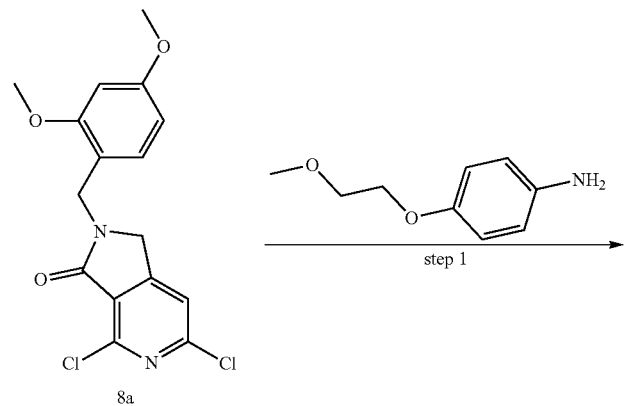
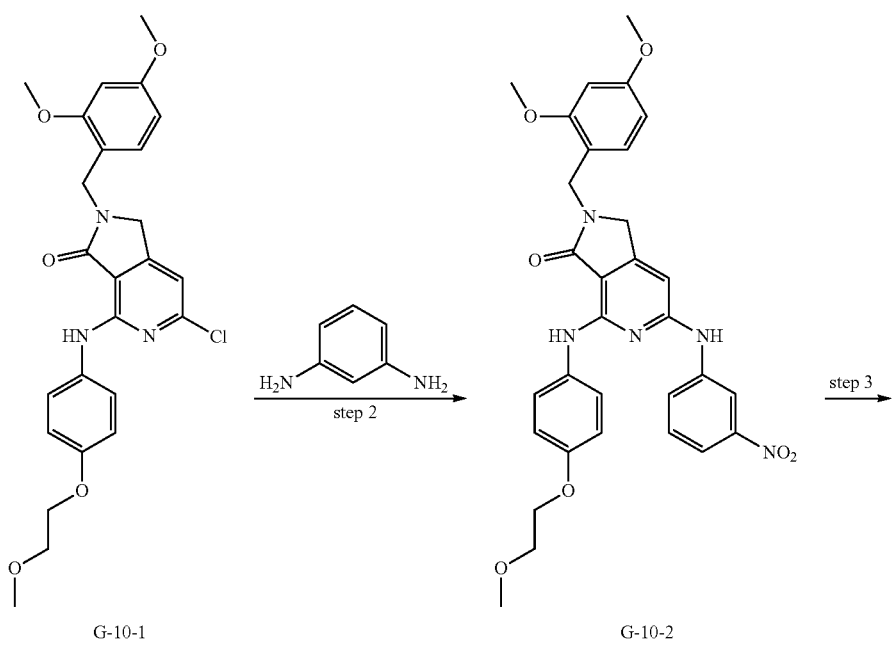

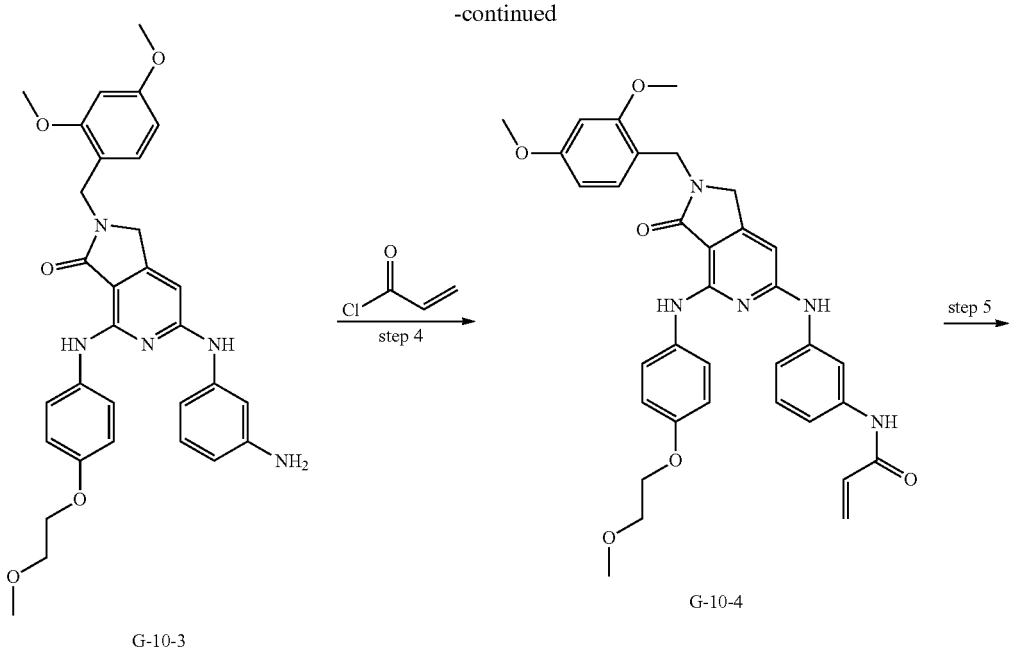

G-10-3

G-10-4

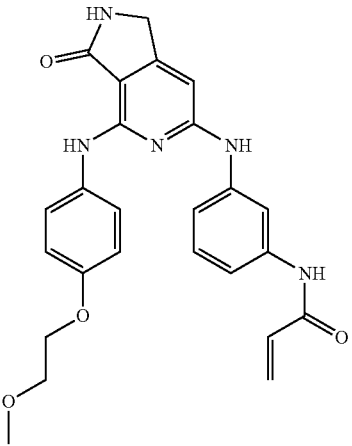

G-10

Step 1: to a 30 ml microwave reactor were added compound 8a (883 mg, 2.5 mmol), 4-(2-methoxyethoxy)aniline (418 mg, 2.5 mmol), N,N-diisopropylethylamine (647 mg, 5 mmol) and 15 ml of N-methylpyrrolidone. The reaction mixture was stirred at 200° C. for 1 hour. After N-methylpyrrolidone was removed by concentration, the residue was purified by Combi-flash column chromatography [hexane containing 0-80% ethyl acetate] to give G-10-1 (550 mg, 45.5%) as a yellow solid. MS m/z (ESI): 484[M+H]$^+$.

Step 2: to a 30 ml microwave reactor were added Pd$_2$(dba)$_3$ (24 mg, 0.026 mmol), Xantphos (30 mg, 0.052 mmol), cesium carbonate (337 mg, 1.034 mmol), compound G-10-1 (250 mg, 0.517 mmol), m-diphenylamine (71 mg, 0.514 mmol) and 1,4-dioxane (10 ml). The reaction mixture was stirred at 160° C. for 30 min. The reaction mixture was washed with water, extracted with ethyl acetate, and purified by Combi-flash column chromatography [hexane containing 0-100% ethyl acetate] to give 270 mg of G-10-2 as a brown solid. MS m/z (ESI): 586.2[M+H]$^+$.

Step 3: to a 100 ml flask were added compound G-10-2 (270 mg, 0.461 mmol), iron powder (130 mg, 2.321 mmol), ammonium chloride solution (2 ml), THF (4 ml), water (2 ml) and ethanol (4 ml). The reaction mixture was stirred at 75° C. for 2 hours, filtered and 30 ml of ethyl acetate was added. The reaction solution was washed with 30 ml of water and 30 ml of brine. The organic phase was dried and concentrated to give 280 mg of G-10-3 as a brown solid. MS m/z (ESI): 556.2[M+H]$^+$.

Steps 4-5: using compound G-10-3 as a starting material, compound G-10 was obtained by a method similar to the steps 2 and 3 in Example 3. MS m/z (ESI): 460.2[M+H]$^+$. $^1$H NMR (400 MHz, DMSO-d$_6$) δ 10.06 (s, 1H), 9.23 (s, 1H), 8.75 (s, 1H), 8.07 (s, 1H), 7.78 (s, 1H), 7.55 (d, J=8.8 Hz, 2H), 7.37 (d, J=5.9 Hz, 1H), 7.19 (d, J=5.8 Hz, 2H), 6.78 (d, J=8.9 Hz, 2H), 6.42 (dd, J=16.9, 10.3 Hz, 1H), 6.22 (d, J=19.7 Hz, 2H), 5.71 (d, J=11.7 Hz, 1H), 4.25 (s, 2H), 4.06-3.92 (m, 2H), 3.67-3.55 (m, 2H), 3.28 (s, 3H).

Example 11 Preparation of N-(3-(4-(1-methyl-1H-pyrazol-4-yl)-5-oxo-6,7-dihydro-5H-pyrrolo[3,4-d]pyrimidin-2-ylamino)phenyl)acrylamide (G-11)

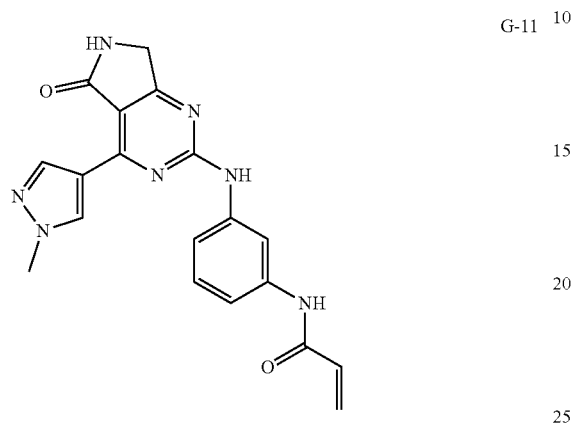

G-11

The preparation method for compound G-11 was the same as that in example 2, except that compound 1a in step 1 was replaced by compound 4a. MS m/z (ESI): 376.1[M+H]$^+$. $^1$H NMR (400 MHz, DMSO-d$_6$) δ 10.16 (s, 1H), 9.96 (s, 1H), 9.15 (s, 1H), 8.65 (s, 1H), 8.36 (s, 2H), 7.59-6.86 (m, 3H), 6.48 (s, 1H), 6.28 (s, 1H), 5.75 (s, 1H), 4.27 (s, 2H), 3.91 (s, 3H).

Example 12 Preparation of N-(3-((4-(4-(2-methoxyethoxy)phenoxyl)-5-oxo-6,7-dihydro-5H-pyrrolo[3,4-d]pyrimidin-2-yl)amino)phenyl)acrylamide (G-12)

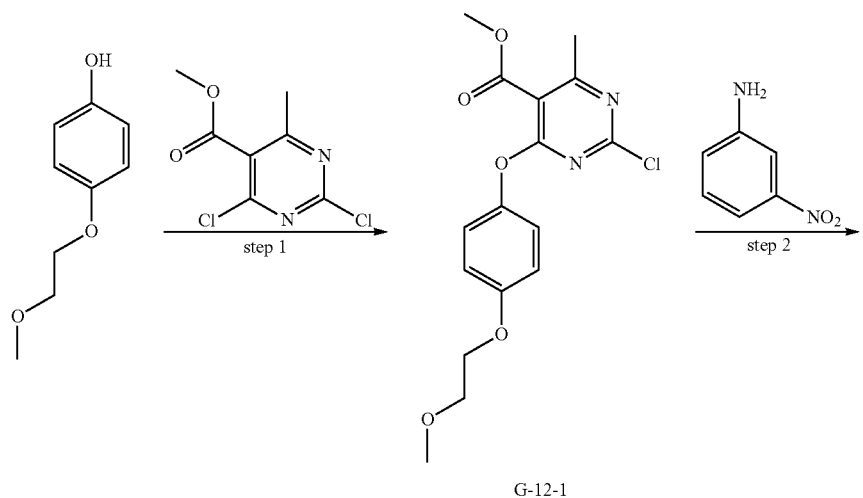

G-12-1

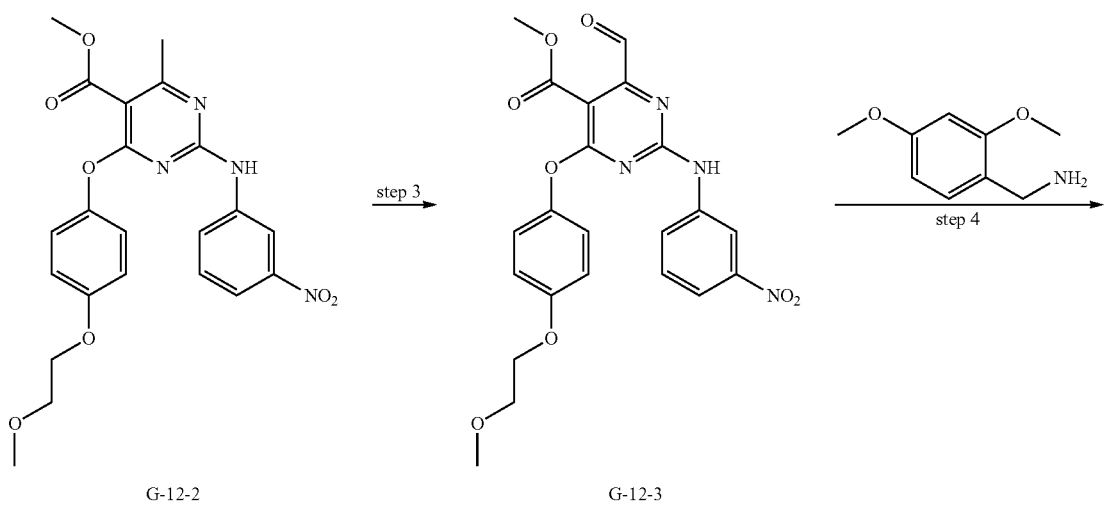
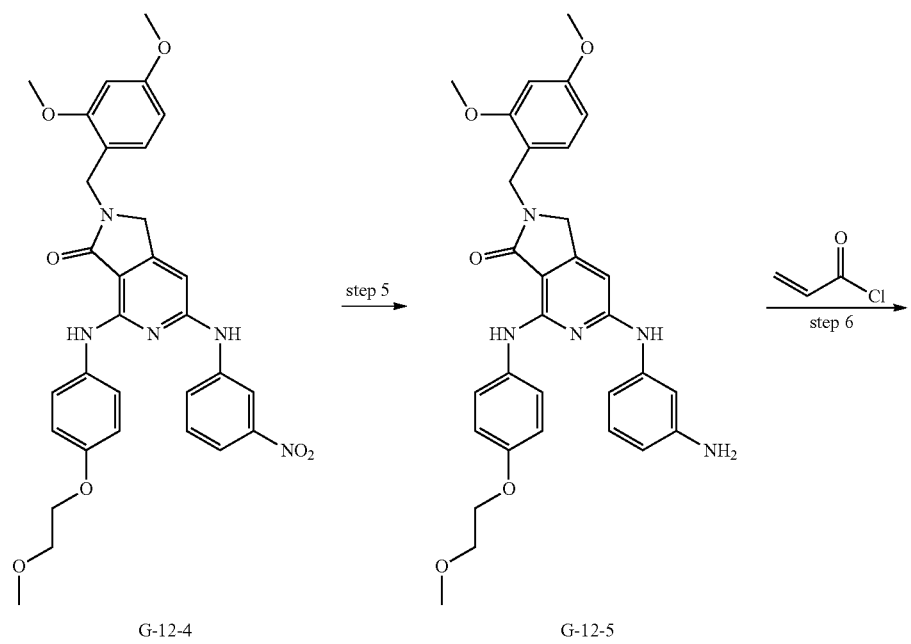

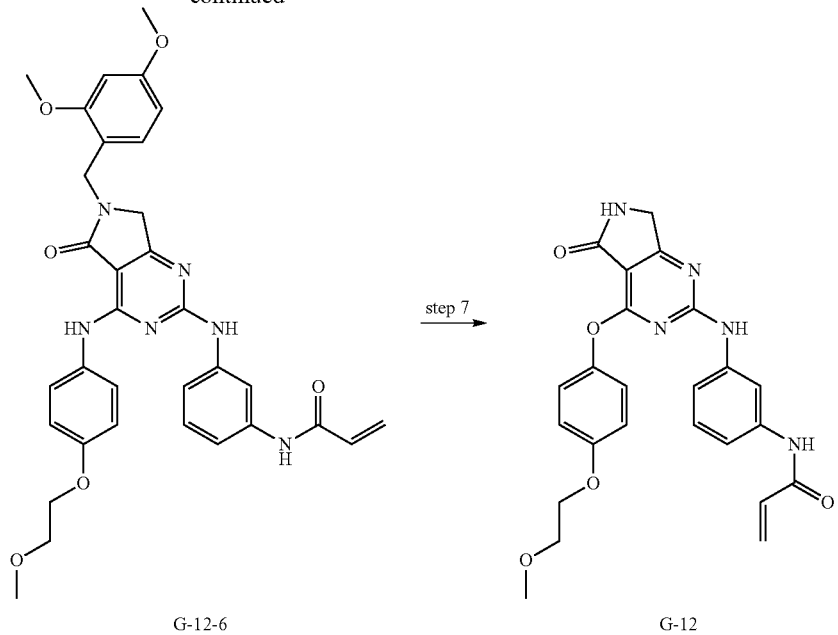

G-12-6 → step 7 → G-12

Step 1: methyl 2,4-dichloro-6-methylpyrimidine-5-carboxylate (110 mg, 0.5 mmol) and 4-(2-methoxy-ethoxy)-phenol (84 mg, 0.5 mmol) were dissolved in 3 ml of DMSO, and potassium carbonate (138 mg, 1.0 mmol) was added. The mixture was stirred at room temperature for 16 hours. The reaction mixture was poured into water, and extracted with ethyl acetate (2×20 ml). The organic phases were combined, washed with water (2×30 ml) and saturated saline (30 ml) successively, dried over anhydrous sodium sulfate, and filtered. The filtrate was concentrated to give a crude product which was purified by Combi-flash column chromatography [PE:EA=100:0~70:30] to give compound G-12-1 (160 mg, 55.6%). $M^+=353.0[M+1]^+$.

Step 2: compound G-12-1 (650 mg, 1.84 mmol) and m-nitroaniline (254 mg, 1.84 mmol) were dissolved in 10 mL of 1,4-dioxane, and p-toluenesulfonic acid (316 mg, 1.84 mmol) was added. The mixture was heated to 90° C. and reacted for 16 hours. The reaction solution was cooled to room temperature, and then poured into water, which was extracted with ethyl acetate (3×30 ml). The organic phases were combined, washed with saturated aqueous sodium bicarbonate (50 ml) and saturated brine (50 ml) successively, dried over anhydrous sodium sulfate, and filtered. The filtrate was concentrated to give a crude product which was purified by Combi-flash column chromatography [PE:EA=100:0~70:30] to give compound G-12-2 (518 mg, 62%). $M^+=455.3[M+1]^+$.

Step 3: to a solution of compound G-12-2 (518 mg, 1.14 mmol) in 1,4-dioxane (10 ml) was added selenium dioxide (760 mg, 6.84 mmol) and the mixture was heated to reflux. After reacting for 48 hours, the reaction mixture was concentrated to give a crude product which was purified by Combi-flash column chromatography [PE:EA=100:0~70:30] to give compound G-12-3 (308 mg, 58%). $M^+=469.2[M+1]^+$.

Step 4: compound G-12-3 (300 mg, 0.64 mmol) and 2,4-dimethoxybenzylamine (214 mg, 1.28 mmol) were dissolved in dichloromethane (15 ml). After stirring at room temperature for 30 minutes, sodium cyanoborohydride (121 mg, 1.92 mmol) was added. After the mixture was stirred at room temperature for 1 hours, the mixture was heated to 60° C. and reacted for another 2 hours. The reaction solution was diluted with 20 ml of dichloromethane, washed with 20 ml of water and 20 ml of saturated brine successively, dried over anhydrous sodium sulfate, and filtered. The filtrate was concentrated to give a crude product which was purified by Combi-flash column chromatography [PE:EA=100:0~0:100] to give compound G-12-4 (180 mg, 48%). $M^+=588.2[M+1]^+$.

Step 5: to a mixed solution of compound G-12-4 (90 mg, 0.15 mmol) in ethanol (4 ml) and water (2 ml) were added iron powder (42 mg, 0.75 mmol) and ammonium chloride (81 mg, 1.5 mmol). The mixture was heated to 60° C. and reacted for 2 hours. The reaction mixture was filtered to remove the solid. The filter cake was washed with ethyl acetate, and the filtrate was washed with saturated brine (10 ml), dried over anhydrous sodium sulfate, and filtered. The filtrate was concentrated under reduced pressure to give compound G-12-5 (76 mg, 89.4%). $M^+=558.2[M+1]^+$.

Step 6: acryloyl chloride (13 mg, 0.136 mmol) and N,N-diisopropylethylamine (35 mg, 0.272 mmol) were added to a solution of compound G-12-5 (76 mg, 0.136 mmol) in dichloromethane (5 ml). The mixture was stirred at room temperature for 2 hours. The reaction solution was diluted with 15 ml of dichloromethane, washed with 10 ml of water and 10 ml of saturated brine successively, dried over anhydrous sodium sulfate, and filtered. The filtrate was concentrated under reduced pressure to give compound G-12-6 (94 mg, 100%), which was used directly in the next step without purification. $M^+=612.2[M+1]^+$.

Step 7: triethylsilane (36 mg, 0.308 mmol) was added to a solution of compound G-12-6 (94 mg, 0.154 mmol) in trifluoroacetic acid (3 ml). The mixture was stirred at room temperature for two hours. The reaction solution was concentrated, and then purified by preparation liquid phase to give compound G-12 (5 mg, 7%). $M^+=462.2[M+1]^+$; $^1$H NMR (400 MHz, dmso) δ 9.99 (s, 1H), 8.38 (s, 1H), 8.16 (s, 1H), 7.65-7.53 (m, 1H), 7.32-7.06 (m, 4H), 7.02-6.85 (m, 3H), 6.42 (dd, J=16.9, 10.3 Hz, 1H), 6.20 (dd, J=17.0, 2.1 Hz, 1H), 5.70 (dd, J=10.1, 2.0 Hz, 1H), 4.27 (s, 2H), 4.12-4.04 (m, 2H), 3.69-3.61 (m, 2H), 3.30 (s, 3H).

Examples 13-16

The preparation methods for compound G-13 to G-16 were the same as that in example 2, except that compound 1a in step 1 was replaced by compound 10a, 11a, 12a or 13a.

| No. | Structure | $^1$HNMR or MS |
|---|---|---|
| Example 13 | 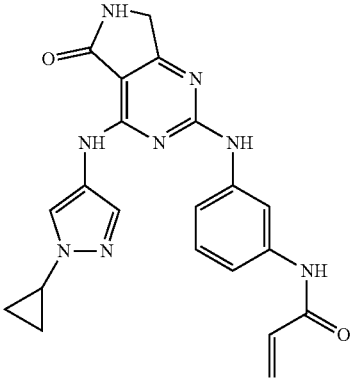<br>G-13 | $^1$H NMR (400 MHz, DMSO-$d_6$): δ 10.14(s, 1H), 9.70(s, 1H), 8.69(s, 1H), 6.25-8.20(m, 1H), 8.12(s, 1H), 7.90(s, 1H), 7.76(s, 1H), 7.47-7.39(m, 2H), 7.30-7.26(m, 1H), 6.51-6.44(m, 1H), 6.27-6.23(m, 1H), 5.76-5.73(m, 1H), 4.23(s, 2H), 3.58(m, 1H), 0.96-0.93(m, 4H). MS(ESI)417.2 [M + H]$^+$ |
| Example 14 | 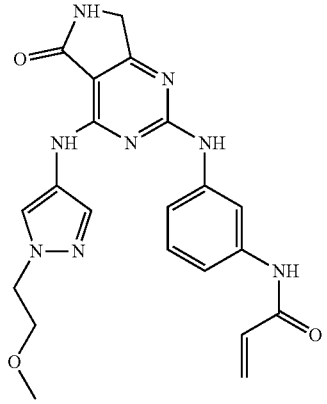<br>G-14 | $^1$H NMR (400 MHz, DMSO-$d_6$): δ 10.13(s, 1H), 9.66(s, 1H), 8.71 (s, 1H), 6.22-8.18(m, 1H), 8.12(s, 1H), 7.90(s, 1H), 7.82(s, 1H), 7.50(s, 1H), 7.28-7.34(m, 1H), 7.27(t, d = 8 Hz, 1H), 6.50-6.44(m, 1H), 6.27-6.23(m, 1H), 5.77-5.74(m, 1H), 4.23(s, 2H), 4.15(m, 2H), 3.65(m, 2H), 3.19(s, 3H). MS(ESI)435.2 [M + H]$^+$ |
| Example 15 | 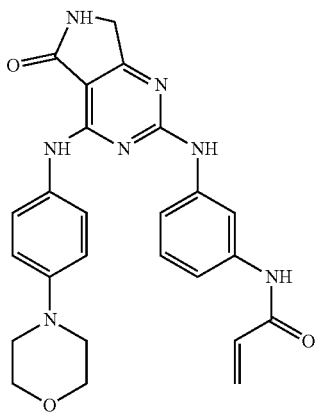<br>G-15 | $^1$H NMR (400 MHz, DMSO-d6): δ 10.12 (s, 1H), 9.73 (s, 1H), 8.57 (s, 1H), 8.20 (s, 2H), 7.86 (s, 1H), 7.62 (d, J = 8.4 Hz, 2H), 7.44 (d, J = 8.0 Hz, 1H), 7.37 (d, J = 8.0 Hz, 1H), 7.22 (dd, J$_1$ = J$_2$ = 8.0 Hz, 1H), 6.87 (d, J = 8.4 Hz, 1H), 6.47 (dd, J$_1$ = 10 Hz, J$_2$ = 17.2 Hz, 1H), 6.26 (dd, J$_1$ = 2 Hz, J$_2$ = 17.2 Hz, 1H), 5.75 (dd, J$_1$ = 1.6 Hz, J$_2$ = 10 Hz, 1H), 4.24 (s, 2H), 3.71-3.76 (m, 4H), 3.02-3.07 (s, 4H). |

| No. | Structure | ¹HNMR or MS |
|---|---|---|
| Example 16 | 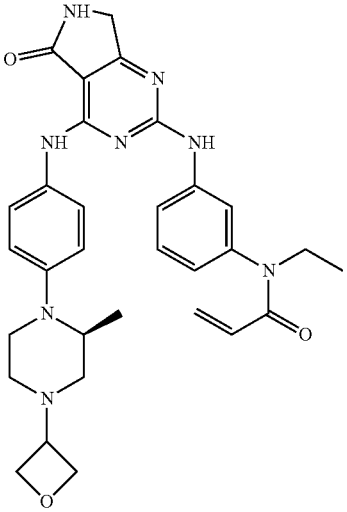<br>G-16 | ¹H NMR (400 MHz, DMSO-d₆) δ 9.83 (s, 2H), 8.56 (s, 1H), 8.19 (s, 1H), 7.70 (s, 1H), 7.47 (m, 2H), 7.34-7.14 (m, 2H), 6.80 (m, 2H), 6.14 (dd, J = 16.9, 2.5 Hz, 1H), 6.01 (s, 1H), 5.53 (d, J = 12.4 Hz, 1H), 4.64-4.49 (m, 2H), 4.50-4.44 (m, 1H), 4.43-4.37 (m, 1H), 4.21 (s, 2H), 3.63 (dd, J = 14.1, 7.2 Hz, 2H), 3.04-2.89 (m, 2H), 2.68 (d, J = 11.0 Hz, 2H), 2.24 (dd, J = 19.8, 16.5 Hz, 2H), 2.04 (t, J = 9.1 Hz, 2H), 0.97 (m, 6H).<br>MS: 569.3 [M + H]⁺ |
| Example 17 | 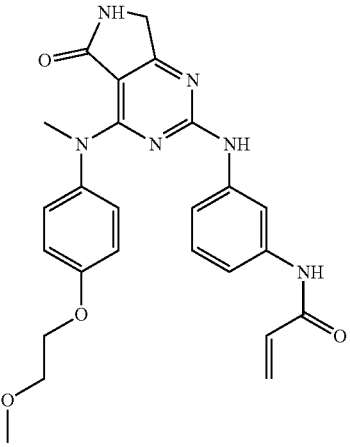<br>G-17 | ¹H NMR (400 MHz, DMSO-d6) δ 9.97 (s, 1H), 9.56 (s, 1H), 7.83 (s, 1H), 7.57 (s, 1H), 7.20-7.15 (m, 4H), 6.96 (d, J = 8.9 Hz, 2H), 6.84 (t, J = 8.0 Hz, 1H), 6.44 (dd, J = 17.0, 10.1 Hz, 1H), 6.22 (dd, J = 17.0, 2.0 Hz, 1H), 5.72 (dd, J = 10.1, 2.1 Hz, 1H), 4.19-4.05 (m, 4H), 3.75 (s, 3H), 3.72-3.67 (m, 2H), 3.32 (s, 3H).<br>MS: 475.3 [M + H]⁺ |

Bioassay

Test Example 1 Lantha Screening Kinase Reaction Assay

The compound was predissolved in 100% DMSO.10 mM drug stock solution was obtained by dissolution at room temperature and then gradiently diluted with 8 vol % DMSO solution to a final concentration of 10-0.005 μM. 2.5 μl of a solution of substance to be tested and 2.5 μl of kinase (Invitrogen PV3363) diluted with the reaction buffer were added into each well of 384-well plate (Corning 3676), and then the mixture of Fluososcei-PolyGT (Invitrogen PV3610) substrate and ATP (Invitrogen PV3227) diluted with 5 μl of the reaction buffer were added to initiate the reaction. Among the wells, the kinase in the blank well was replaced with a reaction buffer and the kinase well (Enzyme) was not added with any drug. After reacting on a shaker at 25° C. for 60 minutes in the dark, 10 μl of Detection Solution (mixture of Invitrogen PV3528 and EDTA, which was diluted with TR-FRET dilution buffer, the working concentration of EDTA was 5 mM, the working concentration of Lanthascreening Tb PY20 antibody was 0.2 nM) was added and shaken at room temperature for 30 minutes. The plates were read on a VictorX5 fluorescent plate reader (PerkinElmer) and the light absorption at an excitation wavelength of 340 nm and emission wavelengths of 500 nm and 520 nm was measured.

The method for calculating the inhibition rate (referring to the instruction of PV3363, Invitrogen) was as follows:

$$\text{emission rate (ER): Coumarin Emission (520 nm)/Fluorescein Emission (500 nm)} \qquad 1.$$

$$\text{the inhibition rate (IR): } (ER_{kinase} - ER_{test\ compound})/(ER_{kinase} - ER_{blank}) \times 100\%. \qquad 2.$$

The half-inhibitory concentration $IC_{50}$ was calculated by fitting with XLFIT 5.0 software (IDBS, UK). The result was show in table 1:

TABLE 1 the inhibitory activity of compound against to BTK WT

| Compound | BTK WT IC50(nM) |
|---|---|
| G-1 | 141 |
| G-2 | 25 |
| G-3 | 58 |
| G-4 | 10 |
| G-5 | 156 |
| G-6 | 14 |
| G-7 | 19 |
| G-8 | 9 |
| G-9 | 55 |
| G-10 | 68 |
| G-11 | 48 |
| G-12 | 1348 |
| G-13 | 63 |
| G-14 | 59 |
| G-15 | 52 |
| G-16 | 44 |
| G-17 | >10000 |

It can be seen from table 1 that the representative compounds of the present disclosure have high inhibitory activity against enzyme. It is found that when Y is a hetero atom in the structure of the compound of the present disclosure, the choice of Y has a significant effect on the final inhibitory activity of the compound. When Y is O, the inhibitory activity of the compound is significantly reduced (such as compounds G-12 and G-2), or when Y is N and has a substituent such as a methyl group, the inhibitory activity of the compound is significantly lowered (e.g., compounds G-17 and G-2).

Test Example 2 Experimental HTRF Method for Detecting Intracellular βBTK Y223 Phosphorylation The compound was predissolved in 100% DMSO. 10 mM drug stock solution was obtained by dissolution at room temperature and then gradiently diluted with 5 vol % DMSO solution to a final concentration of 3-0.0014 μM. Ramos cells were seeded into a 96-well plate at a density of $4\times10^5$/well with 45 μl of 1640 medium containing 10% (V/V) FBS per well, and 5 μl of diluted solution of substance to be tested was added to each well. Incubation was performed for 1 hour at 37° C., 5% (V/V) $CO_2$. 10 μl of sodium pervanadate dilution (diluted with 1640 without serum) was added, and 10 μl of serum-free medium was added to the negative control wells. Incubation was performed at 25° C. for 30 minutes on a shaker. 20 μl of lysate (4× lysate: blocked mother liquor is equal to 25:1) was added to each well and incubated for 30 minutes at 25° C. on a shaker. The 96-well plate was shaken on an oscillator at 800 rpm for 1 minute. 16 μl of cell lysate was added to a 384-well plate (Greiner 784075), and 4 μl of pre-mixed antibody solution (Phospho-BTK d2 antibody and Phospho-BTK Cryptate antibody diluted 20-fold with the test solution) was added. Incubation was performed at 25° C. overnight on a shaker. The plate was read on a VictorX5 fluorescent plate reader (PerkinElmer) and the light absorption at an excitation wavelength of 317 nm and emission wavelengths of 500 nm and 520 nm was measured (referring to the instruction of 63ADK017PEH, Cisbio). The half-inhibitory concentration $IC_{50}$ was calculated by fitting with XLFIT 5.0 software (IDBS, UK). The result was show in table 2:

TABLE 2 the inhibitory activity of compound against βBTK Y223 cell

| Compound | βBTK Y223 IC50(nM) |
|---|---|
| G-2 | 43 |
| G-3 | 106 |
| G-4 | 6 |
| G-6 | 20 |
| G-7 | 111 |
| G-8 | 36 |
| G-9 | 82 |
| G-10 | 164 |
| G-11 | 4 |
| G-13 | 81 |
| G-14 | 103 |
| G-15 | 36 |
| G-16 | 62 |

It can be seen from table 2 that the representative compounds of the present disclosure have high inhibitory activity against cells.

Test Example 3: Wild Type EGFR Kinase Inhibition Test

All the following reagents used in z-lyte test are commercially available from Invitrogen.

The inhibitory activity of compounds to be tested on wild-type EGFR kinase (Invitrogen, PV3872) was measured by z-lyte methods.

The working concentration of each component in 10 μl of wild-type EGFR kinase reaction system was as follows: 10M ATP, 0.8 ng/μl wild-type EGFR kinase (Invitrogen, PV3872), and 2 μM Tyr04 substrate (Invitrogen, PV3193). After the compounds to be tested were added, the final concentration of DMSO was 2%.

10 mM drug stock solutions dissolved at room temperature were gradiently diluted with 4% DMSO in water to a final concentration of 10-0.005 μM. To each well were added 2.5 μl of a solution of the compounds to be tested and 5 μl of a mixture of wild-type EGFR kinase and Tyr04 substrate diluted by a reaction buffer, and then 2.5 μl of ATP was added to initiate the reaction. Reaction buffer instead of ATP were added to C1 wells, no drugs were added to C2 wells, and the phosphorylated substrates were added to C3 wells according to the instruction. After reacting on a shaker at 25° C. for 60 minutes in the dark, 5 μl of Development Reagent B (Invitrogen, diluted with TR-FRET dilution buffer) was added, and reacted on a shaker at room temperature for 60 min. The plate was read in a VictorX5 fluorescent microplate reader (PerkinElmer) and the light absorbance at an excitation wavelength of 405 nm and emission wavelengths of 450 nm and 520 nm was measured (For example, $C3_{520\ nm}$ represents the reading of C3 well at 520 nm).

The calculation method for the inhibition ratio (referring to the instruction of PV3363, Invitrogen) was as follows:

ER=Coumarin Emission (450 nm)/Fluorescein Emission (520 nm)    1.

Phosphorylation ratio=$(1-((ER \times C3_{520\ nm} - C3_{450\ nm})/((C1_{450\ nm} - C3_{450\ nm}) + ER \times (C3_{520\ nm} - C1_{520\ nm}))) \times 100\%$    2.

Inhibition ratio (IR)=(1-phosphorylation ratio of the test compound)/(phosphorylation ratio of C2))×100%    3.

The half-inhibitory concentration $IC_{50}$ was calculated by fitting with XLFIT 5.0 software (IDBS, UK).

TABLE 3

| the inhibitory activity of compound against EGFR WT | |
|---|---|
| Compound | EGFR WT IC50(nM) |
| G-1 | 9267 |
| G-2 | 4688 |
| G-3 | >10000 |
| G-4 | 3000 |
| G-5 | 7854 |
| G-6 | 2997 |
| G-7 | 6989 |
| G-8 | 6420 |
| G-9 | 5029 |
| G-10 | >10000 |
| G-11 | >10000 |
| G-12 | 1532 |
| G-13 | 3076 |
| G-14 | 2689 |
| G-15 | 4265 |
| G-16 | 5679 |
| G-17 | >10000 |

It can be seen from table 3 that the representative compounds of the present disclosure have lower inhibitory activity against wild-type EGFR kinase. Therefore, the exemplary compounds of the present disclosure had selective inhibitory activities against BTK WT kinase.

All publications mentioned herein are incorporated by reference as if each individual document is cited as a reference, as in the present application. It should also be understood that, after reading the above teachings of the present disclosure, those skilled in the art can make various changes or modifications, equivalents of which falls in the scope of claims as defined in the appended claims.

What is claimed:

1. A compound of formula (II), or a pharmaceutically acceptable salt, or stereoisomer, thereof:

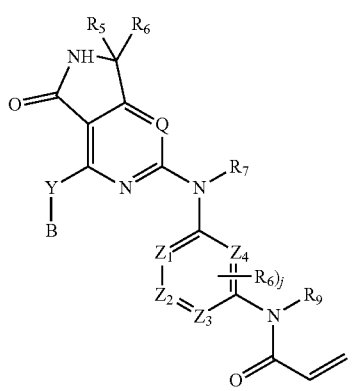

(II)

wherein, Y is a bond, and; B is a 5- to 6-membered monocyclic heteroaryl ring, and the 5- to 6-membered monocyclic heteroaryl ring is optionally substituted by 1, 2 or 3 substituents selected from a group A1; or
Y is $NR_{a1}$; $R_{a1}$ is hydrogen or $C_{1-3}$ alkyl; and B is phenyl or a 5- to 6-membered monocyclic heteroaryl ring, and B is optionally substituted by 1, 2 or 3 substituents selected from the group A1;

wherein the substituent of the group A1 is selected from the group consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxyl, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (CH$_2$), or C(O), L is a 4- to 6-membered saturated mono heterocyclic ring, p and q are each independently 1, 2 or 3;

wherein the 4- to 6-membered saturated monoheterocyclic ring in the substituents of the group A1 is unsubstituted or substituted with 1, 2 or 3 groups selected from the group consisting of halogen, hydroxy, $C_{1-3}$ alkyl, O=, $NR_{a0}R_{b0}$, hydroxymethyl, hydroxyethyl, hydroxypropyl, carboxyl, —C(O)OC$_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl;

Q is N or $CR_{b1}$, wherein $R_{b1}$ is selected from the group consisting of hydrogen, halogen, cyano, $C_{1-8}$ alkyl, halogenated $C_{1-8}$ alkyl, $C_{1-8}$ alkoxy, $C_{3-8}$ cycloalkyl and $C_{3-8}$ cycloalkoxy;

three of $Z_1$, $Z_2$, $Z_3$ and $Z_4$ are CH, and one of $Z_1$, $Z_2$, $Z_3$ and $Z_4$ is N; or $Z_1$, $Z_2$, $Z_3$ and $Z_4$ are CH;

$R_5$ and $R_6$ are each independently selected from the group consisting of hydrogen, halogen, $C_{1-8}$ alkyl, halogenated $C_{1-8}$ alkyl, $C_{1-8}$ alkoxy, $C_{3-8}$ cycloalkyl and $C_{3-8}$ cycloalkoxy;

$R_7$ and $R_9$ are each independently selected from the group consisting of hydrogen, $C_{1-8}$ alkyl, halogenated $C_{1-8}$ alkyl, and $C_{3-8}$ cycloalkyl;

$R_8$ is selected from the group consisting of hydrogen, halogen, cyano, $C_{1-8}$ alkyl, $C_{1-8}$ alkoxy, halogenated $C_{1-8}$ alkyl, $C_{3-8}$ cycloalkyl and $NR_{a0}R_{b0}$, wherein $R_{a0}$ and $R_{b0}$ are each independently selected from the group consisting of hydrogen, acetyl, $C_{1-8}$ alkyl, $C_{1-8}$ alkoxy-substituted $C_{1-8}$ alkyl; and j is 0, 1, 2, 3 or 4.

2. The compound of claim 1, or a pharmaceutically acceptable salt, or stereoisomer thereof, wherein Y is a bond, and B is a structure selected from the group consisting of

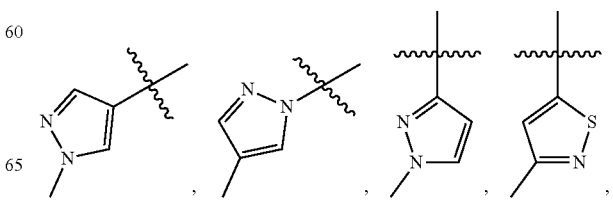

-continued

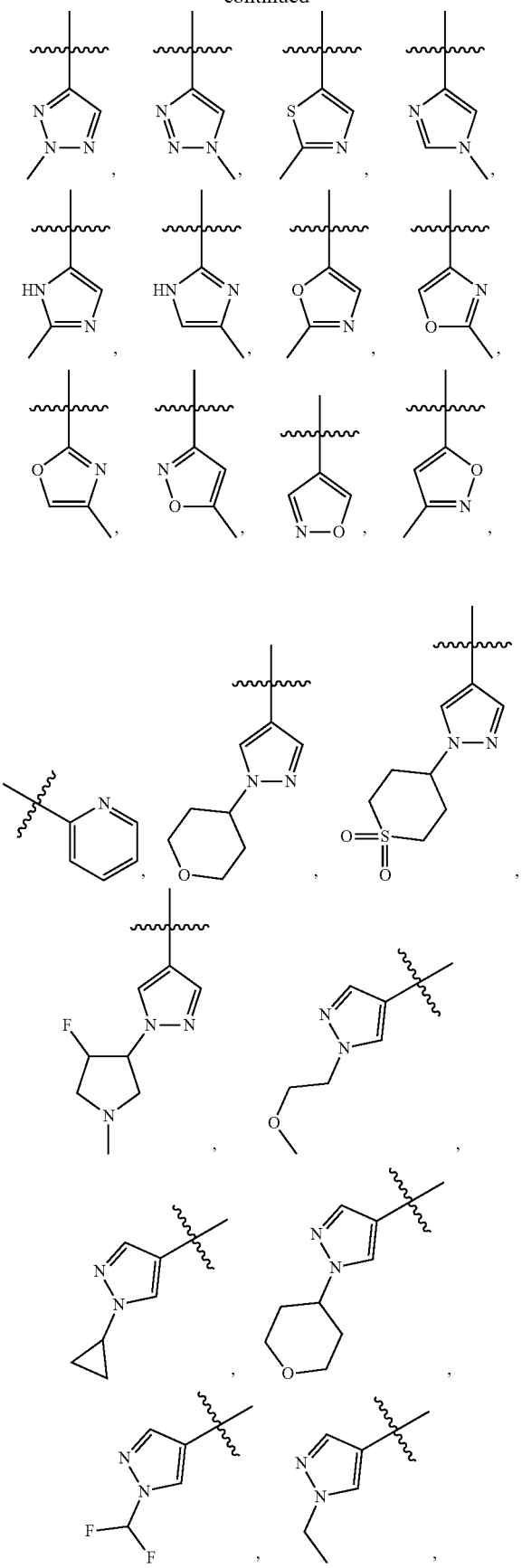

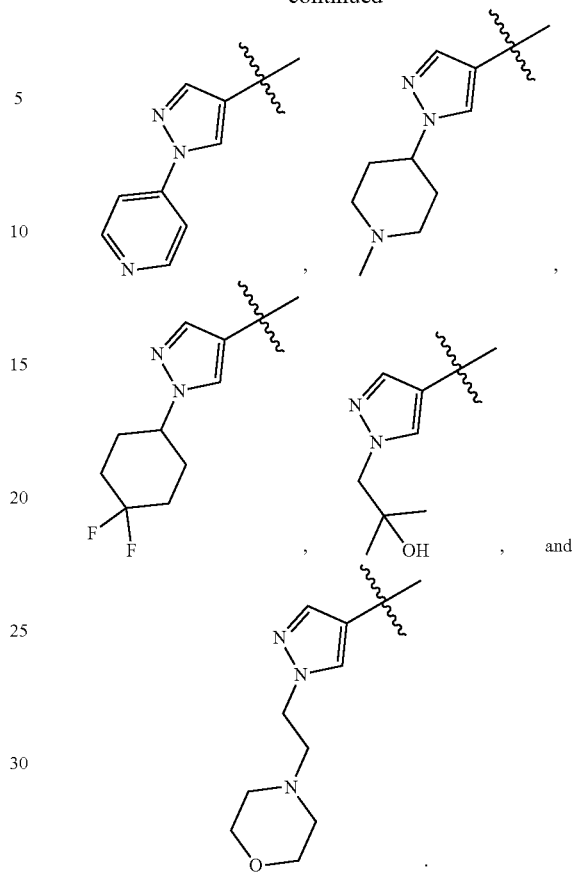

3. The compound of claim 1, or a pharmaceutically acceptable salt or stereoisomer thereof, wherein Y is a bond, and B is a pyrazole ring optionally substituted by 1, 2 or 3 substituents selected from the group A1 wherein the substituent of the group A1 is selected from the group consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, C$_{1-8}$ alkyl, C$_{3-8}$ cycloalkyl, halogenated C$_{1-8}$ alkyl, halogenated C$_{3-8}$ cycloalkyl, hydroxy-substituted C$_{1-8}$ alkyl, hydroxymethyl, hydroxyethyl, hydroxy, carboxyl, NR$_{a0}$R$_{b0}$, —C(O)OC$_{1-6}$ alkyl, acetyl, C$_{1-8}$ alkoxy, C$_{1-8}$ alkoxy-substituted C$_{1-8}$ alkyl, halogenated C$_{1-8}$ alkoxy, —SO$_2$C$_{1-8}$ alkyl, C$_{6-10}$ aryl, 5- to 6-membered monocyclic heteroaryl and —Y-L; wherein Y is (CH$_2$)$_q$ or C(O), L is a 4- to 6-membered saturated mono heterocyclic ring, p and q are each independently 1, 2 or 3;

wherein the 4- to 6-membered saturated monoheterocyclic ring in the substituents of the group A1 is unsubstituted or substituted with 1, 2 or 3 groups selected from the group consisting of halogen, hydroxy, C$_{1-3}$alkyl, O=, NR$_{a0}$R$_{b0}$, hydroxymethyl, hydroxyethyl, hydroxypropyl, carboxyl, —C(O)OC$_{1-3}$ alkyl, acetyl, halogenated C$_{1-3}$ alkyl, C$_{1-3}$ alkoxy, C$_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

4. The compound of claim 1, or a pharmaceutically acceptable salt or stereoisomer thereof, wherein Y is $NR_{a1}$; $R_{a1}$ is hydrogen or $C_{1-3}$ alkyl; B is phenyl or pyrazole ring, and B is optionally substituted by 1, 2 or 3 substituents selected from the group A1 wherein the substituent of the group A1, is selected from the group consisting of halogen, —O(CH$_2$)$_p$OC$_{1-8}$ alkyl, —O(CH$_2$)$_p$OH, —(C$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxyl, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (C$_2$)$_q$ or C(O), L is a 4- to 6-membered saturated mono heterocyclic ring, p and q are each independently 1, 2 or 3;

wherein the 4- to 6-membered saturated monoheterocyclic ring in the substituents of the group A1 is unsubstituted or substituted with 1, 2 or 3 groups selected from the group consisting of halogen, hydroxy, $C_{1-3}$ alkyl, O=, $NR_{a0}R_{b0}$ hydroxymethyl, hydroxyethyl, hydroxypropyl, carboxyl, —C(O)OC$_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

5. The compound of claim 1, or a pharmaceutically acceptable salt or stereoisomer thereof, wherein Y is $NR_{a1}$; $R_{a1}$i is hydrogen or $C_{1-3}$ alkyl; and B is phenyl or a pyrazole ring optionally substituted by 1, 2 or 3 substituents selected from the group A1 wherein the substituent of the group A1 is selected from the group consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxyl, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (C$_2$)$_q$ or C(O), L is a 4- to 6-membered saturated mono heterocyclic ring, p and q are each independently 1, 2 or 3;

wherein the 4- to 6-membered saturated monoheterocyclic ring in the substituents of the group A1 is unsubstituted or substituted with 1, 2 or 3 groups selected from the group consisting of halogen, hydroxy, $C_{1-3}$ alkyl, O=, $NR_{a0}R_{b0}$ hydroxymethyl, hydroxyethyl, hydroxypropyl, carboxyl, —C(O)OC$_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

6. The compound of claim 1, or a pharmaceutically acceptable salt or stereoisomer thereof, wherein Y is $NR_{a1}$; $R_{a1}$ is hydrogen or $C_{1-3}$ alkyl; and B is a structure selected from the group consisting of

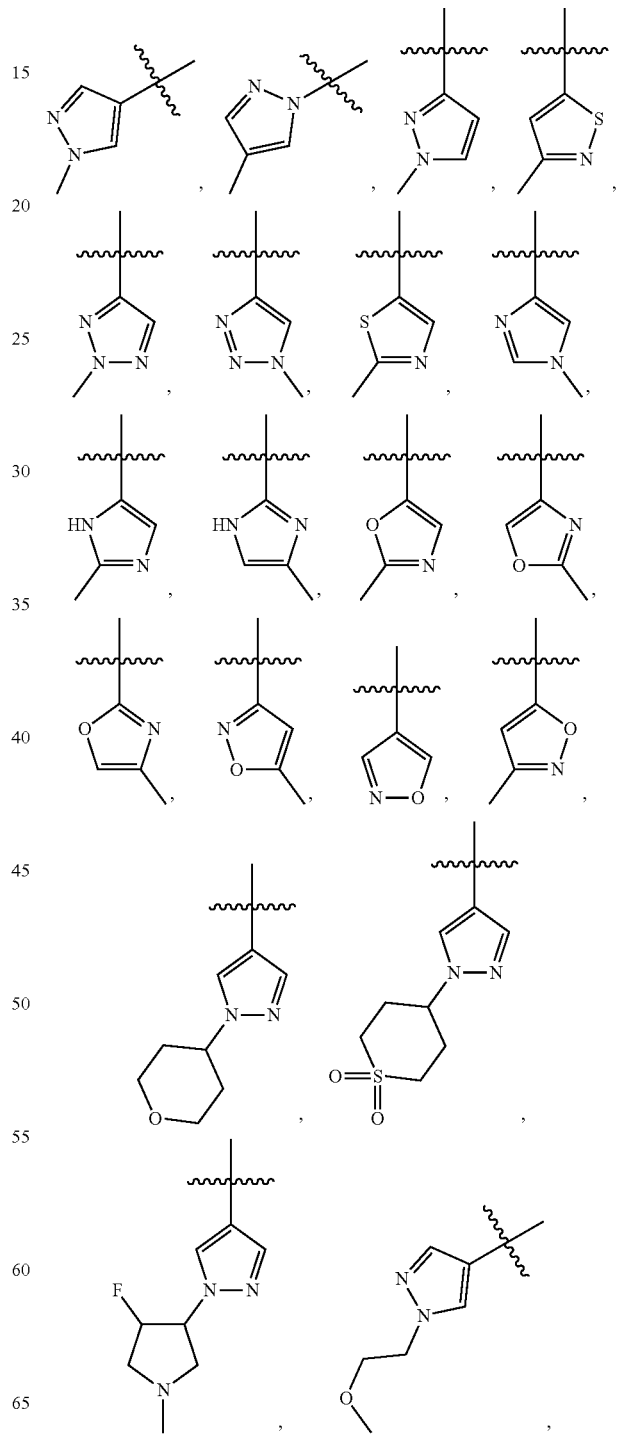

105
-continued
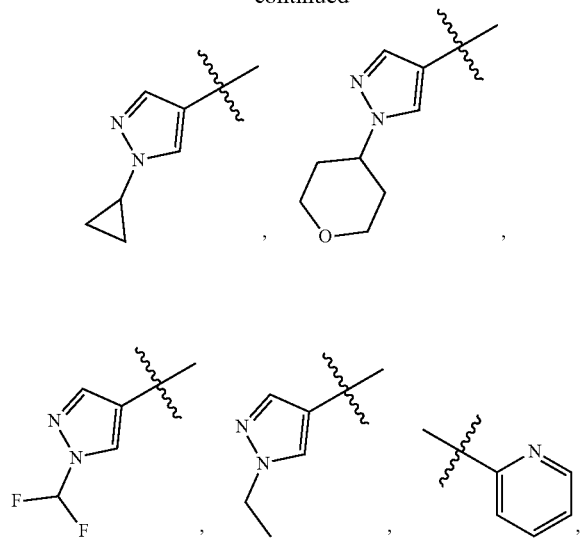
106
-continued
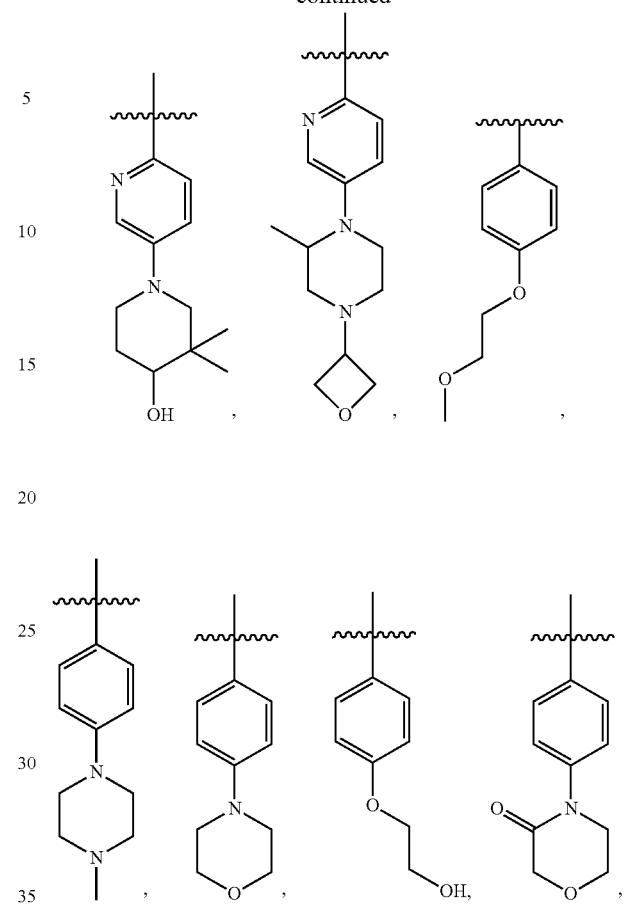
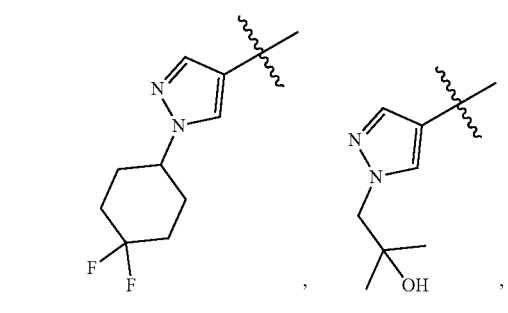
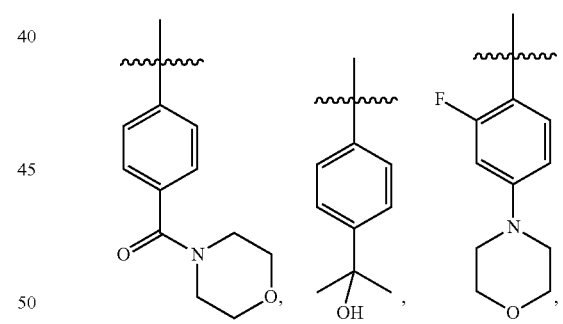
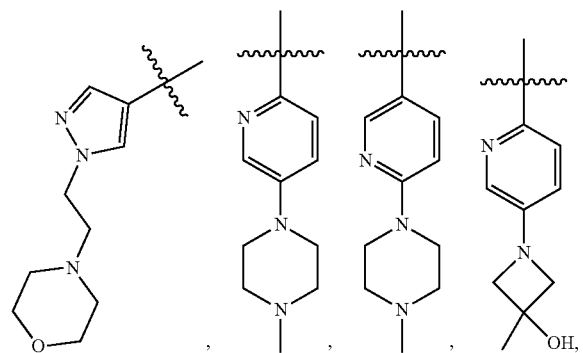
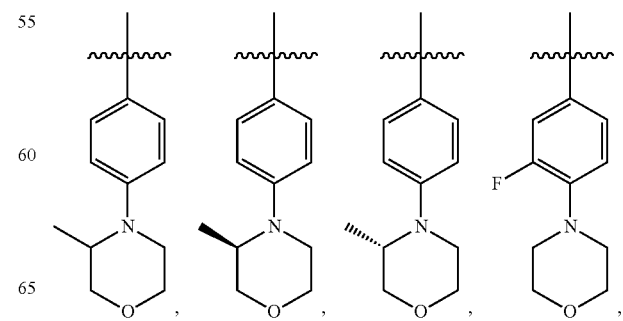

-continued

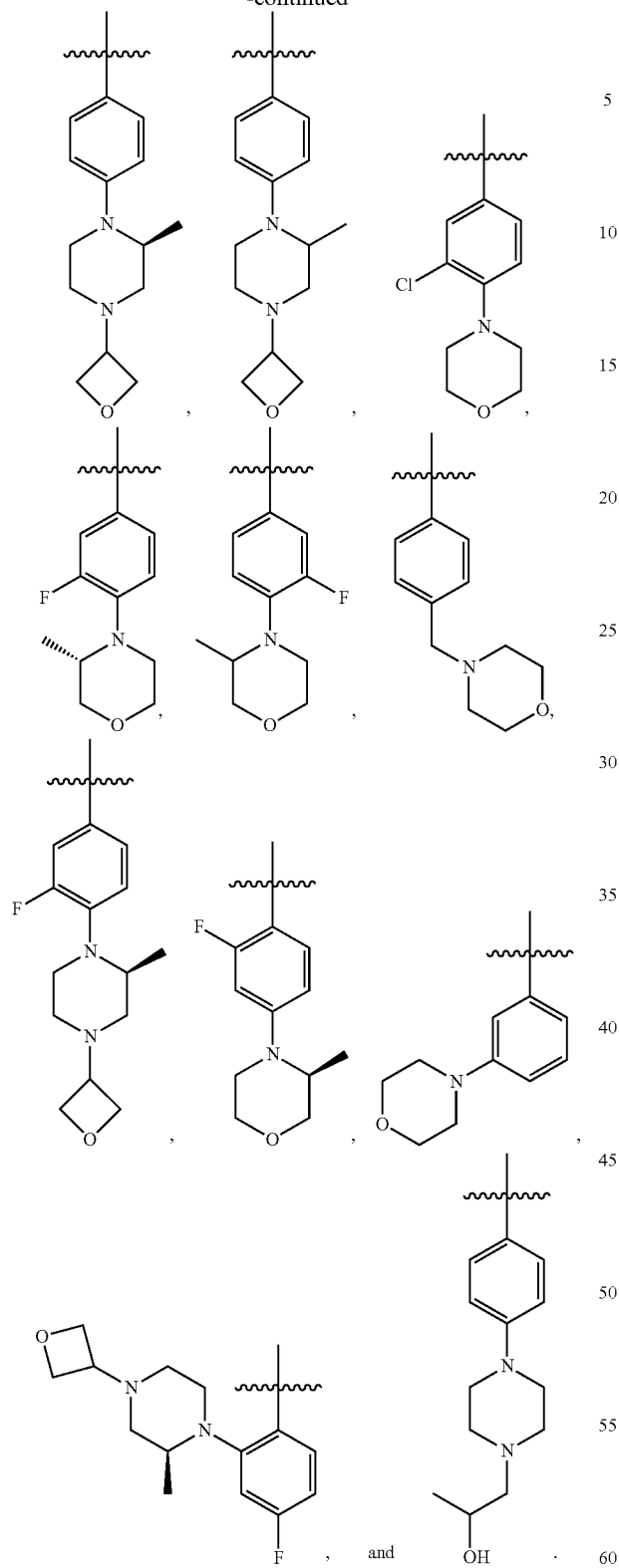

7. The compound of claim 1, or a pharmaceutically acceptable salt, or stereoisomer thereof, wherein $R_7$ and $R_9$ are each independently selected from the group consisting of hydrogen, $C_{1-3}$ alkyl, halogenated $C_{1-3}$ alkyl, and $C_{3-6}$ cycloalkyl.

8. The compound of claim 1, or a pharmaceutically acceptable salt or stereoisomer thereof, wherein the compound of formula (II) is a structure selected from the group consisting of

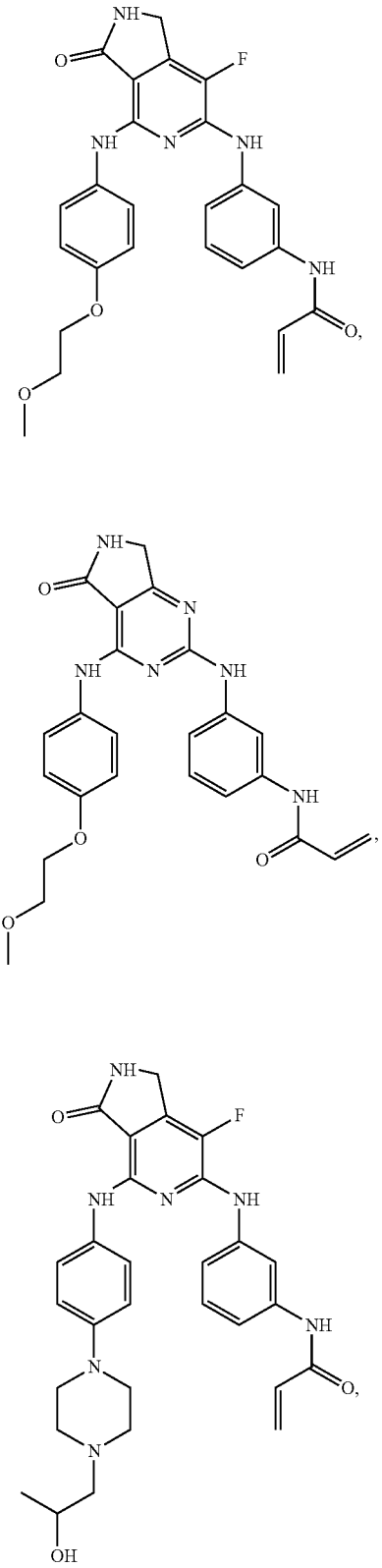

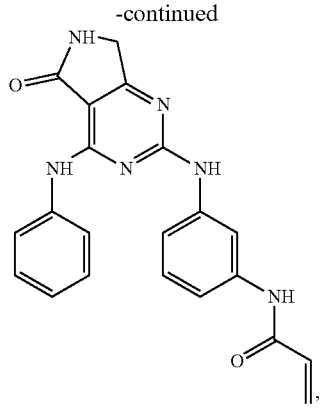
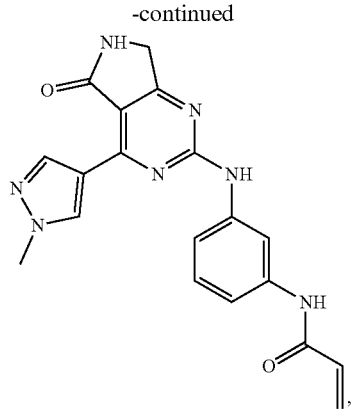
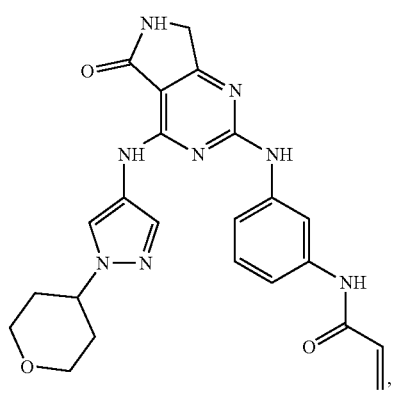
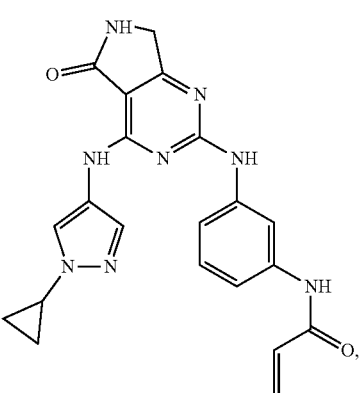
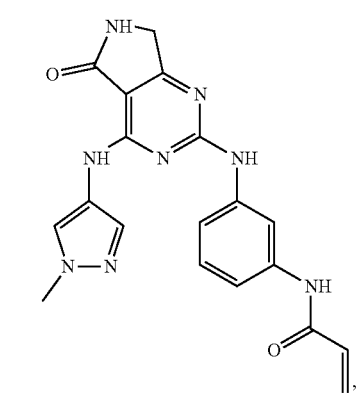
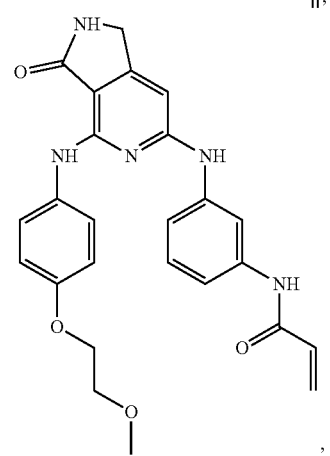
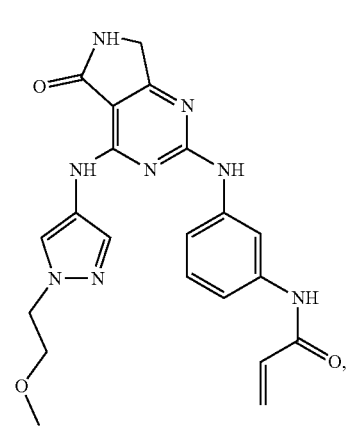

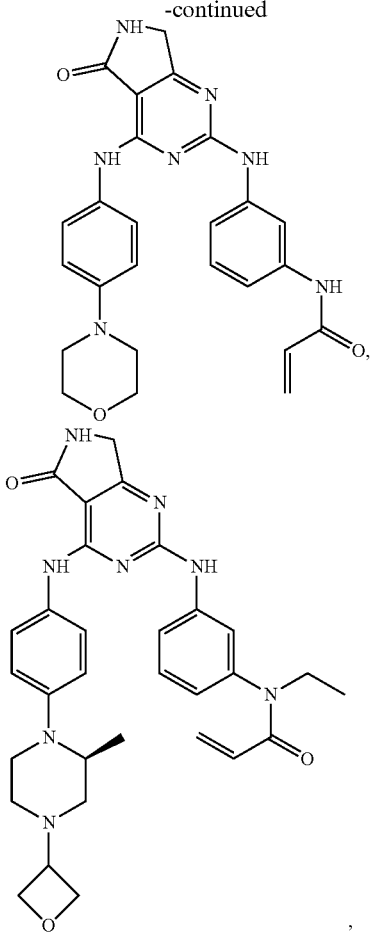

, and

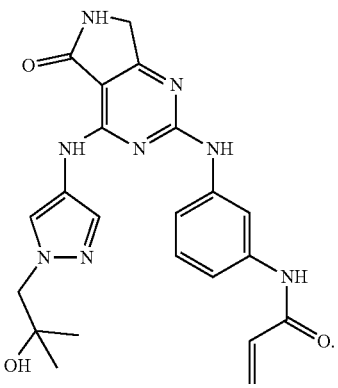

.

9. A pharmaceutical composition comprising the compound of claim 1 and a pharmaceutically acceptable carrier or excipient.

10. A method of inhibiting BTK activity in a subject in need thereof, comprising administering to the subject the compound of claim 1.

11. The method of claim 10, wherein the subject is in need of treating a B cell-mediated disease.

12. The method of claim 10, wherein the subject is in need of treating at least one of a tumor disease, a proliferative disease, an allergic disease, an autoimmune disease, and an inflammatory disease.

* * * * *